(12) United States Patent
Srivastava et al.

(10) Patent No.: US 8,735,568 B2
(45) Date of Patent: May 27, 2014

(54) METHODS OF MODULATING SMOOTH MUSCLE CELL PROLIFERATION AND DIFFERENTIATION

(75) Inventors: Deepak Srivastava, San Francisco, CA (US); Kimberly R. Cordes, San Francisco, CA (US)

(73) Assignee: The J. David Gladstone Institutes, San Francisco, CA (US)

( * ) Notice: Subject to any disclaimer, the term of this patent is extended or adjusted under 35 U.S.C. 154(b) by 0 days.

(21) Appl. No.: 13/254,984

(22) PCT Filed: Mar. 8, 2010

(86) PCT No.: PCT/US2010/026542
§ 371 (c)(1),
(2), (4) Date: Nov. 14, 2011

(87) PCT Pub. No.: WO2010/104796
PCT Pub. Date: Sep. 16, 2010

(65) Prior Publication Data
US 2012/0093789 A1    Apr. 19, 2012

Related U.S. Application Data

(60) Provisional application No. 61/158,632, filed on Mar. 9, 2009.

(51) Int. Cl.
*C07H 21/04* (2006.01)
*C07H 21/02* (2006.01)

(52) U.S. Cl.
USPC ........................ 536/24.5; 536/23.1

(58) Field of Classification Search
CPC ............ C12N 2310/141; C12N 2330/10; C12N 15/113
See application file for complete search history.

(56) References Cited

U.S. PATENT DOCUMENTS

| 5,716,394 A | 2/1998 | Bruchman et al. |
| 2005/0261218 A1 | 11/2005 | Esau et al. |
| 2009/0226375 A1 | 9/2009 | Olson et al. |

FOREIGN PATENT DOCUMENTS

WO  WO 2009/105759  8/2009

OTHER PUBLICATIONS

Akyurek, et al, "SM22 Alpha Promoter Targets Gene Expression to Vascular Smooth Muscle Cells in Vitro and in Vivo", Molecular Medicine, 2000, 6(11): 983-991.
Chen, et al. "MicroRNAs Modulate Hematopoietic Lineage Differentiation", Science, 2004, 303(5654): 83-86.
Ivey, et al., "MicroRNA Regulation of Cell Lineages in Mouse and Human Embryonic Stem Cells", Cell Stem Cells, 2008, 2(3):219-229.
Moretti, et all. "Multipotent Embryonic lsl1+ Progenitor Cells Lead to Cardiac, Smooth Muscle and Endothellial Cell Diversion", Cell, 2006, 127(6):1151-1165.
Shin, et al., "A Single Lentiviral Vector Platform for microRNA-based Conditional RNA Interference and Coordinated Transgene Expression", Proc. National Academy of Science, 2006, 103(37):13759-13764.
Xie, et al., "MicroRNAs Induced During Adipogenesis that Accelerate Fat Cell Development are Downregulated in Obesity", Diabetes, Feb. 2009, 58(5): 1050-1057.

*Primary Examiner* — Amy Bowman
(74) *Attorney, Agent, or Firm* — Paula A. Borden; Bozicevic, Field & Francis LLP.

(57) ABSTRACT

The present disclosure provides methods of inducing smooth muscle cell differentiation. The present disclosure provides genetically modified cells comprising exogenous miR-143 and/or miR-145 nucleic acids; and artificial tissues comprising the genetically modified cells. The present disclosure provides methods and compositions for reducing pathological angiogenesis. The present disclosure provides methods of inducing therapeutic angiogenesis. The present disclosure provides methods, compositions, and devices for inhibiting vascular smooth muscle cell proliferation.

18 Claims, 16 Drawing Sheets

FIG. 6A miR-143 stem-loop
*H. sapiens;* MI0000459
GCGCAGCGCCCUGUCUCCCAGCCUGAGGUGCAGUGCUGCAUCUCUGGUCAGUUGGGAGUCUGAGA
UGAAGCACUGUAGCUCAGGAAGAGAGAAGUUGUUCUGCAGC (SEQ ID NO:1)

--------------------------------

*Homo sapiens* miR-143 precursor stem-loop

```
  -gc    c   ccug    c ag        g           g       u  -  ag
     gcag gc   ucuc c  ccugag uacaungca caucuc gg uc   u
     |||| ||   |||| |  |||||| |||||||| |||||| || ||
     cguc ug   agag g  ggacuc augcacga guagag cu ag   u
  cga    u   juga    a aa       g           a       u  g  gg
```
(SEQ ID NO:1)

-------------------------------- miR-143 mature sequence (-61 to -81)

*H. sapiens;* MIMAT0000435
UGAGAUGAAGCACUGUAGCUC (SEQ ID NO:2)

Fig. 6B miR-145 stem-loop
*H. sapiens;* MI0000461

CACCUUGUCCUCACGGUCCAGUUUUCCCAGGAAUCCCUUAGAUGCUAAGAUGGGGAUUCCUGGAA
AUACUGUUCUUGAGGUCAUGGUU (SEQ ID NO:3)

---

*Homo sapiens* miR-145 precursor stem-loop

```
c    u  u     c   uc    u  c                 uagau
 acc ug ccuca gg  cagu uu ccaggaaucccu           g
 ||| || ||||| ||  |||| || ||||||||||||           c
 ugg ac ggagu uc  guca aa gguccuuagggg           u
u   u  u  -   uu    u  a                 uagaa
```
(SEQ ID NO:3)

--- miR-145 mature sequence (-61 to -38)
*H. sapiens;* MIMAT0000437

GUCCAGUUUUCCCAGGAAUCCCU (SEQ ID NO:4)

FIG. 7

5'-GUCCAGUUUUCCCAGGAAUCCCU-3' (SEQ ID NO:4) miR-145 mature miRNA

3'-uccCUAAGG----ACCcuuuUGACCUG-5' miR-145 (SEQ ID NO:4)
  5'-  uGAcUCCacaaUGGucccACUGGAC-3' Myocd 3'-UTR target "Site 1" (SEQ ID NO:5)
  3'-  ACTGAGGTGTTACCAGGGTGACCTG-5' target protector #1 (SEQ ID NO:6)

3'-uccCUA--AG---gaCCcuuUUGACCUG-5' miR-145 (SEQ ID NO:4)
  5'-  aGAUgaUCagaaaGGc---AACUGGAC-3' Myocd 3'-UTR target "Site 2" (SEQ ID NO:7)
  3'-  TCTACTAGTCTTTCCG--TTGACCTG-5' target protector #2 (SEQ ID NO:8)

target protector #1: 5'-GTCCAGTGGGACCATTGTGGAGTCA-3' (SEQ ID NO:6)
target protector #2: 5'-GTCCAGTTCCCTTTCTGATCATCT-3' (SEQ ID NO:8)

Figure 8A miR-143 sequences

```
1) Homo sapiens         GCCGAGCCCGCCUGUCUCCCAGCCUCAGUGUCAGUGCUGCAUCUCUGGUCAGUUG        (SEQ ID NO:1)
2) Mus musculus                             CCUGAGGUGCAGUGCUGCAUCUCUGGUCAGUUG        (SEQ ID NO:9)
3) Rattus norvegicus    GCCGAGGCCCUGUCUCCCAG--CCUGAGGUCAGUGCUGCAUCUCUGGUCAGUUG         (SEQ ID NO:10)
4) Macaca mulatta       GCCGAGCGCGUGUCUCCCAGCCUCAGUGUCAGUGCUGCUAUCUCUGGUCAGUUG         (SEQ ID NO:11)
5) Lagothrix lagotricha CGCCAGCGCGCCCCUGUCUCUCCCAGCCUGAGGUGCAGUGCUGCAUCUCUGGUCAGUUG    (SEQ ID NO:12)
6) Gorilla gorilla      GCGCAGCGCGCCCCUGUCUCCCAGCCUGAGGUGCAGUGCUGCAUCUCUGGGUCAGUUG     (SEQ ID NO:13)

1) Homo sapiens         CGAGUCUGAGAUGAAGCACUGUAGCUCAAGAAGAGAAGUUGUCUGCAGC              (SEQ ID NO:1)
2) Mus musculus         GGAGUCUGAGAUGAAGCACUGUAGCUCAGG                                 (SEQ ID NO:9)
3) Rattus norvegicus    GGAGUCUGAGAUGAAGCACUGUAGCUCAAGGAGAAGGGAGAAGAUGAUGUUCUGCAGC     (SEQ ID NO:10)
4) Macaca mulatta       GGAGUCUGAGAUGAAGCACUGUAGCUCAGGAAGAGAAGAAGUUGUUCUGCAGC          (SEQ ID NO:11)
5) Lagothrix lagotricha GGAGUCUGAGAUGAAGCACUGUAGCUCAAGGAAGAGAAGAAGUUGUCUGCAGC          (SEQ ID NO:12)
6) Gorilla gorilla      GGAGUCUGAGAUGAAGCACUGUAGCUCAAGGAAGAGAAGAAGUUGUUCUGCAGC         (SEQ ID NO:13)
```

Figure 8B miR-145 sequences

1) Homo sapiens          CACCUUGUCCUCACGGUCCAGUUUUCCCAGGAAUCCCUUAGAAUGCUAAGAUGG
2) Mus musculus          CUCACGGUCCAGUUUUCCCAGGAAUCCCUUGAUGCUAAGAUGG
3) Gorilla gorilla       CACCUUGUCCUCACGGUCCAGUUUCCCAGGAAUCCCUUAGAUGCUAAGAUGG
4) Rattus norvegicus     CACCUUGUCCUCACGGUCCAGUUUCCCAGGAAUCCCUUGAUGCUAAGAUGG
5) Macaca mulatta        CACCUUGUCCUCACGGUCCAGUUCCCAGGAAUCCCUUAAAUGCUAAGAUGG
6) Bos taurus            CACCUUGUCCUCACGGUCCAGUUCCCAGGAAUCCCUAAGAUGCUAAGAUGG 1) Homo sapiens          GGAUUCCUGGAAAUACUGUUCUUGAGGUCAUGGUU (SEQ ID NO:3)
2) Mus musculus          GGAUUCCUGGAAAUACUGUUCUUGAG          (SEQ ID NO:14)
3) Gorilla gorilla       GGAUUCCUGGAAAUACUGUUCUUGAGGUCAUGGUU (SEQ ID NO:15)
4) Rattus norvegicus     GGAUUCCUGGAAAUACUGUCUUGAGGUCAUGGCU  (SEQ ID NO:16)
5) Macaca mulatta        GGAUUCCUGGAAAUACUGUUCUUGAGGUCAUGGUU (SEQ ID NO:17)
6) Bos taurus            GGAUUCCUGGAAAUACUGUUCUUGAGGUCAUGGUU (SEQ ID NO:18)

a
SRF binding site
GGGAGCAGCCTTG(...)ATATA(...)GCAGGAGCCCC  mmu chr 18: 61812158
SRF^mut binding site
GGGAGCAGCCTTGCTA(...)AC(...)GCAGGAGCCCC
NKX2.5 binding site
GGGAAAGACTG(...)AAG(...)CTCGTGGCC  mmu chr 18: 61811308
NKX2.5^mut binding site
GGGAAAGACTG(...)(...)GA(...)CTCGTGGCC
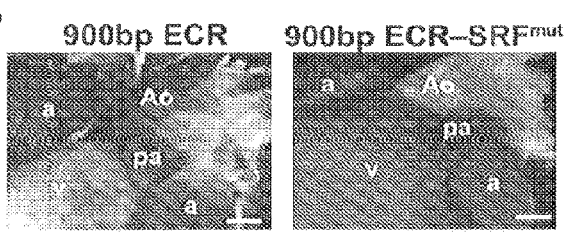
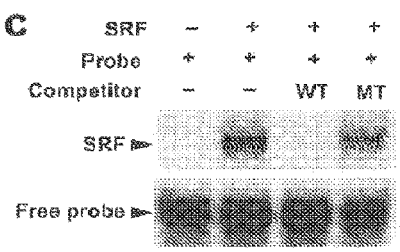
Figure 11

METHODS OF MODULATING SMOOTH MUSCLE CELL PROLIFERATION AND DIFFERENTIATION

CROSS-REFERENCE

This application claims the benefit of U.S. Provisional Patent Application No. 61/158,632, filed Mar. 9, 2009, which application is incorporated herein by reference in its entirety.

BACKGROUND

Vascular smooth muscle cells (VSMCs) are highly plastic and can oscillate between a proliferative or a quiescent, more differentiated state.

MicroRNAs (miRNAs) represent a class of small (20-25 nucleotides), non-coding RNAs that are key regulators of many cellular events, including the balance between proliferation and differentiation during tumorigenesis and organ development. miRNAs are initially transcribed as a longer primary transcript (pri-miRNA) and processed first by the ribonuclease enzyme complex, Drosha/DGCR8, and then by Dicer, leading to incorporation of a single strand into the RNA-induced silencing complex (RISC). Each of the 650 human miRNAs is predicted to interact with over one hundred target mRNAs in a sequence-specific fashion involving Watson-Crick base-pairing with nucleotides 2-8 of the miRNA. miRNAs generally inhibit target mRNAs by repressing translation or reducing mRNA stability. miRNAs may also activate mRNA translation under certain cellular conditions.

LITERATURE

US Patent Publication No. 2009/0226375; WO 2009/105759.

SUMMARY OF THE INVENTION

The present disclosure provides methods of inducing smooth muscle cell differentiation. The present disclosure provides genetically modified cells comprising exogenous miR-143 and/or miR-145 nucleic acids; and artificial tissues comprising the genetically modified cells. The present disclosure provides methods and compositions for reducing pathological angiogenesis. The present disclosure provides methods of inducing therapeutic angiogenesis. The present disclosure provides methods, compositions, and devices for inhibiting vascular smooth muscle cell proliferation.

BRIEF DESCRIPTION OF THE DRAWINGS

FIG. 4A depicts a miR-143 sequence (SEQ ID NO:2) that targets Elk-1 3'UTR Site 1 (SEQ ID NO:20); a miR-143 sequence (SEQ ID NO:19) that targets Elk-1 3'UTR Site 2 (SEQ ID NO:21); a miR-145 sequence (SEQ ID NO:4) that targets Myocd 3'UTR Site 1 (SEQ ID NO:5); and a miR-145 sequence (SEQ ID NO:22) that targets a Myocd 3'UTR Site 2 (SEQ ID NO:7). FIG. 4G depicts a miR-145 sequence (SEQ ID NO:4) that targets a Klf4 3'UTR sequence (SEQ ID NO:62). FIG. 4J depicts a miR-145 sequence (SEQ ID NO:4) that targets a CamkII-δ 3'UTR sequence (SEQ ID NO:22).

FIG. 6A depicts miR-143 nucleic acids.

FIG. 6B depicts miR-145 nucleic acids.

FIG. 7 depicts miR-145 nucleic acid, Myocd 3'-UTR target sites, and target protector nucleic acids.

FIGS. 8A and 8B provide an alignment of miR-143 precursor nucleic acids and miR-154 nucleic acids, respectively, of various species.

FIG. 9A depicts mature miR-143 sequences from human (SEQ ID NO:23); mouse (SEQ ID NO:24); rat (SEQ ID NO:25); chicken (SEQ ID NO:26); and zebrafish (SEQ ID NO:27). FIG. 9A also depicts mature miR-145 sequences from human (SEQ ID NO:28); mouse (SEQ ID NO:29); rat (SEQ ID NO:30); chicken (SEQ ID NO:31); zebrafish (SEQ ID NO:32); and *Drosophila* (SEQ ID NO:33).

FIGS. 11A-C depict: Putative SRF and Nkx2.5 binding sites within the 900 bp cis-regulatory element of miR-143 and miR-145 (FIG. 11A); LacZ expression of the 900 by cis-acting regulatory element was present in the smooth muscle of the aorta, but a mutation of the SRF binding site eliminated enhancer activity (FIG. 11B); and electrophoretic mobility-shift assay (EMSA) using radiolabeled probe for the SRF binding site (FIG. 11C). FIG. 11A depicts an SFR binding site (SEQ ID NO:34); a mutated SFR binding site (SEQ ID NO:35); an NKX2.5 binding site (SEQ ID NO:36); and a mutated NKX2.5 binding site (SEQ ID NO:37).

FIG. 14A depicts a mapk7 predicted binding site (SEQ ID NO:38); and a nestin predicted binding site (SEQ ID NO:39). FIG. 14B depicts two Camk1δ target scan binding sites (SEQ ID NOs:40 and 41); a Ctnnbip predicted binding site (SEQ ID NO:42); a Hes2 predicted binding site (SEQ ID NO:43); and two Sox11 predicted binding sites (SEQ ID NOs:44 and 45).

DEFINITIONS

Figure 1:
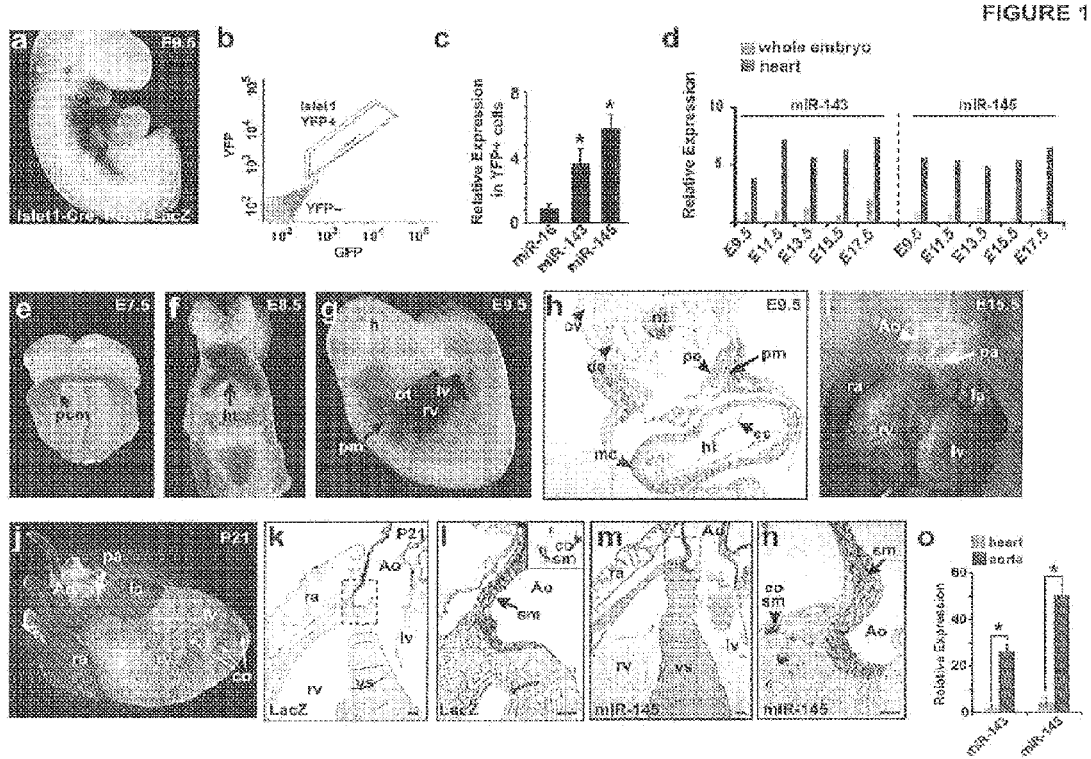
FIGS. 1A-O depict miR-143 and miR-145 in cardiac and smooth muscle cells.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as, Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179, which are incorporated herein by reference. Examples of microRNAs include any RNA that is a fragment of a larger RNA or is a miRNA, siRNA, stRNA, sncRNA, tncRNA, snoRNA, smRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

A "stem-loop structure" refers to a nucleic acid having a secondary structure that includes a region of nucleotides which are known or predicted to form a double strand (step portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5 x SSC (150 mM NaCl, 15 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense polynucleotide which is 18 nucleotides in length having 4 (four) noncomplementary nucleotides which are flanked by two regions of complete complementarity with the target nucleic acid would have 77.8% overall complementarity with the target nucleic acid. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. *Mol. Biol.* 48: 443-453 (1970).

As used herein, the term "stem cell" refers to an undifferentiated cell that can be induced to proliferate. The stem cell is capable of self-maintenance, meaning that with each cell division, one daughter cell will also be a stem cell. Stem cells can be obtained from embryonic, fetal, post-natal, juvenile or adult tissue. The term "progenitor cell", as used herein, refers to an undifferentiated cell derived from a stem cell, and is not itself a stem cell. Some progenitor cells can produce progeny that are capable of differentiating into more than one cell type.

The term "induced pluripotent stem cell" (or "iPS cell"), as used herein, refers to a stem cell induced from a somatic cell, e.g., a differentiated somatic cell, and that has a higher potency than said somatic cell. iPS cells are capable of self-renewal and differentiation into mature cells, e.g., smooth muscle cells. iPS may also be capable of differentiation into smooth muscle progenitor cells.

As used herein the term "isolated" with reference to a cell, refers to a cell that is in an environment different from that in which the cell naturally occurs, e.g., where the cell naturally occurs in a multicellular organism, and the cell is removed from the multicellular organism, the cell is "isolated." An isolated genetically modified host cell can be present in a mixed population of genetically modified host cells, or in a mixed population comprising genetically modified host cells and host cells that are not genetically modified. For example, an isolated genetically modified host cell can be present in a mixed population of genetically modified host cells in vitro, or in a mixed in vitro population comprising genetically modified host cells and host cells that are not genetically modified.

A "host cell," as used herein, denotes an in vivo or in vitro cell (e.g., a eukaryotic cell cultured as a unicellular entity), which eukaryotic cell can be, or has been, used as recipients for a nucleic acid (e.g., an exogenous nucleic acid), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation.

The term "genetic modification" and refers to a permanent or transient genetic change induced in a cell following introduction of new nucleic acid (i.e., nucleic acid exogenous to the cell). Genetic change ("modification") can be accomplished by incorporation of the new nucleic acid into the genome of the host cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

As used herein, the term "exogenous nucleic acid" refers to a nucleic acid that is not normally or naturally found in and/or produced by a cell in nature, and/or that is introduced into the cell (e.g., by electroporation, transfection, infection, lipofection, or any other means of introducing a nucleic acid into a cell).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, a human, a non-human primate, a rodent (e.g., a mouse, a rat, etc.), an ungulate, a canine, a lagomorph, a feline, etc. In some embodiments, a subject of interest is a human. In some embodiments, a subject is a non-human animal such as a rodent, or a lagomorph.

A "therapeutically effective amount" or "efficacious amount" means the amount of a compound, a nucleic acid, or a number of cells that, when administered to a subject for treating a disease, is sufficient to effect such treatment for the disease. The "therapeutically effective amount" will vary depending on the compound or the cell, the disease and its severity and the age, weight, etc., of the subject to be treated.

"Vascular remodeling" refers to a diminution in vessel lumen volume, diameter or area that is not the result of neointimal thickening or smooth muscle cell proliferation, and which generally occurs after a procedural vascular trauma. Thus, a reduction in the area ("constriction") circumscribed by the internal elastic lamina or membrane (IEL) without significant amounts of neointimal formation is termed "vascular remodeling." See Isner, Circ. 89:2937 (1994). The luminal cross-sectional area of a vessel can be measured by direct planimetering, e.g., by intravascular ultrasound (IVUS) or at necropsy. As used herein, "vascular remodeling" does not include compensatory enlargement of a vessel which accompanies neointimal proliferation so as to accommodate the intimal increase. This compensatory enlargement has also been referred to as "positive" vascular remodeling.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a miR-145 nucleic acid" includes a plurality of such nucleic acids and reference to "the vascular smooth muscle cell" includes reference to one or more vascular smooth muscle cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of inducing smooth muscle cell differentiation. The present disclosure provides genetically modified cells comprising exogenous miR-143 and/or miR-145 nucleic acids; and artificial tissues. The present disclosure provides methods and compositions for reducing pathological angiogenesis. The present disclosure provides methods of inducing therapeutic angiogenesis. The present disclosure provides methods, compositions, and devices for inhibiting vascular smooth muscle cell proliferation.

A subject method of inducing smooth muscle cell differentiation generally involves introducing into a stem cell or a progenitor cell a miR-143 nucleic acid and/or a miR-145 nucleic acid, or at least one nucleic acid comprising nucleotide sequences encoding a miR-143 nucleic acid and/or a miR-145 nucleic acid. As described in more detail below, induction of smooth muscle cell differentiation is useful in the context of generating smooth muscles from stem cells or progenitor cells, and can be used, e.g., to generate vascular smooth muscle cells (VSMC) in vitro or in vivo. Generation of VSMC is useful for generation of new blood vessels and/or repair of existing blood vessels. The present disclosure further provides genetically modified host cells, e.g., genetically modified stem or progenitor cells that are genetically modified with exogenous miR-143 and/or miR-145 nucleic acid, or at least one exogenous nucleic acid comprising nucleotide sequences encoding miR-143 nucleic acid and/or miR-145 nucleic acid. The present disclosure also provides an artificial blood vessel, the artificial blood vessel comprising a subject genetically modified host cell or a VSMC derived from a subject genetically modified host cell.

The present disclosure provides methods of reducing pathological angiogenesis, the methods generally involving introducing into a VSMC, or a VSMC precursor, a nucleic acid comprising a nucleotide sequence encoding a nucleic acid that reduces the level of a miR-143 nucleic acid and/or a miR-145 nucleic acid in the VSMC or the VSMC precursor; or introducing into a VSMC, or a VSMC precursor a target protector nucleic acid that reduces the effect of miR-145 on target Myocd nucleic acid. The present disclosure further provides nucleic acids for use in a subject method of reducing pathological angiogenesis, where such nucleic acids include antisense nucleic acids and target protector nucleic acids. A subject method of reducing pathological angiogenesis is useful for reducing tumor growth, e.g., reducing production of blood vessels that support tumor growth.

The present disclosure further provides methods of increasing therapeutic angiogenesis, the methods generally involving administering to a subject in need thereof an effective amount of a miR-143 nucleic acid and/or a miR-145 nucleic acid, or at least one nucleic acid comprising nucleotide sequences encoding a miR-143 nucleic acid and/or a miR-145 nucleic acid. The nucleic acid enters a VSMC or a VSMC precursor, and induces production of new blood vessels. A subject method of increasing therapeutic angiogenesis is useful for treating ischemic disorders or other disorders that benefit from increased blood flow. Ischemic disorders include, e.g., cardiac ischemia, limb ischemia, and the like.

The present disclosure further provides methods for reducing VSMC proliferation. A subject method of reducing VSMC proliferation generally involves introducing into a VSMC a miR-143 nucleic acid and/or a miR-145 nucleic acid, or at least one nucleic acid comprising nucleotide sequences encoding a miR-143 nucleic acid and/or a miR-145 nucleic acid. Methods of reducing VSMC are useful, e.g., in the context of vascular injury or in the context of vascular disease. Thus, the present disclosure provides methods of reducing VSMC proliferation in a mammalian blood vessel following injury; and methods of reducing VSMC proliferation in a mammalian blood vessel associated with disease (e.g., atherosclerosis).

The present disclosure further provides compositions and devices for reducing VSMC proliferation, e.g., in the context of vascular injury or disease. A subject device comprises a composition coated thereon or impregnated therein, which composition comprises a VSMC a miR-143 nucleic acid and/ or a miR-145 nucleic acid, or at least one nucleic acid comprising nucleotide sequences encoding a miR-143 nucleic acid and/or a miR-145 nucleic acid.

Methods of Inducing Smooth Muscle Cell Differentiation

The present disclosure provides methods of inducing smooth muscle cell differentiation. The methods generally involve introducing into a stem cell or progenitor cell a miR-143 nucleic acid and/or a miR-145 nucleic acid, or at least one nucleic acid comprising nucleotide sequences encoding a miR-143 nucleic acid and/or a miR-145 nucleic acid.

In some embodiments, a subject method provides for differentiation of a stem cell or progenitor cell, or a population of stem cells or progenitor cells, into a smooth muscle cell(s). In some of these embodiments, a subject method involves introducing into a stem or progenitor cell a miR-143 nucleic acid and/or a miR-145 nucleic acid, or at least one nucleic acid comprising nucleotide sequences encoding a miR-143 nucleic acid and/or a miR-145 nucleic acid. In some embodiments, a subject method involves introducing into a stem or progenitor cell a miR-145 nucleic acid, or a nucleic acid comprising a nucleotide sequence encoding a miR-145 nucleic acid. In other embodiments, a subject method involves introducing into a stem or progenitor cell a miR-143 nucleic acid and a miR-145 nucleic acid, or a nucleic acid(s) comprising nucleotide sequences encoding a miR-143 nucleic acid and a miR-145 nucleic acid. In some embodiments, a suitable miR-143 or miR-145 nucleic acid comprises a stem-loop forming ("precursor") nucleotide sequence. In other embodiments, a suitable miR-144 or miR-145 nucleic acid comprises a mature form of a miR-143 or a miR-145 nucleic acid.

In some embodiments, introduction of a miR-145 nucleic acid, or a miR-145-encoding nucleic acid (e.g., a nucleic acid comprising a nucleotide sequence encoding a miR-145 nucleic acid), into a stem cell or progenitor cell (such that the stem cell or progenitor cell is genetically modified with the nucleic acid) results in increased levels of Myocd polypeptide in the cell. For example, introduction of a miR-145 nucleic acid, or a miR-145-encoding nucleic acid (e.g., a nucleic acid comprising a nucleotide sequence encoding a miR-145 nucleic acid), into a stem cell or progenitor cell (such that the stem cell or progenitor cell is genetically modified with the nucleic acid) results in an increase of from about 2-fold to about 4-fold, from about 4-fold to about 5-fold, from about 5-fold to about 10-fold, from about 10-fold to about 15-fold, from about 15-fold to about 20-fold, from about 20-fold to about 25-fold, from about 25-fold to about 30-fold, from about 30-fold to about 35-fold, or from about 35-fold to about 40-fold, in the level of Myocd polypeptide in the cell, compared to the level of Myocd polypeptide in a control cell not genetically modified with the nucleic acid.

In some embodiments, introduction of a miR-143 nucleic acid, or a miR-143-encoding nucleic acid (e.g., a nucleic acid comprising a nucleotide sequence encoding a miR-143 nucleic acid), into a stem cell or progenitor cell (such that the stem cell or progenitor cell is genetically modified with the nucleic acid) results in a decrease in the level of an Elk-1 polypeptide in the cell. For example, introduction of a miR-143 nucleic acid, or a miR-143-encoding nucleic acid (e.g., a nucleic acid comprising a nucleotide sequence encoding a miR-143 nucleic acid), into a stem cell or progenitor cell (such that the stem cell or progenitor cell is genetically modified with the nucleic acid) results in a decrease of from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 60%, from about 60% to about 70%, from about 70% to about 80%, or more than 80%, compared to the level of Elk-1 polypeptide in a control cell not genetically modified with the nucleic acid.

In some embodiments, introduction of a miR-145 nucleic acid, or a miR-145-encoding nucleic acid (e.g., a nucleic acid comprising a nucleotide sequence encoding a miR-145 nucleic acid), into a stem cell or progenitor cell (such that the stem cell or progenitor cell is genetically modified with the nucleic acid) results in differentiation of the stem or progenitor cell into a smooth muscle cell, e.g., a vascular smooth muscle cell. In some embodiments, introduction of a miR-145 nucleic acid, or a miR-145-encoding nucleic acid (e.g., a nucleic acid comprising a nucleotide sequence encoding a miR-145 nucleic acid), into a stem cell or progenitor cell (such that the stem cell or progenitor cell is genetically modified with the nucleic acid) results in generation of a vascular smooth muscle cell that expresses one or more VSMC differentiation markers. VSMC differentiation markers include, e.g., alpha-smooth muscle actin (α-SMA), smooth muscle-22alpha (SM-22α), and smooth muscle myosin heavy chain (sm-MHC). Whether a cell expresses one or more VSMC differentiation markers is readily determined using known methods. For example, levels of mRNA encoding a VSCM differentiation marker can readily be determined using, e.g, a quantitative polymerase chain reaction. Levels of VSCM differentiation marker polypeptides can be determined using immunological assays employing antibody specific for a VSCM differentiation marker polypeptide, e.g., where the antibody is detectably labeled.

In some embodiments, introduction of a miR-143 nucleic acid and/or a miR-145 nucleic acid, or at least one nucleic acid comprising nucleotide sequences encoding a miR-143 nucleic acid and/or a miR-145 nucleic acid, into a stem cell or progenitor cell results in an increase in the number of VSMCs. For example, introduction of a miR-143 nucleic acid and/or a miR-145 nucleic acid, or at least one nucleic acid comprising nucleotide sequences encoding a miR-143 nucleic acid and/or a miR-145 nucleic acid into a stem cell or progenitor cell results in an increase of from about 2-fold to about 5-fold, from about 5-fold to about 10-fold, from about 10-fold to about 25-fold, from about 25-fold to about 50-fold, from about 50-fold to about 100-fold, from about $10^2$-fold to about $5 \times 10^2$-fold, from about $5 \times 10^2$-fold to about $10^3$-fold, from about $10^3$-fold to about $10^4$-fold, or greater than $10^4$-fold, in the number of VSMCs.

In some embodiments, a miR-143 nucleic acid and/or a miR-145 nucleic acid, or at least one nucleic acid comprising nucleotide sequences encoding a miR-143 nucleic acid and/ or a miR-145 nucleic acid, is introduced into a population of cells that comprises stem cells and/or progenitor cells; and, as a result, the proportion of cells in the population that are VSMCs or VSMC progenitors increases. For example, in some embodiments, introduction of a miR-143 nucleic acid and/or a miR-145 nucleic acid, or at least one nucleic acid comprising nucleotide sequences encoding a miR-143 nucleic acid and/or a miR-145 nucleic acid, into a cell population that comprises stem cells or progenitor cells results in differentiation of at least about 10% of the stem cell or progenitor cell population into VSMCs or VSMC progenitors. For example, in some embodiments, from about 10% to about 50% of the stem cell or progenitor cell population differentiates into VSMCs or VSMC progenitors. In other embodiments, at least about 50% of the stem cell or progenitor cell population differentiates into VSMCs or VSMC progenitors. For example, in some embodiments, from about 50% to about 60%, from about 60% to about 70%, from about 70% to about 80%, or from about 80% to about 90%, or more, of the stem cell or progenitor cell population differentiates into VSMCs or VSMC progenitors.

Stem Cells and Progenitor Cells

Suitable stem cells include embryonic stem cells, neural crest stem cells, adult stem cells, and induced pluripotent stem (iPS) cells.

In some embodiments, an immortalized neural crest cell line is employed.

In some embodiments, an iPS cell is used. iPS cells are generated from mammalian cells (including mammalian somatic cells) using, e.g., known methods. Examples of suitable mammalian cells include, but are not limited to: fibroblasts, skin fibroblasts, dermal fibroblasts, bone marrow-derived mononuclear cells, skeletal muscle cells, adipose cells, peripheral blood mononuclear cells, macrophages, hepatocytes, keratinocytes, oral keratinocytes, hair follicle dermal cells, epithelial cells, gastric epithelial cells, lung epithelial cells, synovial cells, kidney cells, skin epithelial cells, pancreatic beta cells, and osteoblasts.

Mammalian cells used to generate iPS cells can originate from a variety of types of tissue including but not limited to: bone marrow, skin (e.g., dermis, epidermis), muscle, adipose tissue, peripheral blood, foreskin, skeletal muscle, and smooth muscle. The cells used to generate iPS cells can also be derived from neonatal tissue, including, but not limited to: umbilical cord tissues (e.g., the umbilical cord, cord blood, cord blood vessels), the amnion, the placenta, and various other neonatal tissues (e.g., bone marrow fluid, muscle, adipose tissue, peripheral blood, skin, skeletal muscle etc.).

Cells used to generate iPS cells can be derived from tissue of a non-embryonic subject, a neonatal infant, a child, or an adult. Cells used to generate iPS cells can be derived from neonatal or post-natal tissue collected from a subject within the period from birth, including cesarean birth, to death. For example, the tissue source of cells used to generate iPS cells can be from a subject who is greater than about 10 minutes old, greater than about 1 hour old, greater than about 1 day old, greater than about 1 month old, greater than about 2 months old, greater than about 6 months old, greater than about 1 year old, greater than about 2 years old, greater than about 5 years old, greater than about 10 years old, greater than about 15 years old, greater than about 18 years old, greater than about 25 years old, greater than about 35 years old, >45 years old, >55 years old, >65 years old, >80 years old, <80 years old, <70 years old, <60 years old, <50 years old, <40 years old, <30 years old, <20 years old or <10 years old.

iPS cells produce and express on their cell surface one or more of the following cell surface antigens: SSEA-3, SSEA-4, TRA-1-60, TRA-1-81, TRA-2-49/6E (alkaline phophatase), and Nanog. In some embodiments, iPS cells produce and express on their cell surface SSEA-3, SSEA-4, TRA-1-60, TRA-1-81, TRA-2-49/6E, and Nanog. iPS cells express one or more of the following genes: Oct-3/4, Sox2, Nanog, GDF3, REX1, FGF4, ESG1, DPPA2, DPPA4, and hTERT. In some embodiments, an iPS cell expresses Oct-3/4, Sox2, Nanog, GDF3, REX1, FGF4, ESG1, DPPA2, DPPA4, and hTERT.

Methods of generating iPS cells are known in the art, and a wide range of methods can be used to generate iPS cells. See, e.g., Takahashi and Yamanaka (2006) Cell 126:663-676; Yamanaka et al. (2007) Nature 448:313-7; Wernig et al. (2007) Nature 448:318-24; Maherali (2007) Cell Stem Cell 1:55-70; Maherali and Hochedlinger (2008) Cell Stem Cell 3:595-605; Park et al. (2008) Cell 134:1-10; Dimos et. al. (2008) Science 321:1218-1221; Blelloch et al. (2007) Cell Stem Cell 1:245-247; Stadtfeld et al. (2008) Science 322:945-949; Stadtfeld et al. (2008) 2:230-240; Okita et al. (2008) Science 322:949-953.

In some embodiments, iPS cells are generated from somatic cells by forcing expression of a set of factors in order to promote increased potency of a cell or to promote de-differentiation. Forcing expression can include introducing expression vectors encoding polypeptides of interest into cells, introducing exogenous purified polypeptides of interest into cells, or contacting cells with a reagent that induces expression of an endogenous gene encoding a polypeptide of interest.

Forcing expression may include introducing expression vectors into somatic cells via use of moloney-based retroviruses (e.g., MLV), lentiviruses (e.g., HIV), adenoviruses, protein transduction, transient transfection, or protein transduction. In some embodiments, the moloney-based retroviruses or HIV-based lentiviruses are pseudotyped with envelope from another virus, e.g. vesicular stomatitis virus g (VSV-g) using known methods in the art. See, e.g. Dimos et al. (2008) Science 321:1218-1221.

In some embodiments, iPS cells are generated from somatic cells by forcing expression of Oct-3/4 and Sox2 polypeptides. In some embodiments, iPS cells are generated from somatic cells by forcing expression of Oct-3/4, Sox2 and Klf4 polypeptides. In some embodiments, iPS cells are generated from somatic cells by forcing expression of Oct-3/4, Sox2, Klf4 and c-Myc polypeptides. In some embodiments, iPS cells are generated from somatic cells by forcing expression of Oct-4, Sox2, Nanog, and LIN28 polypeptides.

For example, iPS cells can be generated from somatic cells by genetically modifying the somatic cells with one or more expression constructs encoding Oct-3/4 and Sox2. As another example, iPS cells can be generated from somatic cells by genetically modifying the somatic cells with one or more expression constructs comprising nucleotide sequences encoding Oct-3/4, Sox2, c-myc, and Klf4. As another example, iPS cells can be generated from somatic cells by genetically modifying the somatic cells with one or more expression constructs comprising nucleotide sequences encoding Oct-4, Sox2, Nanog, and LIN28.

In some embodiments, cells undergoing induction of pluripotency as described above, to generate iPS cells, are contacted with additional factors which can be added to the culture system, e.g.., included as additives in the culture medium. Examples of such additional factors include, but are not limited to: histone deacetylase (HDAC) inhibitors, see, e.g. Huangfu et al. (2008) Nature Biotechnol. 26:795-797; Huangfu et al. (2008) Nature Biotechnol. 26: 1269-1275; DNA demethylating agents, see, e.g., Mikkelson et al (2008) Nature 454, 49-55; histone methyltransferase inhibitors, see, e.g., Shi et al. (2008) Cell Stem Cell 2:525-528; L-type calcium channel agonists, see, e.g., Shi et al. (2008) 3:568-574;

Wnt3a, see, e.g., Marson et al. (2008) Cell 134:521-533; and siRNA, see, e.g., Zhao et al. (2008) Cell Stem Cell 3: 475-479.

In some embodiments, iPS cells are generated from somatic cells by forcing expression of Oct3/4, Sox2 and contacting the cells with an HDAC inhibitor, e.g., valproic acid. See, e.g., Huangfu et al. (2008) Nature Biotechnol. 26: 1269-1275. In some embodiments, iPS cells are generated from somatic cells by forcing expression of Oct3/4, Sox2, and Klf4 and contacting the cells with an HDAC inhibitor, e.g., valproic acid. See, e.g., Huangfu et al. (2008) Nature Biotechnol. 26:795-797.

In some embodiments, a subject method comprises: a) inducing a somatic cell from an individual to become a pluripotent stem cell, generating an iPS cell; b) introducing a miR-145 nucleic acid (or a nucleic acid comprising a nucleotide sequence encoding a miR-145 nucleic acid) into the iPS cell, generating VSMCs. Such VSMCs would be useful for introducing into the individual from whom the somatic cell was obtained. For example, in some embodiments, a somatic cell is obtained from a donor individual; an iPS cell is generated from the somatic cell; the iPS cell is induced to differentiate into a VSMC; and the VSMC is introduced into the donor individual from whom the somatic cell was obtained. Such VSMCs could also be introduced into an individual other than the individual from whom the somatic cell was obtained. For example, in some embodiments, a somatic cell is obtained from a donor individual; an iPS cell is generated from the somatic cell; the iPS cell is induced to differentiate into a VSMC; and the VSMC is introduced into a recipient individual, where the recipient individual is not the same individual as the donor individual.

miR-143 Nucleic Acid miR-143 nucleic acids are known in the art. In some embodiments, a suitable miR-143 nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence set forth in SEQ ID NO:1 and depicted in FIG. 6A. In some embodiments, a suitable miR-143 nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence set forth in SEQ ID NO:2 and depicted in FIG. 6A.

In some embodiments, a suitable nucleic acid comprises a nucleotide sequence encoding a miR-143 nucleic acid. As such, in some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:1 and depicted in FIG. 6A.

In some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:2 and depicted in FIG. 6A. In some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:2 and depicted in FIG. 6A, where the portion of the nucleotide sequence that has at least about 75%, at least about 80%, at least about 85%, at least about 90%, at least about 95%, at least about 98%, at least about 99%, or 100%, nucleotide sequence identity to the nucleotide sequence set forth in SEQ ID NO:2 has a length of 18 nucleotides (nt), 19 nt, 20 nt, 21 nt, 22 nt, 23 nt, 24 nt, or 25 nt. In some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:2 and depicted in FIG. 6A, and has a length of 18 nt, 19 nt, 20 nt, 21 nt, 22 nt, 23 nt, 24 nt, or 25 nt.

In some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:2 and depicted in FIG. 6A, where the portion of the nucleotide sequence that has at least about 75%, at least about 80%, at least about 85%, at least about 90%, at least about 95%, at least about 98%, at least about 99%, or 100%, nucleotide sequence identity to the nucleotide sequence set forth in SEQ ID NO:2 has a length of 18 nt, 19 nt, 20 nt, 21 nt, 22 nt, 23 nt, 24 nt, or 25 nt, and where the nucleic acid comprising the nucleotide sequence encoding the miR-143 nucleic acid can have, in addition to the 18 nt, 19 nt, 20 nt, 21 nt, 22 nt, 23 nt, 24 nt, encoding the miR-143 nucleic acid, additional nucleotides 5' and/or 3' of the miR-143-encoding sequence. Thus, e.g., a nucleic acid can comprise, in addition to the 18 nt, 19 nt, 20 nt, 21 nt, 22 nt, 23 nt, 24 nt, or 25 nt encoding the miR-143 nucleic acid, additional nucleotides 5' and/or 3' of the miR-143-encoding sequence, where the additional nucleotides can be from 1 nt to 10 nt, from 10 nt to 100 nt, from 100 nt to 500 nt, from 500 nt to 1 kb, or from 1 kb to about 5 kb, from about 5 kb to about 10 kb, or more than 10 kb, such that the total length of the nucleic acid can be from about 18 nt to about 10 kb or more.

In some embodiments, a miR-143-encoding nucleic acid is contained within an expression vector. In some embodiments, a nucleotide sequence encoding a miR-143 nucleic acid is operably linked to a transcriptional regulatory element, e.g., a promoter, an enhancer, etc.

miR-145 Nucleic Acid miR-145 nucleic acids are known in the art. In some embodiments, a suitable miR-145 nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence set forth in SEQ ID NO:3 and depicted in FIG. 6B. In some embodiments, a suitable miR-145 nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence set forth in SEQ ID NO:4 and depicted in FIG. 6B.

In some embodiments, a suitable nucleic acid comprises a nucleotide sequence encoding a miR-145 nucleic acid. As such, in some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:3 and depicted in FIG. 6B.

In some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:4 and depicted in FIG. 6B. In some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:4 and depicted in FIG. 6B, where the portion of the nucleotide sequence that has at least about 75%, at least about 80%, at least about 85%, at least about 90%, at least about 95%, at least about 98%, at least about 99%, or 100%, nucleotide sequence identity to the nucleotide sequence set forth in SEQ ID NO:4 has a length of 18 nucleotides (nt), 19 nt, 20 nt, 21 nt, 22 nt, 23 nt, 24 nt, or 25 nt. In some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:4 and depicted in FIG. 6B, and has a length of 18 nt, 19 nt, 20 nt, 21 nt, 22 nt, 23 nt, 24 nt, or 25 nt.

In some embodiments, a suitable nucleic acid comprises a nucleotide sequence encoding a nucleic acid having at least about 75%, at least about 80%, at least about 85%, at least about 90%, at least about 95%, at least about 98%, at least about 99%, or 100%, nucleotide sequence identity to the nucleotide sequence set forth in SEQ ID NO:4 and depicted in FIG. 6B, where the portion of the nucleotide sequence that has at least about 75%, at least about 80%, at least about 85%, at least about 90%, at least about 95%, at least about 98%, at least about 99%, or 100%, nucleotide sequence identity to the nucleotide sequence set forth in SEQ ID NO:2 has a length of 18 nt, 19 nt, 20 nt, 21 nt, 22 nt, 23 nt, 24 nt, or 25 nt, and where the nucleic acid comprising the nucleotide sequence encoding the miR-145 nucleic acid can have, in addition to the 18 nt, 19 nt, 20 nt, 21 nt, 22 nt, 23 nt, 24 nt, encoding the miR-145 nucleic acid, additional nucleotides 5' and/or 3' of the miR-145-encoding sequence. Thus, e.g., a nucleic acid can comprise, in addition to the 18 nt, 19 nt, 20 nt, 21 nt, 22 nt, 23 nt, 24 nt, or 25 nt encoding the miR-145 nucleic acid, additional nucleotides 5' and/or 3' of the miR-145-encoding sequence, where the additional nucleotides can be from 1 nt to 10 nt, from 10 nt to 100 nt, from 100 nt to 500 nt, from 500 nt to 1 kb, or from 1 kb to about 5 kb, from about 5 kb to about 10 kb, or more than 10 kb, such that the total length of the nucleic acid can be from about 18 nt to about 10 kb or more.

In some embodiments, a miR-145-encoding nucleic acid is contained within an expression vector. In some embodiments, a nucleotide sequence encoding a miR-145 nucleic acid is operably linked to a transcriptional regulatory element, e.g., a promoter, an enhancer, etc.

Expression Vectors and Control Elements

As noted above, in some embodiments, a subject method involves introducing into a stem cell or a progenitor cell (or a population of stem cells or progenitor cells) a miR-143-encoding nucleic acid and/or an miR-145-encoding nucleic acid. In some embodiments, a subject method involves introducing into a stem cell or a progenitor cell (or a population of stem cells or progenitor cells) a nucleic acid comprising a nucleotide sequence encoding a miR-145 nucleic acid. In some embodiments, a subject method involves introducing into a stem cell or a progenitor cell (or a population of stem cells or progenitor cells) one or more nucleic acids comprising nucleotide sequences encoding miR-143 and miR-145. Suitable nucleic acids comprising miR-143-encoding and/or miR-145-encoding nucleotide sequences include expression vectors ("expression constructs"), where an expression vector comprising a miR-143-encoding and/or a miR-145-encoding nucleotide sequence is a "recombinant expression vector."

In some embodiments, the expression construct is a viral construct, e.g., a recombinant adeno-associated virus construct (see, e.g., U.S. Pat. No. 7,078,387), a recombinant adenoviral construct, a recombinant lentiviral construct, etc.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like.

Numerous suitable expression vectors are known to those of skill in the art, and many are commercially available. The following vectors are provided by way of example; for eukaryotic host cells: pXT1, pSG5 (Stratagene), pSVK3, pBPV, pMSG, and pSVLSV40 (Pharmacia). However, any other vector may be used so long as it is compatible with the host cell.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology*, 153:516-544).

In some embodiments, a miR-145-encoding nucleotide sequence is operably linked to a control element, e.g., a transcriptional control element, such as a promoter. Likewise, in some embodiments, a miR-143-encoding nucleotide sequence is operably linked to a control element, e.g., a transcriptional control element, such as a promoter. The transcriptional control element is functional in a eukaryotic cell, e.g., a mammalian cell.

Non-limiting examples of suitable eukaryotic promoters (promoters functional in a eukaryotic cell) include those from cytomegalovirus (CMV) immediate early, herpes simplex virus (HSV) thymidine kinase, early and late SV40, long terminal repeats (LTRs) from retrovirus, and mouse metallothionein-I. Selection of the appropriate vector and promoter is well within the level of ordinary skill in the art. The expression vector may also contain a ribosome binding site for translation initiation and a transcription terminator. The expression vector may also include appropriate sequences for amplifying expression.

In some embodiments, the miR-143-encoding nucleotide sequence and/or the miR-145-encoding nucleotide sequence is operably linked to a smooth muscle cell-specific promoter. Smooth muscle cell-specific promoters include, e.g., a SM22a promoter (see, e.g., Akyürek et al. (2000) *Mol. Med.* 6:983; and U.S. Pat. No. 7,169,874); a smoothelin promoter (see, e.g., WO 2001/018048); an α-smooth muscle actin promoter; etc. For example, a 0.4 kb region of the SM22a promoter, within which lie two CArG elements, has been shown to mediate vascular smooth muscle cell-specific expression (see, e.g., Kim, et al. (1997) Mol. Cell. Biol. 17, 2266-2278; Li, et al., (1996) J. Cell Biol. 132, 849-859; and Moessler, et al. (1996) Development 122, 2415-2425).

In some embodiments, the miR-143-encoding nucleotide sequence and/or the miR-145-encoding nucleotide sequence is operably linked to a cardiac-specific transcriptional regulator element (TRE), where TREs include promoters and enhancers. Suitable TREs include, but are not limited to, TREs derived from the following genes: myosin light chain-2, α-myosin heavy chain, AE3, cardiac troponin C, and cardiac actin. Franz et al. (1997) Cardiovasc. Res. 35:560-566; Robbins et al. (1995) Ann. N.Y. Acad. Sci. 752:492-505; Linn et al. (1995) Circ. Res. 76:584-591; Parmacek et al. (1994) Mol. Cell. Biol. 14:1870-1885; Hunter et al. (1993) Hypertension 22:608-617; and Sartorelli et al. (1992) Proc. Natl. Acad. Sci. USA 89:4047-4051.

In some embodiments, the miR-143-encoding nucleotide sequence and/or the miR-145-encoding nucleotide sequence is operably linked to an inducible promoter. In some embodiments, the miR-143-encoding nucleotide sequence and/or the miR-145-encoding nucleotide sequence is operably linked to a constitutive promoter.

Methods of introducing a nucleic acid into a host cell are known in the art, and any known method can be used to introduce a nucleic acid (e.g., an expression construct) into a stem cell or progenitor cell. Suitable methods include, e.g., infection, lipofection, electroporation, calcium phosphate precipitation, DEAE-dextran mediated transfection, liposome-mediated transfection, and the like.

Genetically Modified Host Cells

The present disclosure provides genetically modified host cells, including isolated genetically modified host cells, where a subject genetically modified host cell comprises (has been genetically modified with): 1) an exogenous miR-143 nucleic acid; 2) an exogenous miR-145 nucleic acid; 3) both exogenous miR-143 nucleic acid and exogenous miR-145 nucleic acid; 4) an exogenous nucleic acid comprising a nucleotide sequence encoding a miR-143 nucleic acid; 5) an exogenous nucleic acid comprising a nucleotide sequence encoding a miR-145 nucleic acid; or 6) one or more exogenous nucleic acids comprising nucleotide sequences encoding both a miR-143 nucleic acid and a miR-145 nucleic acid. A subject genetically modified cell is generated by genetically modifying a host cell one or more exogenous nucleic acids (e.g., 1) an exogenous miR-143 nucleic acid; 2) an exogenous miR-145 nucleic acid; 3) both exogenous miR-143 nucleic acid and exogenous miR-145 nucleic acid; 4) an exogenous nucleic acid comprising a nucleotide sequence encoding a miR-143 nucleic acid; 5) an exogenous nucleic acid comprising a nucleotide sequence encoding a miR-145 nucleic acid; or 6) one or more exogenous nucleic acids comprising nucleotide sequences encoding both a miR-143 nucleic acid and a miR-145 nucleic acid). In some embodiments, a subject genetically modified host cell is in vitro. In some embodiments, a subject genetically modified host cell is a human cell or is derived from a human cell. In some embodiments, a subject genetically modified host cell is a rodent cell or is derived from a rodent cell. The present disclosure further provides progeny of a subject genetically modified stem cell or progenitor cell, where the progeny can comprise the same exogenous nucleic acid as the subject genetically modified stem cell or progenitor cell from which it was derived. The present disclosure further provides vascular smooth muscle cells derived from (generated from) a subject genetically modified stem cell or progenitor cell. The present disclosure further provides a composition comprising a subject genetically modified host cell.

Genetically Modified Stem Cells and Genetically Modified Progenitor Cells

In some embodiments, a subject genetically modified host cell is a genetically modified stem cell or progenitor cell. Suitable host cells include, e.g., stem cells (adult stem cells, embryonic stem cells; iPS cells) and progenitor cells (including cardiac progenitor cells). Suitable host cells include mammalian stem cells and progenitor cells, including, e.g., rodent stem cells, rodent progenitor cells, human stem cells, human progenitor cells, etc. Suitable host cells include in vitro host cells, e.g., isolated host cells.

In some embodiments, a subject genetically modified host cell comprises an exogenous miR-143 nucleic acid. In some embodiments, a subject genetically modified host cell comprises an exogenous miR-145 nucleic acid. In some embodiments, a subject genetically modified host cell comprises both an exogenous miR-143 nucleic acid and an exogenous miR-145 nucleic acid. In some embodiments, a subject genetically modified host cell comprises an exogenous nucleic acid comprising a nucleotide sequence encoding a miR-143 nucleic acid, as described above. In other embodiments, a subject genetically modified host cell comprises an exogenous nucleic acid comprising a nucleotide sequence encoding a miR-145 nucleic acid, as described above. In other embodiments, a subject genetically modified host cell comprises one or more exogenous nucleic acids comprising nucleotide sequences encoding both a miR-143 nucleic acid and a miR-145 nucleic acid.

Genetically Modified VSMC Progenitor Cells; Genetically Modified VSMC

The present disclosure provides a genetically modified VSMC progenitor cell comprising an exogenous miR-143 nucleic acid, or an exogenous nucleic acid comprising a nucleotide sequence encoding a miR-143 nucleic acid. The present disclosure provides a genetically modified VSMC comprising an exogenous miR-143 nucleic acid, or an exogenous nucleic acid comprising a nucleotide sequence encoding a miR-143 nucleic acid. The present disclosure provides a genetically modified VSMC progenitor cell comprising an exogenous miR-145 nucleic acid, or an exogenous nucleic acid comprising a nucleotide sequence encoding a miR-145 nucleic acid. The present disclosure provides a genetically modified VSMC comprising an exogenous miR-145 nucleic acid, or an exogenous nucleic acid comprising a nucleotide sequence encoding a miR-145 nucleic acid. The present disclosure provides a genetically modified VSMC progenitor cell comprising an exogenous miR-143 nucleic acid and an exogenous miR-145 nucleic acid, or one or more exogenous nucleic acids comprising nucleotide sequences encoding a miR-143 nucleic acid and a miR-145 nucleic acid. The present disclosure provides a genetically modified VSMC comprising an exogenous miR-143 nucleic acid and an exogenous miR-145 nucleic acid, or one or more exogenous nucleic acids comprising nucleotide sequences encoding a miR-143 nucleic acid and a miR-145 nucleic acid.

In some embodiments, the present disclosure provides human or murine cells (e.g., VSMC progenitor cells or VSMC) comprising an exogenous miR-143 nucleic acid, or an exogenous nucleic acid comprising a nucleotide sequence encoding a miR-143 nucleic acid. In another aspect, the present disclosure provides human or murine cells (e.g., VSMC progenitor cells or VSMC) comprising an exogenous miR-145 nucleic acid, or an exogenous nucleic acid comprising a nucleotide sequence encoding a miR-145 nucleic acid. In other embodiments, the present disclosure provides human or murine cells (e.g., VSMC progenitor cells or VSMC) comprising an exogenous miR-143 nucleic acid and an exogenous miR-145 nucleic acid, or one or more exogenous nucleic acids comprising nucleotide sequences encoding a miR-143 nucleic acid and a miR-145 nucleic acid.

In some embodiments, the disclosure provides human or murine cells (e.g., cardiac progenitor cells or cardiomyocytes) derived from iPS cells. In some aspects, the human or murine cells (e.g., cardiac progenitor cells or cardiomyocytes) are generated following the introduction of a miR-143 nucleic acid, or an miR-143-encoding nucleic acid, into an iPS cell. In other aspects, the human or murine cells (e.g., cardiac progenitor cells or cardiomyocytes) are generated following the introduction of a miR-145 nucleic acid, or an miR-145-encoding nucleic acid, into an iPS cell. In other aspects, the human or murine cells (e.g., cardiac progenitor cells or cardiomyocytes) are generated following the introduction of an exogenous miR-143 nucleic acid and an exogenous miR-145 nucleic acid, or one or more exogenous nucleic acids comprising nucleotide sequences encoding a miR-143 nucleic acid and a miR-145 nucleic acid.

Exogenous Nucleic Acids

As noted above, a subject genetically modified host cell comprises an exogenous nucleic acid.

For simplicity, "exogenous nucleic acid" is used to refer to: 1) an exogenous miR-143 nucleic acid; 2) an exogenous miR-145 nucleic acid; 3) both exogenous miR-143 nucleic acid and exogenous miR-145 nucleic acid; 4) an exogenous nucleic acid comprising a nucleotide sequence encoding a miR-143 nucleic acid; 5) an exogenous nucleic acid comprising a nucleotide sequence encoding a miR-145 nucleic acid; or 6) one or more exogenous nucleic acids comprising nucleotide sequences encoding both a miR-143 nucleic acid and a miR-145 nucleic acid.

In any of the above-described embodiments, the exogenous nucleic acid (e.g., 1) an exogenous miR-143 nucleic acid; 2) an exogenous miR-145 nucleic acid; 3) both exogenous miR-143 nucleic acid and exogenous miR-145 nucleic acid; 4) an exogenous nucleic acid comprising a nucleotide sequence encoding a miR-143 nucleic acid; 5) an exogenous nucleic acid comprising a nucleotide sequence encoding a miR-145 nucleic acid; or 6) one or more exogenous nucleic acids comprising nucleotide sequences encoding both a miR-143 nucleic acid and a miR-145 nucleic acid) is stably integrated into the genome of the host cell. In any of the above-described embodiments, the exogenous nucleic acid (e.g., 1) an exogenous miR-143 nucleic acid; 2) an exogenous miR-145 nucleic acid; 3) both exogenous miR-143 nucleic acid and exogenous miR-145 nucleic acid; 4) an exogenous nucleic acid comprising a nucleotide sequence encoding a miR-143 nucleic acid; 5) an exogenous nucleic acid comprising a nucleotide sequence encoding a miR-145 nucleic acid; or 6) one or more exogenous nucleic acids comprising nucleotide sequences encoding both a miR-143 nucleic acid and a miR-145 nucleic acid) is not integrated into the genome of the host cell and is instead present extrachromosomally.

In some embodiments, the exogenous nucleic acid is a recombinant expression vector. In some embodiments, the exogenous nucleic acid is a recombinant expression vector and is stably integrated into the genome of the host cell. For example, in some embodiments, an exogenous nucleic acid (e.g., 1) an exogenous miR-143 nucleic acid; 2) an exogenous miR-145 nucleic acid; 3) both exogenous miR-143 nucleic acid and exogenous miR-145 nucleic acid; 4) an exogenous nucleic acid comprising a nucleotide sequence encoding a miR-143 nucleic acid; 5) an exogenous nucleic acid comprising a nucleotide sequence encoding a miR-145 nucleic acid; or 6) one or more exogenous nucleic acids comprising nucleotide sequences encoding both a miR-143 nucleic acid and a miR-145 nucleic acid), is present in a lentivirus vector, and the recombinant lentivirus vector is stably integrated into the genome of the host cell (e.g., stem cell; progenitor cell; VSMC progenitor cell; VSMC).

Methods of introducing a nucleic acid into a host cell are known in the art, and any known method can be used to introduce a nucleic acid (e.g., an expression construct) into a host cell. Suitable methods include, e.g., infection, lipofection, electroporation, calcium phosphate precipitation, DEAE-dextran mediated transfection, liposome-mediated transfection, and the like.

Compositions

The present disclosure provides a composition comprising a subject genetically modified host cell. A subject composition comprises a subject genetically modified host cell; and will in some embodiments comprise one or more further components, which components are selected based in part on the intended use of the genetically modified host cell. Suitable components include, but are not limited to, salts; buffers; stabilizers; protease-inhibiting agents; cell membrane- and/or cell wall-preserving compounds, e.g., glycerol, dimethylsulfoxide, etc.; nutritional media appropriate to the cell; and the like.

In some embodiments, a subject composition comprises a subject genetically modified host cell and a matrix (a "subject genetically modified cell/matrix composition"), where a subject genetically modified host cell is associated with the matrix. The term "matrix" refers to any suitable carrier material to which the genetically modified cells are able to attach themselves or adhere in order to form a cell composite. In some embodiments, the matrix or carrier material is present already in a three-dimensional form desired for later application.

For example, a matrix (also referred to as a "biocompatible substrate") is a material that is suitable for implantation into a subject. A biocompatible substrate does not cause toxic or injurious effects once implanted in the subject. In one embodiment, the biocompatible substrate is a polymer with a surface that can be shaped into the desired structure that requires repairing or replacing. The polymer can also be shaped into a part of a structure that requires repairing or replacing. The biocompatible substrate can provide the supportive framework that allows cells to attach to it and grow on it.

Suitable matrix components include, e.g., collagen; gelatin; fibrin; fibrinogen; laminin; a glycosaminoglycan; elastin; hyaluronic acid; a proteoglycan; a glycan; poly(lactic acid); poly(vinyl alcohol); poly(vinyl pyrrolidone); poly(ethylene oxide); cellulose; a cellulose derivative; starch; a starch derivative; poly(caprolactone); poly(hydroxy butyric acid); mucin; and the like. In some embodiments, the matrix comprises one or more of collagen, gelatin, fibrin, fibrinogen, laminin, and elastin; and can further comprise a non-proteinaceous polymer, e.g., can further comprise one or more of poly(lactic acid), poly(vinyl alcohol), poly(vinyl pyrrolidone), poly(ethylene oxide), poly(caprolactone), poly(hydroxy butyric acid), cellulose, a cellulose derivative, starch, and a starch derivative. In some embodiments, the matrix comprises one or more of collagen, gelatin, fibrin, fibrinogen, laminin, and elastin; and can further comprise hyaluronic acid, a proteoglycan, a glycosaminoglycan, or a glycan. Where the matrix comprises collagen, the collagen can comprise type I collagen, type II collagen, type III collagen, type V collagen, type XI collagen, and combinations thereof.

The matrix can be a hydrogel. A suitable hydrogel is a polymer of two or more monomers, e.g., a homopolymer or a heteropolymer comprising multiple monomers. Suitable hydrogel monomers include the following: lactic acid, glycolic acid, acrylic acid, 1-hydroxyethyl methacrylate (HEMA), ethyl methacrylate (EMA), propylene glycol methacrylate (PEMA), acrylamide (AAM), N-vinylpyrrolidone, methyl methacrylate (MMA), glycidyl methacrylate (GDMA), glycol methacrylate (GMA), ethylene glycol, fumaric acid, and the like. Common cross linking agents include tetraethylene glycol dimethacrylate (TEGDMA) and N,N'-methylenebisacrylamide. The hydrogel can be homopolymeric, or can comprise co-polymers of two or more of the aforementioned polymers. Exemplary hydrogels include, but are not limited to, a copolymer of poly(ethylene oxide) (PEO) and poly(propylene oxide) (PPO); PluronicTM F-127 (a difunctional block copolymer of PEO and PPO of the nominal formula $EO_{100}$-$PO_{65}$-$EO_{100}$, where EO is ethylene oxide and PO is propylene oxide); poloxamer 407 (a tri-block copolymer consisting of a central block of poly (propylene glycol) flanked by two hydrophilic blocks of poly (ethylene glycol)); a poly(ethylene oxide)-poly(propylene oxide)-poly(ethylene oxide) co-polymer with a nominal molecular weight of 12,500 Daltons and a PEO:PPO ratio of 2:1); a poly(N-isopropylacrylamide)-base hydrogel (a PNIPAAm-based hydrogel); a PNIPAAm-acrylic acid co-polymer (PNIPAAm-co-AAc); poly(-hydroxyethyl methacrylate); poly(vinyl pyrrolidone); and the like.

A subject genetically modified cell/matrix composition can further comprise one or more additional components, where suitable additional components include, e.g., a growth factor; an antioxidant; a nutritional transporter (e.g., transferrin); a polyamine (e.g., glutathione, spermidine, etc.); and the like.

The cell density in a subject genetically modified cell/matrix composition can range from about $10^2$ cells/mm$^3$ to about $10^9$ cells/mm$^3$, e.g., from about $10^2$ cells/mm$^3$ to about $10^4$ cells/mm$^3$, from about $10^4$ cells/mm$^3$ to about $10^6$ cells/mm$^3$, from about $10^6$ cells/mm$^3$ to about $10^7$ cells/mm$^3$, from about $10^7$ cells/mm$^3$ to about $10^8$ cells/mm$^3$, or from about $10^8$ cells/mm$^3$ to about $10^9$ cells/mm$^3$.

The matrix can take any of a variety of forms, or can be relatively amorphous. For example, the matrix can be in the form of a sheet, a cylinder, a tube, a sphere, etc.

Prosthetic Blood Vessel

The present disclosure provides a prosthetic blood vessel (also referred to as an "artificial blood vessel"), comprising a matrix generally in a tubular form that defines a lumen through which blood can flow, and a subject genetically modified host cell embedded within, or arranged on a surface of, the matrix. The prosthetic blood vessel will have first and second ends. In some embodiments, the first and second ends are configured for suturing to a naturally-occurring (endogenous) blood vessel in an individual. Generally, a subject prosthetic blood vessel is longitudinally bendable.

In some embodiments, at least a portion of the prosthetic blood vessel is configured for access by a needle. For example, in some embodiments, a subject prosthetic blood vessel comprises a transcutaneous access port.

A subject prosthetic blood vessel can have a length of from about 0.25 cm to about 10 cm, e.g., from about 0.25 cm to about 0.5 cm, from about 0.5 cm to about 1.0 cm, from about 1.0 cm to about 1.5 cm, from about 1.5 cm to about 2.0 cm, from about 2.0 cm to about 3.0 cm, from about 3.0 cm to about 4.0 cm, from about 4.0 cm to about 5 cm, from about 5 cm to about 7 cm, or from about 7 cm to about 10 cm.

The inner diameter and outer diameter of a subject prosthetic blood vessel are generally compatible with the inner and outer diameters of a natural blood vessel to which the subject prosthetic blood vessel is attached. For example, the inner diameter can range from about 5 mm to about 25 mm, from about 6 mm to about 10 mm, or from about 8 mm to about 20 mm. The outer diameter can range from about 5 mm to about 25 mm, from about 6 mm to about 10 mm, or from about 8 mm to about 20 mm.

Subject genetically modified cells are in some embodiments disposed on an inner surface of the tubular matrix of a subject prosthetic blood vessel, e.g., on an inner surface that defines a lumen through which blood flows. Subject genetically modified cells are in some embodiments disposed between a first layer and a second layer of the tubular matrix.

In some embodiments, the matrix is a single layer. In other embodiments, the matrix is provided in two or more layers. For example, in some embodiments, an external support layer is included, where the external support layer comprises a knit, tubular mesh capable of expanding radially to accommodate radial expansion within normal compliance range.

A subject prosthetic blood vessel is able to withstand ordinary hemodynamic pressures without leaking or rupturing. For example, a subject prosthetic blood vessel is capable of resilient radial expansion in a manner mimicking the compliance properties of an artery. For example, the compliance of subject prosthetic blood vessel can from 3%/100 mm Hg to 30%/100 mm Hg, where compliance is expressed as percentage change in the internal diameter of a vessel per a 100 mm Hg change in vessel pressure.

The matrix comprises one or more biocompatible materials. Exemplary suitable materials include, e.g., polytetrafluoroethylene (PTFE); extended (or expanded) PTFE; a polymer sold under the trademark GORE-TEX; polyethylene terephthalate (PET); ultra thin wall (UTW) material ranging in thickness from about 0.08 millimeter to about 0.25 millimeter; regular thin wall material (RTW) ranging in thickness from about 0.3 millimeter to about 0.8 millimeter; polyamides; polyimides; silicones; fluoroethylypolypropylene (FEP); polypropylfluorinated amines (PFA); other fluorinated polymers; and the like.

The matrix can comprise a substance that promotes cell attachment, e.g., fibrin glue, combinations of fibrinogen and thrombin, collagen, basement membrane, alginate, and mixtures of two or more of the foregoing.

A subject prosthetic blood vessel can comprise, in addition to a subject genetically modified host cell, one or more additional agents. Suitable agents include, e.g., an analgesic, an anesthetic, an antimicrobial compound, an antibody, an anticoagulant, an antifibrinolytic agent, an anti-inflammatory compound, an antiparasitic agent, an antiviral compound, a cytokine, a cytotoxin or cell proliferation inhibiting compound, a chemotherapeutic drug, a growth factor, an osteogenic or cartilage inducing compound, a hormone, an interferon, a lipid, an oligonucleotide, a polysaccharide, a protease inhibitor, a proteoglycan, a polypeptide, a steroid, a vasoconstrictor, a vasodilator, a vitamin, and a mineral.

A subject prosthetic blood vessel can be used as a carotid bypass graft; as an arterio-venous (A-V) shunt; as a coronary artery bypass graft; to replace a portion of a diseased coronary artery; to replace a portion of a diseased peripheral artery or vein; to replace a portion of a defective peripheral artery or vein; to replace a portion of a defective coronary artery; to replace or bypass an atherosclerotic artery; etc. Exemplary uses of a subject prosthetic blood vessel include aneurysm repair, trauma repair, cardiovascular disease treatment, and the like.

Methods of Reparing or Replacing Diseased, Injured, or Defective Bloos Vessels

The present disclosure provides methods of repairing or replacing a diseased, injured, or defective blood vessel in an individual, the method generally involving introducing into an individual a subject prosthetic blood vessel. The present disclosure provides methods of repairing a diseased, injured, or defective blood vessel in an individual, the methods generally involving replacing the diseased, injured, or defective portion of the blood vessel with a subject prosthetic blood vessel.

In some embodiments, the diseased, injured, or defective blood vessel is replaced with a subject prosthetic blood vessel, e.g., a portion of a blood vessel that is diseased, injured, or defective is removed and is replaced with a subject prosthetic blood vessel. For example, a portion of a blood vessel that is diseased, injured, or defective is excised, and a subject prosthetic blood vessel is sutured to the ends of the natural blood vessel that result from excising the diseased, injured, or defective blood vessel portion.

In some embodiments, the portion of a blood vessel that is diseased, injured, or defective is bypassed with a subject prosthetic blood vessel. Bypass methods are well known in the art.

Methods of Reducing Pathological Angiogensis

The present disclosure provides methods of inhibiting vascular smooth muscle cell differentiation. Inhibition of vascular smooth muscle cell differentiation is useful for reducing pathological angiogenesis. A subject method of inhibiting VSMC differentiation generally involves introducing into a VSCM precursor cell: 1) an antisense nucleic acid that reduces miR-143 nucleic acid levels; 2) an antisense nucleic acid that reduces miR-145 levels; 3) a target protector nucleic acid that inhibits binding of a miR-143 nucleic acid to its target; or 4) a target protector nucleic acid that inhibits binding of a miR-145 nucleic acid to its target.

Whether angiogenesis is reduced can be determined using any known method. Methods of determining an effect of an agent (e.g., a subject nucleic acid, e.g., a subject antisense nucleic acid; a subject synthetic target protector nucleic acid) on angiogenesis are known in the art and include, but are not limited to, inhibition of neovascularization into implants impregnated with an angiogenic factor; inhibition of blood vessel growth in the cornea or anterior eye chamber; inhibition of endothelial tube formation in vitro; the chick chorioallantoic membrane assay; the hamster cheek pouch assay; the polyvinyl alcohol sponge disk assay. Such assays are well known in the art and have been described in numerous publications, including, e.g., Auerbach et al. ((1991) *Pharmac. Ther.* 51:1-11), and references cited therein.

The invention further provides methods for treating a condition or disorder associated with or resulting from pathological angiogenesis. In the context of cancer therapy, a reduction in angiogenesis according to the methods of the invention effects a reduction in tumor size; and a reduction in tumor metastasis. Whether a reduction in tumor size is achieved can be determined, e.g., by measuring the size of the tumor, using standard imaging techniques. Whether metastasis is reduced can be determined using any known method. Methods to assess the effect of an agent on tumor size are well known, and include imaging techniques such as computerized tomography and magnetic resonance imaging.

Any condition or disorder that is associated with or that results from pathological angiogenesis, or that is facilitated by neovascularization (e.g., a tumor that is dependent upon neovascularization), is amenable to treatment with an agent that reduces the level of an miR-145 nucleic acid in VSMC or a VSMC precursor, or an agent that reduces binding of a miR-145 nucleic acid to a target nucleic acid (e.g., a Myocd nucleic acid) so as to inhibit angiogenesis.

Conditions and disorders amenable to treatment include, but are not limited to, cancer; atherosclerosis; proliferative retinopathies such as retinopathy of prematurity, diabetic retinopathy, age-related maculopathy, retrolental fibroplasia; excessive fibrovascular proliferation as seen with chronic arthritis; psoriasis; and vascular malformations such as hemangiomas, and the like.

The instant methods are useful in the treatment of both primary and metastatic solid tumors, including carcinomas, sarcomas, leukemias, and lymphomas. Of particular interest is the treatment of tumors occurring at a site of angiogenesis. Thus, the methods are useful in the treatment of any neoplasm, including, but not limited to, carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). The instant methods are also useful for treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, the instant methods are useful for reducing metastases from the tumors described above either when used alone or in combination with radiotherapy and/or other chemotherapeutic agents.

Other conditions and disorders amenable to treatment using the methods of the instant invention include autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemangiomas, and capillary proliferation within atherosclerotic plaques; Osler-Webber Syndrome; plaque neovascularization; telangiectasia; hemophiliac joints; angiofibroma; and excessive wound granulation (keloids).

In order to accomplish reduction of angiogenesis in vivo (e.g., as in the context of treating pathological angiogenesis), an agent that reduces the level of a miR-145 nucleic acid in a VSMC or a VSMC precursor, or an agent that inhibits binding of a miR-145 nucleic acid to a target nucleic acid (e.g., a subject synthetic target protector nucleic acid), will be administered in any suitable manner, typically with pharmaceutically acceptable carriers. One skilled in the art will readily appreciate that the a variety of suitable methods of administering an active agent (e.g., a subject synthetic target protector nucleic acid) in the context of the present invention to a subject are available, and, although more than one route can be used to administer a particular compound, a particular route can provide a more immediate, more effective, and/or associated with fewer side effects than another route. In general, an active agent can be administered according to the method of the invention by, for example, a parenteral, intratumoral, peritumoral, intravenous, intra-arterial, inter-pericardial, intramuscular, intraperitoneal, transdermal, transcutaneous, subdermal, intradermal, or intrapulmonary route.

In some embodiments, an active agent (e.g., a subject synthetic target protector nucleic acid) will be delivered locally. Local administration can be accomplished by, for example, direct injection (e.g., intramuscular injection, intratumoral injection) at the desired treatment site, by introduction of the active agent formulation intravenously at a site near a desired treatment site (e.g., into a vessel or capillary that feeds a treatment site), by intra-arterial introduction, by introduction (e.g., by injection or other method of implantation) of an active agent formulation in a biocompatible gel or capsule within or adjacent a treatment site, by injection directly into muscle or other tissue in which a decrease in pathological angiogenesis is desired, etc.

In another embodiment of interest, the active agent formulation is delivered in the form of a biocompatible gel, which can be implanted (e.g., by injection into or adjacent a treatment site, by extrusion into or adjacent a tissue to be treated, etc.). Gel formulations comprising an active agent can be designed to facilitate local release of the active agent for a sustained period (e.g., over a period of hours, days, weeks, etc.). The gel can be injected into or near a treatment site, e.g., using a needle or other delivery device.

The desirable extent of reduction of pathological angiogenesis will depend on the particular condition or disease being treated, as well as the stability of the patient and possible side-effects.

Target Protector Nucleic Acids

The present disclosure provides a synthetic target protector nucleic acid that binds to a miR-145 target mRNA. A subject target protector nucleic acid does not induce cleavage or translational repression of the target mRNA; however, a subject target protector nucleic acid does inhibit binding of a miR-145 to the miR-145 target mRNA.

A subject synthetic target protector nucleic acid reduces miR-145-mediated activation of translation of a target mRNA by at least about 10%, at least about 20%, at least about 25%, at least about 30%, at least about 40%, at least about 50%, at least about 60%, at least about 70%, at least about 80%, or at least about 90%, or more than 90%, compared to the level of miR-145-mediated activation of translation of the target mRNA in the absence of the synthetic target protector nucleic acid.

Where the miR-145 target mRNA is a positive regulator of angiogenesis, a subject synthetic target protector nucleic acid reduces miR-145-mediated induction of translation of the positive regulator, thereby decreasing the levels in a cell of the positive regulator; in these cases, a subject synthetic target protector nucleic acid inhibits angiogenesis. Thus, for example, a subject synthetic target protector nucleic acid can result in at least about 10%, at least about 20%, at least about 25%, at least about 30%, at least about 40%, at least about 50%, at least about 60%, at least about 70%, at least about 80%, or at least about 90%, or more than 90%, inhibition of angiogenesis, e.g., where the synthetic target protector nucleic acid is introduced into a VSMC precursor.

Target mRNAs that are targets for miR-145-mediated activation of translation include Myocd. Target sequences in the 3'-UTR of Myocd are depicted in FIG. 7. A subject target protector nucleic acid comprises a nucleotide sequence that hybridizes to one or both of the target sites in the 3'-UTR of Myocd as depicted in FIG. 7.

A subject synthetic target protector nucleic acid can have a length of from about 19 nucleotides (nt) to about 50 nt or more, e.g., a subject synthetic target protector nucleic acid can have a length of 19 nt, 20 nt, 21 nt, 22 nt, 23 nt, 24 nt, 25 nt, from 25 nt to about 30 nt, from about 30 nt to about 35 nt, from about 35 nt to about 40 nt, or from about 40 nt to about 50 nt, or longer than 50 nt.

As one non-limiting example, the target mRNA is a Myocd mRNA, and a subject synthetic target protector nucleic acid comprises a nucleotide sequence having at least about 85%, at least about 90%, at least about 95%, at least about 98%, at least about 99%, or 100% nucleotide sequence identity to the following nucleotide sequence: 5'-GTCCAGTGGGACCAT-TGTGGAGTCA-3' (SEQ ID NO:6). For example, a subject synthetic target protector nucleic acid can have a length of 22 nt to about 30 nucleotides, and can comprise a nucleotide sequence having at least about 85%, at least about 90%, at least about 95%, at least about 98%, at least about 99%, or 100% nucleotide sequence identity to the following nucleotide sequence: 5'-GTCCAGTGGGACCATTGTG-GAGTCA-3' (SEQ ID NO:6).

As another example, the target mRNA is a Myocd mRNA, and a subject synthetic target protector nucleic acid comprises a nucleotide sequence having at least about 85%, at least about 90%, at least about 95%, at least about 98%, at least about 99%, or 100% nucleotide sequence identity to the following nucleotide sequence: 5'-GTCCAGTTGC-CTTTCTGATCATCT-3' (SEQ ID NO:8). For example, a subject synthetic target protector nucleic acid can have a length of 22 nt to about 30 nt, and can comprise a nucleotide sequence having at least about 85%, at least about 90%, at least about 95%, at least about 98%, at least about 99%, or 100% nucleotide sequence identity to the following nucleotide sequence: 5'-GTCCAGTTGCCTTTCTGATCATCT-3' (SEQ ID NO:8).

A subject synthetic target protector nucleic acid can be present in a composition, e.g., a pharmaceutical composition, as described in more detail below. In addition, as described in more detail below, a subject synthetic target protector nucleic acid can include one or more modifications (e.g., base modifications, linkage modifications, etc.).

Antisense Nucleic Acids

The present disclosure provides antisense nucleic acids, nucleic acids encoding the antisense nucleic acids, and composition comprising the antisense nucleic acids, where a subject antisense nucleic acid is effective to reduce the level of mature miR-143 or miR-145 nucleic acid in a cell (e.g., a VSMC or a VSMC precursor). In some embodiments, a subject antisense nucleic acid comprises a nucleotide sequence capable of forming a stable duplex with a ribonuclease III cleavage site-containing portion of a miR-143 precursor nucleic acid or a mR-145 precursor nucleic acid. Ribonuclease III cleavage sites include Dicer cleavage sites and Drosha cleavage sites.

In some embodiments, a subject antisense nucleic acid forms a stable duplex with a ribonuclease III cleavage site (e.g., a Drosha cleavage site, or a Dicer cleavage site) present in a miR-143 precursor nucleic acid, and reduces the level of mature miR-143 nucleic acid in an endothelial cell by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more than 90%, compared to the level of mature miR-143 nucleic acid in the endothelial cell in the absences of the antisense nucleic acid.

In some embodiments, a subject antisense nucleic acid forms a stable duplex with a ribonuclease III cleavage site (e.g., a Drosha cleavage site, or a Dicer cleavage site) present in a miR-145 precursor nucleic acid, and reduces the level of mature miR-145 nucleic acid in an endothelial cell by at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, or more than 90%, compared to the level of mature miR-145 nucleic acid in the endothelial cell in the absences of the antisense nucleic acid.

Drosha cleaves pri-microRNA at the base of a stem-loop structure, releasing the stem-loop structure. Helvik et al. (2007) *Bioinformatics* 23:142; Zeng et al. (2005) *EMBO J.* 24:138; MacRae and Doudna (2007) *Curr. Opinion Structural Biol.* 17:138.

A miR-143 precursor nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence set forth in SEQ ID NO:1 as shown in FIG. 6A as miR-143 stem-loop. The nucleotide sequence set forth in SEQ ID NO:1 is *Homo sapiens* miR-143 precursor nucleic acid. For example, a miR-143 precursor nucleic acid comprises a nucleotide sequence having at least about 75%, at least about 80%, at least about 85%, at least about 90%, at least about 95%, at least about 98%, at least about 99%, or 100%, nucleotide sequence identity to a contiguous stretch of from about 50 nucleotides to about 60 nucleotides (nt), from about 60 nt to about 70 nt, from about 70 nt to about 80 nt, from about 80 nt to about 90 nt, from about 90 nt to about 100 nt, or from about 100 nt to 106 nt, of the nucleotide sequence set forth in SEQ ID NO:1 and depicted in FIG. 6A as miR-143 stem-loop.

A suitable antisense nucleic acid comprises a nucleotide sequence that is complementary to nucleotides 22 to nucleotides 49, nucleotides 56 through 84, nucleotides 1 through 22, nucleotides 22 through 40, nucleotides 30 through 49, nucleotides 25 through 45, nucleotides 56 through 70, nucleotides 65 through 84, nucleotides 84 through 106, or other similar portion, of the nucleotide sequence set forth in SEQ ID NO:1 and depicted in FIG. 6A as miR-143 stem-loop. A suitable antisense nucleic acid comprises a nucleotide sequence having fewer than five mismatches in complementarity with nucleotides 22 to nucleotides 49, nucleotides 56 through 84, nucleotides 1 through 22, nucleotides 22 through 40, nucleotides 30 through 49, nucleotides 25 through 45, nucleotides 56 through 70, nucleotides 65 through 84, nucleotides 84 through 106, or other similar portion, of the nucleotide sequence set forth in SEQ ID NO:1 and depicted in FIG. 6A as miR-143 stem-loop. Thus, e.g., a suitable antisense nucleic acid can comprise a nucleotide sequence that has 1, 2, 3, or 4 mismatches in complementarity with nucleotides 1 through 22, nucleotides 22 through 40, nucleotides 30 through 49, nucleotides 25 through 45, nucleotides 56 through 70, nucleotides 65 through 84, nucleotides 84 through 106, or other similar portion, of the nucleotide sequence set forth in SEQ ID NO:1 and depicted in FIG. 6A as miR-143 stem-loop.

The portion of a subject antisense nucleic acid that forms a duplex with a miR-143 precursor nucleic acid (e.g., the portion of a subject antisense nucleic acid that forms a duplex with nucleotides 22 to nucleotides 49, nucleotides 56 through 84, nucleotides 1 through 22, nucleotides 22 through 40, nucleotides 30 through 49, nucleotides 25 through 45, nucleotides 56 through 70, nucleotides 65 through 84, nucleotides 84 through 106, or other similar portion, of the nucleotide sequence set forth in SEQ ID NO:1 and depicted in FIG. 6A as miR-143 stem-loop) has a length of from about 18 nucleotides to about 50 nucleotides. For example, a subject antisense nucleic acid can have a length of from about 18 nt to about 50 nt. One having ordinary skill in the art will appreciate that this embodies antisense nucleic acids having a length of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

A miR-145 precursor nucleic acid comprises a nucleotide sequence having at least about 75%, at least about 80%, at least about 85%, at least about 90%, at least about 95%, at least about 98%, at least about 99%, or 100%, nucleotide sequence identity to the nucleotide sequence set forth in SEQ ID NO:3 as shown in FIG. 6B as miR-145 stem-loop. The nucleotide sequence set forth in SEQ ID NO:3 is *Homo sapiens* miR-145 precursor nucleic acid. For example, a miR-145 precursor nucleic acid comprises a nucleotide sequence having at least about 75%, at least about 80%, at least about 85%, at least about 90%, at least about 95%, at least about 98%, at least about 99%, or 100%, nucleotide sequence identity to a contiguous stretch of from about 40 nucleotides to about 50 nucleotides (nt), from about 50 nt to about 60 nt, from about 60 nt to about 70 nt, from about 70 nt to about 80 nt, or from about 80 nt to 88 nt, of the nucleotide sequence set forth in SEQ ID NO:3 and depicted in FIG. 6B as miR-145 stem-loop.

A suitable antisense nucleic acid comprises a nucleotide sequence that is complementary to nucleotides 19 to nucleotides 38, nucleotides 52 through 71, nucleotides 1 through 19, nucleotides 20 through 40, nucleotides 50 through 65, nucleotides 55 through 70, nucleotides 55 through 80, nucleotides 20 through 35, nucleotides 15 through 35, or other similar portion, of the nucleotide sequence set forth in SEQ ID NO:3 and depicted in FIG. 6B as miR-145 stem-loop. A suitable antisense nucleic acid comprises a nucleotide sequence having fewer than five mismatches in complementarity with nucleotides 19 to nucleotides 38, nucleotides 52 through 71, nucleotides 1 through 19, nucleotides 20 through 40, nucleotides 50 through 65, nucleotides 55 through 70, nucleotides 55 through 80, nucleotides 20 through 35, nucleotides 15 through 35, or other similar portion, of the nucleotide sequence set forth in SEQ ID NO:3 and depicted in FIG. 6B as miR-145 stem-loop. Thus, e.g., a suitable antisense nucleic acid can comprise a nucleotide sequence that has 1, 2, 3, or 4 mismatches in complementarity with nucleotides 1 through 19, nucleotides 20 through 40, nucleotides 50 through 65, nucleotides 55 through 70, nucleotides 55 through 80, nucleotides 20 through 35, nucleotides 15 through 35, or other similar portion, of the nucleotide sequence set forth in SEQ ID NO:3 and depicted in FIG. 6B as miR-145 stem-loop.

The portion of a subject antisense nucleic acid that forms a duplex with a miR-145 precursor nucleic acid (e.g., the portion of a subject antisense nucleic acid that forms a duplex with nucleotides 1 through 19, nucleotides 20 through 40, nucleotides 50 through 65, nucleotides 55 through 70, nucleotides 55 through 80, nucleotides 20 through 35, nucleotides 15 through 35, or other similar portion, of the nucleotide sequence set forth in SEQ ID NO:3 and depicted in FIG. 6B as miR-145 stem-loop) has a length of from about 15 nucleotides to about 50 nucleotides. For example, a subject antisense nucleic acid can have a length of from about 15 nt to about 50 nt. One having ordinary skill in the art will appreciate that this embodies antisense nucleic acids having a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides.

The total length of a subject antisense nucleic acid can be greater than the duplex-forming portion, e.g., the total length of a subject antisense nucleic acid can be from about 20 nucleotides (nt) to about 30 nt, from about 30 nt to about 40 nt, from about 40 nt to about 50 nt, from about 50 nt to about 75 nt, from about 75 nt to about 100 nt, from about 100 nt to about 125 nt, from about 125 nt to about 150 nt, from about 150 nt to about 175 nt, or from about 175 nt to about 200 nt, or greater than 200 nt, in length.

Exemplary, non-limiting nucleotide sequences that can be included in a subject antisense nucleic acid for reducing the level of mature miR-143 nucleic acid in cell (e.g., a VSMC or a VSMC precursor) are as follows:

```
                                      (SEQ ID NO: 46)
1)  5'-gaccagagatgcagcactgcacctcaggctgggaga-3';

(SEQ ID NO: 47)
2)  5'-tgcagcactgcacctcaggctgggaga-3';

(SEQ ID NO: 48)
3)  5'-gaccagagatgcagcactgcacctcagg-3';

(SEQ ID NO: 49)
4)  5'-tctctcttcctgagctacagtgcttcatctcagactc-3';

(SEQ ID NO: 50)
5)  5'-tctctcttcctgagctacagtgcttcat-3';
and (SEQ ID NO: 51)
6)  5'-agctacagtgcttcatctcagactc-3'.
```

Exemplary, non-limiting nucleotide sequences that can be included in a subject antisense nucleic acid for reducing the level of mature miR-145 nucleic acid in cell (e.g., a VSMC or a VSMC precursor) are as follows:

```
                                      (SEQ ID NO: 52)
1)  5'-agggattcctgggaaaactggaccgtgagg-3';

(SEQ ID NO: 53)
2)  5'-agggattcctgggaaaactgg-3';

(SEQ ID NO: 54)
3)  5'-gggaaaactggaccgtgagg-3';

(SEQ ID NO: 55)
4)  5'-cctcaagaacagtatttccaggaatcccc-3';

(SEQ ID NO: 56)
5)  5'-cctcaagaacagtatttccagg-3';
and (SEQ ID NO: 57)
6)  5'-cagtatttccaggaatcccc-3'.
```

The present disclosure further provides a nucleic acid (including an expression vector) that comprises a nucleotide sequence that encodes a subject antisense nucleic acid. Suitable expression vectors include those described above. In some embodiments, the antisense nucleic acid-encoding nucleotide sequence is operably linked to a VSMC-specific promoter. In some embodiments, the antisense nucleic acid-encoding nucleotide sequence is operably linked to an inducible promoter. In the discussion herein relating to compositions comprising, and methods involving use of, an antisense nucleic acid, it should be understood that the present disclosure contemplates compositions comprising a nucleic acid comprising a nucleotide sequence that encodes a subject antisense nucleic acid, and methods involving use of a nucleic acid comprising a nucleotide sequence that encodes a subject antisense nucleic acid.

Modifications

In some embodiments, a subject nucleic acid (e.g., a target protector nucleic acid; an antisense nucleic acid) comprises one or more modifications, e.g., a base modification, a backbone modification, etc. As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally suitable. In addition, linear compounds may have internal nucleotide base complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Backbones and Modified Internucleoside Linkages

Examples of suitable nucleic acids (e.g., a subject synthetic target protector nucleic acid; a subject antisense nucleic acid) containing modifications include nucleic acids containing modified backbones or non-natural internucleoside linkages. Nucleic acids (e.g., a subject synthetic target protector nucleic acid; a subject antisense nucleic acid) having modified backbones include those that retain a phosphorus atom in the backbone and those that do not have a phosphorus atom in the backbone.

Suitable modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Suitable oligonucleotides having inverted polarity comprise a single 3' to 3' linkage at the 3'-most internucleotide linkage i.e. a single inverted nucleoside residue which may be a basic (the nucleobase is missing or has a hydroxyl group in place thereof). Various salts (such as, for example, potassium or sodium), mixed salts and free acid forms are also included.

In some embodiments, a subject nucleic acid (e.g., a subject synthetic target protector nucleic acid; a subject antisense nucleic acid) comprises one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). MMI type internucleoside linkages are disclosed in the above referenced U.S. Pat. No. 5,489,677. Suitable amide internucleoside linkages are disclosed in t U.S. Pat. No. 5,602,240.

Also suitable are nucleic acids (e.g., a subject synthetic target protector nucleic acid; a subject antisense nucleic acid) having morpholino backbone structures as described in, e.g., U.S. Pat. No. 5,034,506. For example, in some embodiments, a subject nucleic acid (e.g., a subject antisense nucleic acid; a subject synthetic target protector nucleic acid) comprises a 6-membered morpholino ring in place of a ribose ring. In some of these embodiments, a phosphorodiamidate or other non-phosphodiester internucleoside linkage replaces a phosphodiester linkage.

Suitable modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Mimetics

A subject nucleic acid (e.g., a subject synthetic target protector nucleic acid; a subject antisense nucleic acid) can be a nucleic acid mimetic. The term "mimetic" as it is applied to polynucleotides is intended to include polynucleotides wherein only the furanose ring or both the furanose ring and the internucleotide linkage are replaced with non-furanose groups, replacement of only the furanose ring is also referred to in the art as being a sugar surrogate. The heterocyclic base moiety or a modified heterocyclic base moiety is maintained for hybridization with an appropriate target nucleic acid. One such nucleic acid, a polynucleotide mimetic that has been shown to have excellent hybridization properties, is referred to as a peptide nucleic acid (PNA). In PNA, the sugar-backbone of a polynucleotide is replaced with an amide containing backbone, in particular an aminoethylglycine backbone. The nucleotides are retained and are bound directly or indirectly to aza nitrogen atoms of the amide portion of the backbone.

One polynucleotide mimetic that has been reported to have excellent hybridization properties is a peptide nucleic acid (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative U.S. patents that describe the preparation of PNA compounds include, but are not limited to: U.S. Pat. Nos. 5,539,082; 5,714,331; and 5,719,262.

Another class of polynucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups has been selected to give a non-ionic oligomeric compound. The non-ionic morpholino-based oligomeric compounds are less likely to have undesired interactions with cellular proteins. Morpholino-based polynucleotides are non-ionic mimics of oligonucleotides which are less likely to form undesired interactions with cellular proteins (Dwaine A. Braasch and David R. Corey, Biochemistry, 2002, 41(14), 4503-4510). Morpholino-based polynucleotides are disclosed in U.S. Pat. No. 5,034,506. A variety of compounds within the morpholino class of polynucleotides have been prepared, having a variety of different linking groups joining the monomeric subunits.

A further class of polynucleotide mimetic is referred to as cyclohexenyl nucleic acids (CeNA).

The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation.

A further modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH$_2$—), group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. Potent and nontoxic antisense oligonucleotides containing LNAs have been described (Wahlestedt et al., Proc. Natl. Acad. Sci. U.S.A., 2000, 97, 5633-5638).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

Modified Sugar Moieties

A subject nucleic acid (e.g., a subject synthetic target protector nucleic acid; a subject antisense nucleic acid) can also include one or more substituted sugar moieties. Suitable polynucleotides comprise a sugar substituent group selected from: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly suitable are O((CH$_2$)$_{10}$)$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON((CH$_2$)$_n$CH$_3$)$_2$, where n and m are from 1 to about 10. Other suitable polynucleotides comprise a sugar substituent group selected from: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A suitable modification includes 2'-methoxyethoxy (2'-O—CH$_2$ CH$_2$OCH$_3$, also known as 2'-O-(2-methoxyethyl) or 2'-MOE) (Martin et al., Hely. Chim. Acta, 1995, 78, 486-504) i.e., an alkoxyalkoxy group. A further suitable modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Other suitable sugar substituent groups include methoxy (—O—CH$_3$), aminopropoxy (—OCH$_2$CH$_2$CH$_2$NH$_2$), allyl (—CH$_2$—CH=CH$_2$), —O-allyl (—O—CH$_2$—CH=CH$_2$) and fluoro (F). 2'-sugar substituent groups may be in the arabino (up) position or ribo (down) position. A suitable 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar.

Base Modifications and Substitutions

A subject nucleic acid (e.g., a subject synthetic target protector nucleic acid; a subject antisense nucleic acid) may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido (5,4-b)(1,4)benzoxazin-2(3H)-one), phenothiazine cytidine (1H-pyrimido(5,4-b)(1,4)benzothiazin-2(3H)-one), G-clamps such as a substituted phenoxazine cytidine (e.g. 9-(2-aminoethoxy)-H-pyrimido(5,4-(b) (1,4)benzoxazin-2 (3H)-one), carbazole cytidine (2H-pyrimido(4,5-b)indol-2-one), pyridoindole cytidine (H-pyrido(3',2':4,5)pyrrolo(2,3-d)pyrimidin-2-one).

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are useful for increasing the binding affinity of an oligomeric compound (e.g., an antisense nucleic acid; a target protector nucleic acid). These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi et al., eds., Antisense Research and Applications, CRC Press, Boca Raton, 1993, pp. 276-278) and are suitable base substitutions, e.g., when combined with 2'-O-methoxyethyl sugar modifications.

Conjugates

Another possible modification of a subject nucleic acid (e.g., a subject synthetic target protector nucleic acid; a subject antisense nucleic acid) involves chemically linking to the polynucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Suitable conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that enhance the pharmacokinetic properties include groups that improve uptake, distribution, metabolism or excretion of a subject antisense nucleic acid or target protector nucleic acid.

Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-

237), or an octadecylamine or hexylamino-carbonyl-oxycholesterol moiety (Crooke et al., J. Pharmacol. Exp. Ther., 1996, 277, 923-937.

Compositions and Formulations

The present invention provides compositions, e.g., pharmaceutical compositions, comprising a subject nucleic acid (e.g., a subject synthetic target protector nucleic acid; a subject antisense nucleic acid). A wide variety of pharmaceutically acceptable excipients is known in the art and need not be discussed in detail herein. Pharmaceutically acceptable excipients have been amply described in a variety of publications, including, for example, A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds 7th ed., Lippincott, Williams, & Wilkins; and Handbook of Pharmaceutical Excipients (2000) A. H. Kibbe et al., eds., 3rd ed. Amer. Pharmaceutical Assoc.

A subject composition can include: a) a subject nucleic acid; and b) one or more of: a buffer, a surfactant, an antioxidant, a hydrophilic polymer, a dextrin, a chelating agent, a suspending agent, a solubilizer, a thickening agent, a stabilizer, a bacteriostatic agent, a wetting agent, and a preservative. Suitable buffers include, but are not limited to, (such as N,N-bis(2-hydroxyethyl)-2-aminoethanesulfonic acid (BES), bis(2-hydroxyethyl)amino-tris(hydroxymethyl) methane (BIS-Tris), N-(2-hydroxyethyl)piperazine-N'3-propanesulfonic acid (EPPS or HEPPS), glycylglycine, N-2-hydroxyehtylpiperazine-N'-2-ethanesulfonic acid (HEPES), 3-(N-morpholino)propane sulfonic acid (MOPS), piperazine-N,N'-bis(2-ethane-sulfonic acid) (PIPES), sodium bicarbonate, 3-(N-tris(hydroxymethyl)-methyl-amino)-2-hydroxy-propanesulfonic acid) TAPSO, (N-tris(hydroxymethyl)methyl-2-aminoethanesulfonic acid (TES), N-tris(hydroxymethyl)methyl-glycine (Tricine), tris(hydroxymethyl)-aminomethane (Tris), etc.). Suitable salts include, e.g., NaCl, $MgCl$, KCl, $MgSO_4$, etc.

A subject pharmaceutical formulation can include a subject target protector nucleic acid in an amount of from about 0.001% to about 90% (w/w). In the description of formulations, below, "subject nucleic acid" will be understood to include a subject synthetic target protector nucleic acid. For example, in some embodiments, a subject formulation comprises a subject target protector nucleic acid.

A subject nucleic acid can be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption.

A subject nucleic acid can encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. For example, prodrug versions a subject nucleic acid can be prepared as SATE ((S acetyl-2-thioethyl) phosphate) derivatives according to the methods disclosed in WO 93/24510, WO 94/26764, and U.S. Pat. No. 5,770,713.

The term "pharmaceutically acceptable salts" refers to physiologically and pharmaceutically acceptable salts of a subject nucleic acid: i.e., salts that retain the desired biological activity of the parent compound and do not impart undesired toxicological effects thereto. For polynucleotides, suitable examples of pharmaceutically acceptable salts and their uses are further described in U.S. Pat. No. 6,287,860, which is incorporated herein by reference in its entirety.

The present invention also includes compositions and formulations, including pharmaceutical compositions and formulations, which include one or more of a subject nucleic acid. A subject composition can be administered in a number of ways depending upon whether local or systemic treatment is desired and upon the area to be treated. Administration can be systemic or local, e.g., where local administration includes peritumoral, intratumoral, etc. Parenteral administration includes, but is not limited to, intravenous, intraarterial, subcutaneous, intraperitoneal, or intramuscular injection or infusion; or intracranial, e.g., intrathecal or intraventricular, administration. Nucleic acids with at least one 2'-O-methoxyethyl modification can be used for oral administration. Compositions and formulations for topical administration can include transdermal patches, ointments, lotions, creams, gels, drops, suppositories, sprays, liquids, and powders. Conventional pharmaceutical carriers, aqueous, powder or oily bases, thickeners and the like may be necessary or desirable.

A subject formulation, which may conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

A subject composition can be formulated into any of many possible dosage forms such as, but not limited to, tablets, capsules, gel capsules, liquid syrups, soft gels, suppositories, and enemas. A subject composition can also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

A subject composition may include solutions, emulsions, foams and liposome-containing formulations. A subject composition or formulation can comprise one or more penetration enhancers, carriers, excipients, or other active or inactive ingredients.

Emulsions are typically heterogeneous systems of one liquid dispersed in another in the form of droplets, which can exceed 0.1 μm in diameter. Emulsions may contain additional components in addition to the dispersed phases, and the active agent (e.g., antisense polynucleotides) which can be present as a solution in the aqueous phase, the oily phase, or as a separate phase. Microemulsions are also suitable. Emulsions and their uses are well known in the art and are further described in U.S. Pat. No. 6,287,860.

A subject formulation can be a liposomal formulation. As used herein, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes that can interact with negatively charged DNA molecules to form a stable complex. Liposomes that are pH sensitive or negatively charged are believed to entrap DNA rather than complex with it. Both cationic and noncationic liposomes can be used to deliver a subject nucleic acid.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein by reference in its entirety.

The formulations and compositions of the present invention may also include surfactants. The use of surfactants in drug products, formulations and in emulsions is well known in the art. Surfactants and their uses are further described in U.S. Pat. No. 6,287,860.

In one embodiment, various penetration enhancers are included, to effect the efficient delivery of nucleic acids, e.g., a subject target protector nucleic acid. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein by reference in its entirety.

A subject nucleic acid can be conjugated to poly(L-lysine) to increase cell penetration. Such conjugates are described by Lemaitre et al., Proc. Natl. Acad. Sci. USA, 84, 648-652 (1987). The procedure requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride.

One of skill in the art will recognize that formulations are routinely designed according to their intended use and/or route of administration.

Suitable formulations for topical administration include those in which a subject nucleic acid is in admixture with a topical delivery agent such as lipids, liposomes, fatty acids, fatty acid esters, steroids, chelating agents and surfactants. Suitable lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, a subject nucleic acid can be encapsulated within liposomes or may form complexes thereto, in particular to cationic liposomes. Alternatively, a subject nucleic acid can be complexed to lipids, in particular to cationic lipids. Suitable fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets, or minitablets. Thickeners, flavoring agents, diluents, emulsifiers, dispersing aids or binders may be desirable. Suitable oral formulations include those in which a subject antisense nucleic acid is administered in conjunction with one or more penetration enhancers surfactants and chelators. Suitable surfactants include, but are not limited to, fatty acids and/or esters or salts thereof, bile acids and/or salts thereof. Suitable bile acids/salts and fatty acids and their uses are further described in U.S. Pat. No. 6,287,860. Also suitable are combinations of penetration enhancers, for example, fatty acids/salts in combination with bile acids/salts. An exemplary suitable combination is the sodium salt of lauric acid, capric acid, and UDCA. Further penetration enhancers include, but are not limited to, polyoxyethylene-9-lauryl ether, and polyoxyethylene-20-cetyl ether. Suitable penetration enhancers also include propylene glycol, dimethylsulfoxide, triethanoiamine, N,N-dimethylacetamide, N,N-dimethylformamide, 2-pyrrolidone and derivatives thereof, tetrahydrofurfuryl alcohol, and AZONE™.

A subject nucleic acid can be delivered orally, in granular form including sprayed dried particles, or complexed to form micro or nanoparticles. Nucleic acid complexing agents and their uses are further described in U.S. Pat. No. 6,287,860.

Compositions and formulations for parenteral, intrathecal, or intraventricular administration may include sterile aqueous solutions which may also contain buffers, diluents and other suitable additives such as, but not limited to, penetration enhancers, carrier compounds and other pharmaceutically acceptable carriers or excipients.

Delivery and Routes of Administration

A subject nucleic acid (e.g., a subject synthetic target protector nucleic acid; a subject antisense nucleic acid) can be administered by any suitable means. One skilled in the art will appreciate that many suitable methods of administering a subject nucleic acid (e.g., a subject synthetic target protector nucleic acid; a subject antisense nucleic acid) to a host in the context of the present invention, in particular a human, are available, and, although more than one route may be used to administer a particular subject antisense nucleic acid, a particular route of administration may provide a more immediate and more effective reaction than another route. In the following description of delivery and routes of administration, a "subject nucleic acid" will be understood to include a subject synthetic target protector nucleic acid.

Suitable routes of administration include enteral and parenteral routes. Administration can be via a local or a systemic route of administration. A subject nucleic acid (e.g., a subject synthetic target protector nucleic acid; a subject antisense nucleic acid) can be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes, but is not limited to, intravenous, intraarterial, subcutaneous, intraperitoneal, or intramuscular injection or infusion; and intracranial, e.g., intrathecal or intraventricular, administration. Intratumoral and peritumoral administration is also contemplated.

Dosing

The formulation of therapeutic compositions and their subsequent administration (dosing) is within the skill of those in the art. Dosing is dependent on several criteria, including severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in vitro and in vivo animal models.

For example, a suitable dose of a subject nucleic acid (e.g., subject synthetic target protector nucleic acid; a subject antisense nucleic acid) is from 0.01 µg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein a subject nucleic acid (e.g., a subject synthetic target protector nucleic acid; a subject antisense nucleic acid) is administered in maintenance doses, ranging from 0.01 jig to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 µg to 1 mg per kg of body weight.

In some embodiments, multiple doses of a subject nucleic acid (e.g., a subject synthetic target protector nucleic acid; a subject antisense nucleic acid) are administered. The frequency of administration of an active agent (a subject nucleic acid) can vary depending on any of a variety of factors, e.g., severity of the symptoms, etc. For example, in some embodiments, a subject nucleic acid (e.g., a subject synthetic target protector nucleic acid) is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The duration of administration of an active agent (e.g., a subject synthetic target protector nucleic acid; a subject antisense nucleic acid), e.g., the period of time over which an active agent is administered, can vary, depending on any of a variety of factors, e.g., patient response, etc. For example, an active agent can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

Combination Therapy

A subject method of decreasing angiogenesis (e.g., to treat a disorder associated with pathological angiogenesis) can involve administering an agent (e.g., an agent that reduces the level of a miR-145 nucleic acid in a VSMC or a VSMC precursor; a subject target protector nucleic acid; a subject antisense nucleic acid), and can further involve administering at least a second therapeutic agent. For example, a subject method of decreasing angiogenesis (e.g., to treat a disorder associated with pathological angiogenesis) can involve administering a subject synthetic target protector nucleic acid or a subject antisense nucleic acid, and can further involve administering at least a second therapeutic agent. Suitable second therapeutic agents include agents that reduce angiogenesis; anti-cancer chemotherapeutic agents; anti-inflammatory agents; etc.

Agents that reduce angiogenesis include, e.g., a soluble vascular endothelial growth factor (VEGF) receptor; 2-ME (NSC-659853); PI-88 (D-mannose, O-6-O-phosphono-alpha-D-mannopyranosyl-(1-3)-O-alpha-D-manno- pyranosyl-(1-3)-O-alpha-D-mannopyranosyl-(1-3)-O-alpha-D-mannopyranosyl-(1- 2)-hydrogen sulphate); thalidomide (1H-isoindole-1,3 (2H)-dione, 2-(2,6-dioxo-3-piperidinyl)-); CDC-394; CC-5079; ENMD-0995 (S-3-amino-phthalidoglutarimide); AVE-8062A; vatalanib; SH-268; halofuginone hydrobromide; atiprimod dimaleate (2-azaspivo[4.5]decane-2-p-ropanamine, N,N-diethyl-8,8-dipropyl, dimaleate); ATN-224; CHIR-258; combretastatin A-4 (phenol, 2-methoxy-5-[2-(3,4,5-trimethoxyphenyl)etheny-1]-, (Z)-); GCS-100LE, or an analogue or derivative thereof; 2-methoxyestradiol; A6; ABT-510; ABX-IL8, actimid, Ad5FGF-4, AG3340, alpha5beta1 integrin antibody, AMG001, anecortave acetate, angiocol, angiogenix, angiostatin, angiozyme, antiangiogenic antithrombin 3, anti-VEGF, anti-VEGF Mab, aplidine, aptosyn, ATN-161, avastin, AVE8062A, Bay 12-9566, benefin, BioBypass CAD, MS275291, CAI, carboxymidotriazole, CC 4047, CC 5013, CC7085, CDC801, Celebrex, CEP-7055, CGP-41251/PKC412, cilengitide, CM101, col-3, combretastatin, combretastatin A4P, CP-547, 632, CP-564, 959, Del-1, dexrazoxane, didemnin B, DMXAA, EMD 121974, endostatin, FGF (AGENT 3), flavopiridol, GBC-100, genistein concentrated polysaccharide, green tea extract, HIF-1 alpha, human chorio-gonadotrophin, IM862, INGN 201, interferon alpha-2a, interleukin-12, iressa, ISV-120, LY317615, LY-333531, Mab huJ591-DOTA-90 Yttrium, marimastat, Medi-522, metaret, neoretna, neovastat, NM-3, NPe6, NVIFGF, octreotide, oltipraz, paclitaxel, pegaptanib sodium, penicillamine, pentosan polysulphate, prinomastat, PSK, psorvastat, PTK787/ZK222584, ranibizumab, razoxane, replistatatin, revimid, RhuMab, Ro317453, squalamine, SU101, SU11248, SU5416, SU6668, tamoxifen, tecogalan sodium, temptostatin, tetrathiomol, tetrathiomolybdate, thalomid, TNP-470, UCN-01, VEGF, VEGF trap, Vioxx, vitaxin, vitaxin-2, ZD6126, ZD6474, angiostatin (plasminogen fragment), a TIMPs, antiangiogenic antithrombin III, pigment epithelial-derived factor (PEDF), canstatin, placental ribonuclease inhibitor, cartilage-derived inhibitor (CDI), plasminogen activator inhibitor, CD59 complement fragment, platelet factor-4, endostatin (collagen XVIII fragment), prolactin 16 kD fragment, fibronectin fragment, proliferin-related protein, gro-beta, a retinoid, a heparinase, tetrahydrocortisol-S, heparin hexasaccharide fragment, thrombospondin-1, human chorionic gonadotropin, transforming growth factor-beta, interferon alpha, interferon beta, or interferon gamma, tumistatin, interferon inducible protein, vasculostatin, interleukin-12, vasostatin (calreticulin fragment), kringle 5 (plasminogen fragment), angioarrestin, or 2-methoxyestradiol. Angiogenesis inhibitors also include antagonists of angiogenin, placental growth factor, angiopoietin-1, platelet-derived endothelial cell growth factor, Del-1, platelet-derived growth factor-BB, aFGF, bFGF, pleiotrophin, follistatin, proliferin, granulocyte colony-stimulating factor, transforming growth factor-alpha, hepatocyte growth factor, transforming growth factor-beta, interleukin-8, tumor necrosis factor-alpha, and vascular endothelial growth factor. Angiogenesis inhibitors include ABT-510, ABX-IL8 (Abgenix), actimid, Ad5FGF-4 (Collateral Therapeutics), AG3340 (Agouron Pharmaceuticals Inc. LaJolla, Calif.), α5β1 integrin antibody, AMG001 (AnGes/Daichi Pharmaceuticals), anecortave acetate (Retaane, Alcon), angiocol, angiogenix (Endovasc Ltd), angiostatin (EntreMed), angiozyme, antiangiogenic antithrombin 3 (Genzyme Molecular Oncology), anti-VEGF (Genentech), anti-VEGF Mab, aplidine, aptosyn, ATN-161, avastin (bevacizumab), AVE8062A, Bay 12-9566 (Bayer Corp. West Haven, Conn.), benefin, BioBypass CAD (VEGF-121) (GenVec), MS275291, CAI (carboxy-amido imidazole), carboxymidotriazole, CC 4047 (Celgene), CC 5013 (Celgene), CC7085, CDC 801 (Celgene), Celebrex (Celecoxib), CEP-7055, CGP-41251/PKC412, cilengitide, CM 101 (Carbomed Brentwood, Term.), col-3 (CollaGenex Pharmaceuticals Inc. Newton, Pa.), combretastatin, combretastatin A4P (Oxigene/Bristol-Myers Squibb), CP-547, 632, CP-564, 959, Del-1 (VLTS-589) (Valentis), dexrazoxane, didemnin B, DMXAA, EMD 121974, endostatin (EntreMed), FGF (AGENT 3) (Berlex (Krannert Institute of Cardiology)), flavopiridol, GBC-100, genistein concentrated polysaccharide, IM862 (Cytran), INGN 201, interferon alpha-2a, interleukin-12, Iressa, ISV-120 (Batimastat), LY317615, LY-333531 (Eli Lilly and Company), Mab huJ591-DOTA-90 Yttrium (90Y), marimastat (British Biotech Inc. Annapolis, Md.), Medi-522, metaret (suramin), neoretna, neovastat (AEtema Laboratories), NM-3, NPe6, NV1FGF (Gencel/Aventis), octreotide, oltipraz, paclitaxel (e.g., taxol, docetaxel, or paxene), pegaptanib sodium (Eyetech), penicillamine, pentosan polysulphate, PI-88, prinomastat (Agouron Pharmaceuticals), PSK, psorvastat, PTK787/ZK222584, ranibizumab (Lucentis, Genentech), razoxane, replistatatin (Platelet factor-4), revimid, RhuMab, Ro317453, squalamine (Magainin Pharmaceuticals, Inc. Plymouth Meeting, Pa.), SU101 (Sugen Inc. Redwood City, Calif.), SU11248, SU5416 (Sugen), SU6668 (Sugen), tamoxifen, tecogalan sodium, temptostatin, tetrathiomol, and tetrathiomolybdate.

Chemotherapeutic agents for treating cancer include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation; therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283, 253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Methods of Inducing Therapeutic Angiogenesis

The present disclosure provides methods for inducing therapeutic angiogenesis. The methods generally involve introducing into a VSMC or a VSMC precursor: 1) a miR-143 nucleic acid; 2) a miR-145 nucleic acid; 3) both a miR-143 nucleic acid and a miR-145 nucleic acid; 4) a nucleic acid comprising a nucleotide sequence that encodes a miR-143 nucleic acid; 5) a nucleic acid comprising a nucleotide sequence that encodes a miR-145 nucleic acid; or 6) one or more nucleic acids comprising nucleotide sequences encoding a miR-143 nucleic acid and a miR-145 nucleic acid. Methods of inducing therapeutic angiogenesis are useful in treating various disorders, including, e.g., cardiac ischemia, limb ischemia, etc. Thus, in some embodiments, the instant disclosure provides a method of increasing or stimulating therapeutic angiogenesis in an individual, where increasing or stimulating therapeutic angiogenesis can treat a disorder that is amenable to treatment by stimulating or increasing angiogenesis.

An effective amount of an active agent (e.g., 1) a miR-143 nucleic acid; 2) a miR-145 nucleic acid; 3) both a miR-143 nucleic acid and a miR-145 nucleic acid; 4) a nucleic acid comprising a nucleotide sequence that encodes a miR-143 nucleic acid; 5) a nucleic acid comprising a nucleotide sequence that encodes a miR-145 nucleic acid; or 6) one or more nucleic acids comprising nucleotide sequences encoding a miR-143 nucleic acid and a miR-145 nucleic acid) increases angiogenesis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 2-fold, at least about 5-fold, at least about 10-fold, or more, when compared to an untreated (e.g., a placebo-treated) control. Stimulation of angiogenesis is useful to treat a variety of conditions that would benefit from stimulation of angiogenesis, stimulation of vasculogenesis, increased blood flow, and/or increased vascularity.

Suitable nucleic acids are described above. As described above, in some embodiments, a nucleic acid that comprises a nucleotide sequence encoding a miR-143 nucleic acid, a nucleic acid that comprises a nucleotide sequence encoding a miR-145 nucleic acid, or a nucleic acid that comprises a nucleotide sequence encoding a miR-143 nucleic acid and a miR-145 nucleic acid, will be present in an expression vector. Suitable expression vectors are described above. In some embodiments, the miR-143- and/or the miR-145-encoding nucleotide sequence is operably linked to a control element (e.g., a promoter). Suitable control elements are described above.

Examples of conditions and diseases amenable to treatment according to the method of the invention related to increasing angiogenesis include any condition associated with an obstruction of a blood vessel, e.g., obstruction of an artery, vein, or of a capillary system. Specific examples of such conditions or disease include, but are not necessarily limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, and the like. Examples of conditions or diseases that can be reduced using the methods of the invention include, but are not necessarily limited to, heart attack (myocardial infarction) or other vascular death, stroke, death or loss of limbs associated with decreased blood flow, and the like.

Other forms of therapeutic angiogenesis include, but are not necessarily limited to, the use of an active agent to accelerate healing of wounds or ulcers (e.g., as a result of physical injury or disease, e.g., cutaneous ulcers, diabetic ulcers, ulcerative colitis, and the like); to improve the vascularization of skin grafts or reattached limbs so as to preserve their function and viability; and to improve the healing of surgical anastomoses (e.g., as in re-connecting portions of the bowel after gastrointestinal surgery).

In order to accomplish stimulation of angiogenesis in vivo (e.g., as in the context of therapeutic angiogenesis), an active agent can be administered in any suitable manner, preferably with pharmaceutically acceptable carriers. One skilled in the art will readily appreciate that the a variety of suitable methods of administering an active agent in the context of the present invention to a subject are available, and, although more than one route can be used to administer a particular compound, a particular route can provide a more immediate, more effective, and/or associated with fewer side effects than another route. In general, an active agent is administered according to the method of the invention by, for example, a parenteral, intravenous, intra-arterial, inter-pericardial, intramuscular, intraperitoneal, transdermal, transcutaneous, subdermal, intradermal, or intrapulmonary route.

In some embodiments, an active agent will be delivered locally. Local administration can be accomplished by, for example, direct injection (e.g., intramuscular injection) at the desired treatment site, by introduction of the active agent formulation intravenously at a site near a desired treatment site (e.g., into a vessel or capillary that feeds a treatment site), by intra-arterial or intra-pericardial introduction, by introduction (e.g., by injection or other method of implantation) of an active agent formulation in a biocompatible gel or capsule within or adjacent a treatment site, by injection directly into muscle or other tissue in which increased blood flow and/or increased vascularity is desired, by rectal introduction of the formulation (e.g., in the form of a suppository to, for example, facilitate vascularization of a surgically created anastomosis after resection of a piece of the bowel), etc.

In some embodiments it may be desirable to deliver the active agent directly to the wall of a vessel. One exemplary method of vessel wall administration involves the use of a drug delivery catheter, particularly a drug delivery catheter comprising an inflatable balloon that can facilitate delivery to a vessel wall. Thus, in one embodiment the method of the invention comprises delivery of an active agent to a vessel wall by inflating a balloon catheter, wherein the balloon comprises an active agent formulation covering a substantial portion of the balloon. The active agent formulation is held in place against the vessel wall, promoting adsorption through the vessel wall. In one example, the catheter is a perfusion balloon catheter, which allows perfusion of blood through the catheter while holding the active agent against the vessel walls for longer adsorption times. Examples of catheters suitable for active agent application include drug delivery catheters disclosed in U.S. Pat. No. 5,558,642; U.S. Pat. No. 5,554,119; 5,591,129; and the like.

In another embodiment of interest, the active agent formulation is delivered in the form of a biocompatible gel, which can be implanted (e.g., by injection into or adjacent a treatment site, by extrusion into or adjacent a tissue to be treated, etc.). Gel formulations comprising an active agent can be designed to facilitate local release of the active agent for a sustained period (e.g., over a period of hours, days, weeks, etc.). The gel can be injected into or near a treatment site, e.g., using a needle or other delivery device. In one embodiment, the gel is placed into or on an instrument which is inserted into the tissue and then slowly withdrawn to leave a track of gel, resulting in stimulation of angiogenesis along the path made by the instrument. This latter method of delivery may be particularly desirable for, for the purpose of directing course of the biobypass.

In other embodiments it may be desirable to deliver the active agent formulation topically, e.g., for localized delivery, e.g., to facilitate wound healing. Topical application can be accomplished by use of a biocompatible gel, which may be provided in the form of a patch, or by use of a cream, foam, and the like. Several gels, patches, creams, foams, and the like appropriate for application to wounds can be modified for delivery of active agent formulations according to the invention (see, e.g., U.S. Pat. Nos. 5,853,749; 5,844,013; 5,804,213; 5,770,229; and the like). In general, topical administration is accomplished using a carrier such as a hydrophilic colloid or other material that provides a moist environment. Alternatively, for the purpose of wound healing the active agent could be supplied, with or without other angiogenic agents in a gel or cream then could be applied to the wound. An example of such an application would be as a sodium carboxymethylcellulose-based topical gel with a low bioburden containing the active agent and other active ingredients together with preservatives and stabilizers.

In other embodiments, the active agent formulation is delivered locally or systemically, e.g., locally, using a transdermal patch. Several transdermal patches are well known in the art for systemic delivery of nicotine to facilitate smoking cessation, and such patches may be modified to provide for delivery of an amount of active agent effective to stimulate angiogenesis according to the invention (see, e.g., U.S. Pat. Nos. 4,920,989; and 4,943,435, NICOTROL™ patch, and the like).

In other methods of delivery, the active agent can be administered using iontophoretic techniques. Methods and compositions for use in iontophoresis are well known in the art (see, e.g., U.S. Pat. Nos. 5,415,629; 5,899,876; 5,807,306; and the like).

The desirable extent of angiogenesis will depend on the particular condition or disease being treated, as well as the stability of the patient and possible side-effects. In proper doses and with suitable administration, the present invention provides for a wide range of development of blood vessels, e.g., from little development to essentially full development.

Combination Therapy

A subject method of increasing angiogenesis (e.g., to treat a disorder amenable to treatment by increasing angiogenesis) can involve administering an active agent (e.g., a subject target protector nucleic acid) to an individual, and can further involve administering at least a second therapeutic agent. Suitable second therapeutic agents include agents (including polypeptide agents and non-polypeptide agents) that increase angiogenesis; wound-healing agents; etc.

Suitable angiogenic polypeptides include, but are not limited to, VEGF polypeptides, including $VEGF_{121}$, $VEGF_{165}$, VEGF-C, VEGF-2, etc.; transforming growth factor-beta; basic fibroblast growth factor; glioma-derived growth factor; angiogenin; angiogenin-2; and the like. The amino acid sequences of various angiogenic agents are publicly available, e.g., in public databases such as GenBank; journal articles; patents and published patent applications; and the like. For example, amino acid sequences of VEGF polypeptides are disclosed in U.S. Pat. Nos. 5,194,596, 5,332,671, 5,240,848, 6,475,796, 6,485,942, and 6,057,428; amino acid sequences of VEGF-2 polypeptides are disclosed in U.S. Pat. Nos. 5,726,152 and 6,608,182; amino acid sequences of glioma-derived growth factors having angiogenic activity are disclosed in U.S. Pat. Nos. 5,338,840 and 5,532,343; amino acid sequences of angiogenin are found under GenBank Accession Nos. AAA72611, AAA51678, AAA02369, AAL67710, AAL67711, AAL67712, AAL67713, and AAL67714; etc.

Methods of Inhibiting Vascular Smooth Muscle Cell Proliferation

The present disclosure provides methods for inhibiting vascular smooth muscle cell proliferation. The methods generally involve administering to an individual in need thereof an effective amount of a miR-143 nucleic acid and/or a miR-145 nucleic acid, or at least one nucleic acid comprising nucleotide sequences encoding a miR-143 nucleic acid and/or a miR-145 nucleic acid. The administered nucleic acid enters a VSMC and inhibits proliferation of the VSMC. The methods are useful for inhibiting or reducing vascular remodeling of a traumatized mammalian blood vessel. Thus, the present disclosure provides methods for inhibiting vascular remodeling of a traumatized mammalian blood vessel. A subject method is also useful for treating atherosclerosis, e.g., slowing the progression of atherosclerosis, reducing the likelihood that atherosclerosis will occur, etc. Thus, the present disclosure provides methods for inhibiting atherosclerosis.

In some embodiments, a nucleic acid comprising a nucleotide sequence encoding a miR-143 nucleic acid is administered. In some embodiments, a nucleic acid comprising a nucleotide sequence encoding a miR-145 nucleic acid is administered. In some embodiments, one or more nucleic acids comprising nucleotide sequences encoding a miR-143 nucleic acid and a miR-145 nucleic acid is administered. In any of these embodiments, the nucleic acid can be an expression vector, as described above. In any of these embodiments, the miR-143-encoding and/or the miR-145-encoding nucleotide sequence can be operably linked to a control element, as described above.

In some embodiments, administration of an effective amount of a miR-143 nucleic acid and/or a miR-145 nucleic acid, or at least one nucleic acid comprising nucleotide sequences encoding a miR-143 nucleic acid and/or a miR-145 nucleic acid, to an individual in need thereof can result in one or both of: (i) retention of an expanded luminal diameter or cross-sectional area following angioplasty (e.g., percutaneous transluminal coronary angioplasty (PTCA), percutaneous transluminal angioplasty (PTA), and the like) or other trauma, including atheroectomy (e.g., rotoblater, laser and the like), coronary artery bypass procedures, and the like; or resulting from vascular disease, e.g, atherosclerosis, eye diseases secondary to vascular stenosis or atrophy, cerebral vascular stenotic diseases, and the like; and (ii) reduced VSMC proliferation.

Thus, in some embodiments, an effective amount of a miR-143 nucleic acid and/or a miR-145 nucleic acid, or at least one nucleic acid comprising nucleotide sequences encoding a miR-143 nucleic acid and/or a miR-145 nucleic acid, is an amount that, when administered to a vessel, reduces diminution of luminal diameter of the vessel by at least about 5%, at least about 10%, at least about 15%, at least about 20%, at least about 25%, at least about 30%, at least about 40%, at least about 50%, or more than 50%, compared to the diminution of luminal diameter of the vessel in the absence of treatment with the nucleic acid. In some embodiments, an effective amount of a miR-143 nucleic acid and/or a miR-145 nucleic acid, or at least one nucleic acid comprising nucleotide sequences encoding a miR-143 nucleic acid and/or a miR-145 nucleic acid, is an amount that, when administered to a vessel, results in retention of at least about 50%, at least about 60%, at least about 70%, at least about 80%, or at least about 90%, of the expanded luminal diameter or cross-sectional area of the vessel following angioplasty.

In some embodiments, an effective amount of a miR-143 nucleic acid and/or a miR-145 nucleic acid, or at least one nucleic acid comprising nucleotide sequences encoding a miR-143 nucleic acid and/or a miR-145 nucleic acid, is an amount that, when administered in such a manner that the nucleic acid enters a VSMC in a blood vessel, reduces VSMC proliferation in the vessel by at least about 5%, at least about 10%, at least about 15%, at least about 20%, at least about 25%, at least about 30%, at least about 35%, at least about 40%, at least about 50%, at least about 60%, at least about 70%, at least about 80%, or at least about 90%, compared to the rate of proliferation of the VSMC in the vessel in the absence of treatment with the nucleic acid. VSMC proliferation can be determined by measuring $^3$H-thymidine uptake.

In some embodiments, a subject method inhibits diminution of vessel lumen diameter of a mammalian blood vessel. In some embodiments, a subject method inhibits diminution of vessel lumen diameter of a traumatized mammalian blood vessel. In some embodiments, a subject method inhibits diminution of vessel lumen diameter of a diseased blood vessel.

In some embodiments, an effective amount of a nucleic acid (e.g., 1) a miR-143 nucleic acid; 2) a miR-145 nucleic acid; 3) both a miR-143 nucleic acid and a miR-145 nucleic acid; 4) a nucleic acid comprising a nucleotide sequence that encodes a miR-143 nucleic acid; 5) a nucleic acid comprising a nucleotide sequence that encodes a miR-145 nucleic acid; or 6) one or more nucleic acids comprising nucleotide sequences encoding a miR-143 nucleic acid and a miR-145 nucleic acid) is an amount that reduces, delays, or eliminates intimal thickening. As used herein the term "reducing" means decreasing the intimal thickening that results from stimulation of smooth muscle cell proliferation following angioplasty, either in an animal model or in a human. "Delaying" means delaying the time until onset of visible intimal hyperplasia (e.g., observed histologically or by angiographic examination) following angioplasty and may also be accompanied by "reduced" restenosis. "Eliminating" restenosis following angioplasty means completely "reducing" intimal thickening and/or completely "delaying" intimal hyperplasia in a patient to an extent which makes it no longer necessary to surgically intervene, i.e., to reestablish a suitable blood flow through the vessel by repeat angioplasty, atheroectomy, or coronary artery bypass surgery. The effects of reducing, delaying, or eliminating stenosis may be determined by methods routine to those skilled in the art including, but not limited to, angiography, ultrasonic evaluation, fluoroscopic imaging, fiber optic endoscopic examination or biopsy and histology.

A subject method is useful for the treatment of restenosis and related complications following percutaneous transluminal coronary angioplasty and other similar arterial/venous procedures.

In some embodiments, a miR-143 nucleic acid and/or a miR-145 nucleic acid, or at least one nucleic acid comprising nucleotide sequences encoding a miR-143 nucleic acid and/or a miR-145 nucleic acid, is administered via an implantable device. For example, a miR-143 nucleic acid and/or a miR-145 nucleic acid, or at least one nucleic acid comprising nucleotide sequences encoding a miR-143 nucleic acid and/or a miR-145 nucleic acid, is administered in situ, by means of an implantable device, wherein the miR-143 nucleic acid and/or miR-145 nucleic acid, or the at least one nucleic acid comprising nucleotide sequences encoding a miR-143 nucleic acid and/or a miR-145 nucleic acid, is releasably embedded in, coated on, or embedded in and coated on, the implantable device.

In some embodiments, a subject method of reducing VSCM proliferation in a mammalian blood vessel comprises administering to a traumatized mammalian blood vessel a sustained release dosage form comprising microparticles or nanoparticles comprising a miR-143 nucleic acid and/or a miR-145 nucleic acid, or at least one nucleic acid comprising nucleotide sequences encoding a miR-143 nucleic acid and/or a miR-145 nucleic acid. The sustained release dosage form comprising a miR-143 nucleic acid and/or a miR-145 nucleic acid, or at least one nucleic acid comprising nucleotide sequences encoding a miR-143 nucleic acid and/or a miR-145 nucleic acid, can be administered via an implantable device. The amount administered is effective inhibit or reduce diminution in vessel lumen area of the mammalian blood vessel. The sustained release dosage form can comprise microparticles of from about 4 microns (μm) to about 50 microns in diameter. The sustained release dosage form can also range from about 2 microns to about 50 microns in diameter, or greater than 3 microns and less than 10 microns in diameter. For nanoparticles, exemplary sizes include from about 10 nanometers (nm) to about 5000 nm, from about 20 nm to about 500 nm, or from about 50 nm to about 200 nm.

In some embodiments, a subject method comprises administering to a mammalian blood vessel a dosage form of a miR-143 nucleic acid and/or a miR-145 nucleic acid, or at least one nucleic acid comprising nucleotide sequences encoding a miR-143 nucleic acid and/or a miR-145 nucleic acid, in a non-liquid vehicle or matrix effective inhibit or reduce diminution in vessel lumen area of the mammalian blood vessel. In some embodiments, the dosage form is a substantially solid dosage form other than microparticles, nanoparticles, and the like. The non-liquid vehicle or matrix can include, e.g., a gel, paste, or a membrane which comprises nucleic acid.

In some embodiments, a nucleic acid (e.g., 1) a miR-143 nucleic acid; 2) a miR-145 nucleic acid; 3) both a miR-143 nucleic acid and a miR-145 nucleic acid; 4) a nucleic acid comprising a nucleotide sequence that encodes a miR-143 nucleic acid; 5) a nucleic acid comprising a nucleotide sequence that encodes a miR-145 nucleic acid; or 6) one or more nucleic acids comprising nucleotide sequences encoding a miR-143 nucleic acid and a miR-145 nucleic acid) is coated onto and/or embedded in an implantable device, and the implantable device is implanted into a site in an individual. Suitable sites include, e.g., at or near an injured blood vessel (e.g., a blood vessel injured due to accidental trauma; a blood vessel injured due to a surgical procedure; etc.); and at or near a diseased blood vessel (e.g., at or near a site of atherosclerosis).

Compositions and devices suitable for use in introducing a nucleic acid (e.g., 1) a miR-143 nucleic acid; 2) a miR-145 nucleic acid; 3) both a miR-143 nucleic acid and a miR-145 nucleic acid; 4) a nucleic acid comprising a nucleotide sequence that encodes a miR-143 nucleic acid; 5) a nucleic acid comprising a nucleotide sequence that encodes a miR-145 nucleic acid; or 6) one or more nucleic acids comprising nucleotide sequences encoding a miR-143 nucleic acid and a miR-145 nucleic acid) into a site in an individual are described below.

Compositions and Devices

The present disclosure provides compositions and devices comprising a miR-143 nucleic acid and/or a miR-145 nucleic acid, or at least one nucleic acid comprising nucleotide sequences encoding a miR-143 nucleic acid and/or a miR-145 nucleic acid. In some embodiments, a subject composition comprises a miR-143 nucleic acid and/or a miR-145 nucleic acid, or at least one nucleic acid comprising nucleotide sequences encoding a miR-143 nucleic acid and/or a miR-145 nucleic acid, where the nucleic acid is in a sustained release dosage form. In some embodiments, a subject device comprises a miR-143 nucleic acid and/or a miR-145 nucleic acid, or at least one nucleic acid comprising nucleotide sequences encoding a miR-143 nucleic acid and/or a miR-145 nucleic acid, where the nucleic acid is coated onto the device or is otherwise releasably associated with the device.

The present disclosure provides compositions and devices comprising a nucleic acid (e.g., 1) a miR-143 nucleic acid; 2) a miR-145 nucleic acid; 3) both a miR-143 nucleic acid and a miR-145 nucleic acid; 4) a nucleic acid comprising a nucleotide sequence that encodes a miR-143 nucleic acid; 5) a nucleic acid comprising a nucleotide sequence that encodes a miR-145 nucleic acid; or 6) one or more nucleic acids comprising nucleotide sequences encoding a miR-143 nucleic acid and a miR-145 nucleic acid), where in some embodiments, the nucleic acid is in an expression vector. Suitable expression vectors and control elements are as described above.

Sustained Release Dosage Forms

Sustained release dosage forms can include microparticles and/or nanoparticles having a miR-143 nucleic acid and/or a miR-145 nucleic acid, or at least one nucleic acid comprising nucleotide sequences encoding a miR-143 nucleic acid and/or a miR-145 nucleic acid, dispersed therein. For sustained release administration, microparticle dosage forms comprising pure active agent (nucleic acid) can be used. The therapeutic dosage forms of this aspect of the present disclosure may be of any configuration suitable for sustained release. Exemplary sustained release therapeutic dosage forms exhibit one or more of the following characteristics: microparticles (e.g., from about 0.5 micrometers ($\mu$m) to about 100 $\mu$m in diameter, e.g., from about 0.5 $\mu$m to about 2 $\mu$m; or from about 0.01 $\mu$m to about 200 $\mu$m in diameter, e.g., from about 0.5 $\mu$m to about 50 $\mu$m, or from about 2 $\mu$m to about 15 $\mu$m) or nanoparticles (e.g., from about 1.0 nanometer (nm) to about 1000 nm in diameter, e.g., from about 50 nm to about 250 nm, or from about 0.01 nm to about 1000 nm in diameter, or from about 50 nm to about 200 nm), free flowing powder structure; biodegradable structure designed to biodegrade over a period of time, e.g., between from about 0.5 day to about 180 days, from about 1-3 days to about 150 days, from about 3 nm to about 180 days, or from about 10 nm to about 21 days; or non-biodegradable structure to allow therapeutic agent diffusion to occur over a time period of between from about 0.5 day to about 180 days, from about 30 days to about 120 days; from about 3 days to about 180 days, or from about 10 days to about 21 days; biocompatible with target tissue and the local physiological environment into which the dosage form to be administered, including yielding biocompatible biodegradation products; facilitate a stable and reproducible dispersion of therapeutic agent therein, e.g., to form a therapeutic agent-polymer matrix, with active therapeutic agent release occurring by one or both of the following routes: (1) diffusion of the therapeutic agent through the dosage form (when the therapeutic agent is soluble in the shaped polymer or polymer mixture defining the dimensions of the dosage form); or (2) release of the therapeutic agent as the dosage form biodegrades.

Implantable Devices

Suitable devices include, but are not limited to, coronary stents, peripheral stents, catheters, arterio-venous grafts, by-pass grafts, and drug delivery balloons used in the vasculature. Suitable stents include the Silver stent, Gianturco-Roubin stent, the Palmaz-Schatz stent, Wallstent, Mammotherm stent, Symphony stent, Smart stent, Perflex, AVE, Intrastent, and Herculink stems, self-expanding Instent, Gianturco Z-stent, Ultraflex nitinol mesh stent, Esophacoil stent, Gianturco Z tracheobronchial tree stent, and the Wallstent tracheobronchial endoprosthesis.

In some embodiments, the device is adapted for the delivery of at least one therapeutic agent (e.g., 1) a miR-143 nucleic acid; 2) a miR-145 nucleic acid; 3) both a miR-143 nucleic acid and a miR-145 nucleic acid; 4) a nucleic acid comprising a nucleotide sequence that encodes a miR-143 nucleic acid; 5) a nucleic acid comprising a nucleotide sequence that encodes a miR-145 nucleic acid; or 6) one or more nucleic acids comprising nucleotide sequences encoding a miR-143 nucleic acid and a miR-145 nucleic acid) to a site in the lumen of a traumatized mammalian vessel.

A nucleic acid (e.g., 1) a miR-143 nucleic acid; 2) a miR-145 nucleic acid; 3) both a miR-143 nucleic acid and a miR-145 nucleic acid; 4) a nucleic acid comprising a nucleotide sequence that encodes a miR-143 nucleic acid; 5) a nucleic acid comprising a nucleotide sequence that encodes a miR-145 nucleic acid; or 6) one or more nucleic acids comprising nucleotide sequences encoding a miR-143 nucleic acid and a miR-145 nucleic acid) can be formulated in a subject sustained release dosage form, or in a subject implantable device, in combination with another therapeutic agent including, e.g., an anti-proliferative agent, an agent that reduces platelet adhesion, an agent that inhibits activation of platelet, an anti-coagulant, an anti-mitotic agent, a plasminogen activator, an agent that reduces platelet aggregation, an anti-inflammatory agent, an anti-thrombotic agent, a thrombolytic agent, a fibrinolytic agent, an anti-lipidemic agent, a matrix metalloproteinase inhibitor, and antibiotic, and the like.

Suitable antithrombotic agents include, e.g., heparin, hirudin, hirulog, and PPACK (D-phenylalanyl-L-prolyl-L-arginine). Suitable plasminogen activators include, for example, anistreplase, urokinase (UK), pro-urokinase (pUK), streptokinase (SK), tissue plasminogen activator (tPA). Suitable anticoagulants include glycoprotein IIb/IIIa inhibitors, ticlopidine, clopidigrel, warfarin, coumadin, and aspirin. Suitable thrombolytics and/or fibrinolytics include tPA, recombinant tPA, urokinase, streptokinase, Tenecteplase, Alteplase, Activase, Lysatec, Antistreplase, APSAC, Eminase, Retaplase, Retavase, Hannahpep (Indian King Cobra venom), and Ancrod (Malayan pit viper venom.

Aents that can be included in a subject device include, e.g., antiproliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin; antiplatelet agents such as G(GP) IIb/IIIa inhibitors and vitronectin receptor antagonists; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazanes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine }); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory; such as adrenocortical steroids (cortisol, cortisone, fludrocortisone, prednisone, prednisolone, 6α-methylylprednisolone, triamcinolone, betamethasone, and dexamethasone), non-steroidal agents (salicylic acid derivatives i.e, aspirin; para-aminophenol derivaties i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives; (cyclosporine, tacrolimus (FK-506), sirolimus (rapamycin), azathioprine, mycophenolate mofetil); angiogenic agents; vascular endothelial growth factor (VEGF), fibroblast growth factor (FGF); angiotensin receptor blockers; and nitric oxide donors.

A subject implantable device can comprise a supporting structure having a coating on the surface of the supporting structure, where the coating comprises a miR-143-encoding nucleic acid and/or a miR-145-encoding nucleic acid, and optionally one or more additional therapeutic agents. The term "supporting structure" refers to a framework that is capable of containing or supporting a pharmaceutically acceptable carrier or excipient, which carrier or excipient may contain one or more therapeutic agents or substances, e.g., one or more drugs and/or other compounds. The supporting structure can be formed of metal or a polymeric material.

The coating that comprises a miR-143-encoding nucleic acid and/or a miR-145-encoding nucleic acid can be biostable or biodegradable.

An implantable device includes devices which are placed in the lumen of the vessel, e.g., an indwelling catheter or stent, or on the exterior of a vessel, e.g., an adventitial wrap, mesh or covering, or which become a part of the vessel itself, for example to replace a portion of a diseased or traumatized vessel, e.g., a synthetic graft. The implantable device may comprise the therapeutic agent in a form which is releasably embedded in and/or coated on the device. The therapeutic agent may also be releasably embedded in and/or coated on a pharmaceutically acceptable release carrier matrix, which may be applied to and/or embedded in the device or administered directly to a vessel. The matrix is non-liquid, e.g., solid. For example, a suitable matrix includes, but is not limited to, a gel, a paste, or a permeable membrane. An implantable device may be implanted for a limited amount of time, e.g., catheter or infusion needle delivery of a therapeutic agent, or for a prolonged period of time, e.g., a stent or graft. Vessels into which a subject implantable device can be inserted, include, but are not limited to, coronary vessels (e.g., coronary arteries), femoral vessels, carotid vessels (e.g., carotid arteries), and peripheral vessels. Vessels include arteries and veins.

In some embodiments, a subject device is suitable for use in treating a procedural vascular trauma. As used herein, the term "procedural vascular trauma" includes the effects of surgical/mechanical interventions into mammalian vasculature. Thus, procedural vascular traumas include (1) organ transplantation, such as heart, kidney, liver and the like, e.g., involving vessel anastomosis; (2) vascular surgery, such as coronary bypass surgery, biopsy, heart valve replacement, atheroectomy, thrombectomy, and the like; (3) transcatheter vascular therapies (TVT) including angioplasty, e.g., laser angioplasty and percutaneous transluminal coronary angioplasty (PTCA) procedures, employing balloon catheters, and indwelling catheters; (4) vascular grafting using natural or synthetic materials, such as in saphenous vein coronary bypass grafts, dacron and venous grafts used for peripheral arterial reconstruction, etc.; (5) placement of a mechanical shunt, such as a PTFE hemodialysis shunt used for arterio-venous communications; and (6) placement of an intravascular stent, which may be metallic, plastic, or a biodegradable polymer.

In some embodiments, a miR-143-encoding and/or a miR-145-encoding nucleic acid is administered directly or substantially directly to the traumatized area of the vascular smooth muscle tissue. For example, in some embodiments, a subject composition comprising a miR-143-encoding and/or a miR-145-encoding nucleic acid is administered directly or substantially directly to the traumatized area of the vascular smooth muscle tissue. In some embodiments, a subject implantable device comprising a miR-143-encoding and/or a miR-145-encoding nucleic acid is implanted directly or substantially directly within an injured or diseased blood vessel.

Subjects Suitable for Treatment
Methods of Repairing or Replacing a Diseased, Injured, or Defective Blood Vessel Individuals who are suitable for treatment with a subject method of replacing a diseased, injured, or defective blood vessel include, but are not limited to, individuals with a vascular disease (e.g., atherosclerosis); individuals with coronary artery disease; individuals with an aneurysm; individuals in need of an A-V shunt; individuals with peripheral arterial disease; etc.

Methods of Reducing Pathological Angiogenesis

Subjects suitable for treatment with a method as described herein for reducing pathological angiogenesis include, e.g., individuals having one or more of: a solid tumor; atherosclerosis; proliferative retinopathies such as retinopathy of prematurity, diabetic retinopathy, age-related maculopathy, retrolental fibroplasia; excessive fibrovascular proliferation as seen with chronic arthritis; psoriasis; and vascular malformations such as hemangiomas.

Methods of Inducing Therapeutic Angiogenesis

Subjects suitable for treatment with a subject method of inducing therapeutic angiogenesis include, but are not limited to, individuals having one or more of: cardiac ischemia; limb ischemia; coronary occlusive disease; carotid occlusive disease; arterial occlusive disease; vascular death; and the like.

Methods of Inhibiting Vascular Smooth Muscle Cell Proliferation

Subjects suitable for treatment with a subject method inhibiting VSMC proliferation include, but are not limited to, individuals in whom restenosis has occurred after angioplasty, with stent placement (e.g., the individual has undergone angioplasty and subsequence stent placement); individuals in whom restenosis has occurred after angioplasty, without stent placement (e.g., the individual has undergone angioplasty without subsequent stent placement); individuals who have vascular injury as a result of a surgical procedure; individuals who have vascular injury as a result of trauma; individuals with atherosclerosis; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Experimental Procedures
Transgenic Mice and Flow Cytometry

Transgenic mice were generated and Bluo-gal staining and histological analyses were performed as described[10]. For promoter analysis, fragments were subcloned into a pHsp68LacZ reporter vector and injected into pronuclei. The 4.2-kb regulatory element corresponds to mouse chr 18:61809195-61813466. Islet1-cre mice[17] were crossed with Rosa26-YFP mice[18], embryos were collected at E9.5, and heart and surrounding tissue was dissected, trypsinized, spun at 2000 rpm and the pellet was resuspended in PBS and filtered through a 40-μm Millipore membrane. Selection by fluorescence-activated cell sorting (FACs) was based on expression of yellow fluorescent protein (YFP). YFP+ cells were collected for RNA preparation.

miRNA Microarray and miRNA in Situ Hybridization

Total RNA was isolated (Trizol, Invitrogen) from mouse E9.5 embryonic hearts and used for miRNA microarray hybridizations (Exiqon) and quantitative real-time polymerase chain reaction (PCR). miRNA in situ hybridization analyses were performed as described[31] with the following modifications: paraffin-embedded tissue sections or cryosections were treated for 15 minutes with Proteinase K, hybridized at 59° C. (miR-145) or 42° C. (miR-143), and final color development was performed with Nitro-Blue Tetrazolium Chloride (NBT)/5-Bromo-4-Chloro-3'-Indolyphosphate p-Toluidine Salt (BCIP) (NBT/BCIP) (Roche).

Electromobility Shift Assay (EMSA)

Oligoribonucleotides corresponding to the conserved SRF-binding sites in the miR-143/145 enhancer were synthesized (Integrated DNA Technologies) as follows:

SRF binding site: GGGAGCAGCCTTG CCATATAAGGGCAGG (SEQ ID NO:58); SRF mutant binding site: GGGAGCAGCCTTG CTACCGAAGGGCAGG (SEQ ID NO:59). EMSA was performed as described[32].

miRNA Target Prediction

Putative miRNA target genes were identified using an in-house automated algorithm based on empirical miRNA:mRNA interaction data[10,13] that qualifies mRNAs based on 1) complementarity between the seed region of the miRNA and the mRNA 3' UTR as annotated in RefSeq; 2) identification of an extended binding site; 3) favorable binding affinity between the miRNA and mRNA target site as calculated by RNAhybrid[33]; 4) high free energy in the regions flanking the putative binding site as determined by mFold[34]; 5) absence of stabilizing elements in the binding site; 6) presence of destabilizing elements in the region surrounding and including the possible binding site; and 7) conservation over a number of species.

miR-143 and miR-145 Target Analyses and Expression

A 250-bp fragment encompassing miR-145 was ligated into pSilencer 4.1-CMV (Ambion). A 250-bp fragment containing miR-143 was ligated into pEF-Dest-51(Invitrogen). The entire 3' UTR of each mRNA containing predicted miR-143 and/or miR-145 binding sites was cloned into the pMiR-Report luciferase reporter (Applied Biosystems). All assays were performed in quadruplicate in 12-well plates of Cos-1 cells and transfected with siPort XP-1 (Ambion). After 24 hours, cells were harvested and luciferase activity was measured with the Luciferase Dual-Reporter Kit (Promega). Renilla assays were performed in parallel to normalize for transfection efficiency. Embryonic stem (ES) cells or embryoid bodies (EBs), A10 cells or differentiated 10T1/2 fibroblasts were harvested in Trizol (Invitrogen) for total RNA isolation. Total RNA (2 μg) from each sample was reversed transcribed with Superscript III (Invitrogen). Taqman primers were used to amplify genes (ABI; primer sequences available upon request). The primers to detect the 1.7 kb miR-143/145 primary transcript were as follows: Forward: GCATCTCTG-GTCAGTTGGG (SEQ ID NO:60), Reverse: GACCTCAA-GAACAGTAT (SEQ ID NO:61). Glyceraldehyde-3-phosphate dehydrogenase (GAPDH) was used as a control. DGCR8$^{null}$ EBs (Day 8, D10 EBs) were a gift from R. Blelloch[16]. miRNA quantitative PCR (qPCR) on β-MHC-green fluorescent protein (GFP) control EBs, SRF$^{null}$ EBs, or SRF$^{null}$ EBs expressing miR-1 or miR-133 was performed as described above; miR-16 was used as the endogenous control. Each qPCR was performed at least three times; representative results are shown as fold expression relative to undifferentiated ES cells.

Tissue Culture

10T1/2 fibroblasts were maintained at low density (~30% confluence) in DMEM with 10% fetal bovine serum (FBS) and were transfected with Lipofectomine 2000 (Invitrogen) and 1-2 μg of full length or smooth muscle isoform of Myocd[35]. Pre-miR-145 sequence containing ~250 by amplified from genomic DNA was cloned into pSilencer 4.1-cytomegalovirus (CMV) vector (Ambion) and pre-miR-143 was cloned into the pEF-Dest-51 vector (Invitrogen). Two days after transfection, media was replaced with differentiation medium (DMEM, 2% horse serum). 4-5 days later, further analyses, including immunocytochemistry, Western blot, and reverse transcription-PCR (RT-PCR) were performed.

A10 smooth muscle cells (SMCs) and Cos-1 cells were maintained in DMEM with 10% FBS. A10 cells were transfected with BlockIT Fluorescent oligo (Invitrogen), miR-143 or miR-145 inhibitor (Dharmacon) or antagomiR (IDT Technologies), or miR-143, 145 mimic (Dharmacon). 24-48 hours later, western blot or RT-PCR was performed.

The Joma1.3 neural crest cell line was maintained as reported'''. Neural crest cells (NCCs) were plated (~7.5×10$^5$ cell density) on plastic culture dishes coated with fibronectin, and kept in an undifferentiated state by the addition of 200 nm 4-hydroxytamoxifen (4-OHT) every 24 hrs. For differentiation into SMCs, transforming growth factor-β (TGF-β) was added 24 hrs after last 4-OHT treatment, which was stopped to allow differentiation to take place within 4-6 days. Pre-miR-145 or -miR-143 was transfected in 6-well culture dishes using 10 μl lipofectamine (Ambion) at concentrations ranging from 66 nm to 132 nm to induce SMC differentiation 24 hrs after removal of Tamoxifen.

Proliferation Assays

Rat aortic A10 vascular smooth muscle cells (VSMCs) proliferation studies were done as reported[36]. Briefly, cells were plated at a density of 5,000 cells/well in 96-well plates containing 5% FBS/DMEM. After plating, miRNAs were transfected at varying concentrations ranging from 20 nM to 240 nM. Twelve hours later, media was washed 3 times and changed to serum free DMEM with antibiotics. Serum free conditions were maintained for 48 hours to allow growth arrest. The medium was then changed to 5% FBS/DMEM and 5 ng/mL of platelet-derived growth factor (PDGF)-bb (R&D Systems) was added to appropriate wells. After 24 hours, rates of proliferation were determined using the CellTiter 96™ assay (Promega). Proliferation was measured by the amount of 490 nm absorbance and is directly proportional to the number of living cells. Proliferation was subsequently expressed as absorbance of cells with treatment compared to cells without treatment. Each experiment was done in quintuplicate.

Immunohistochemistry and Western Blot Analysis

Immunostaining was performed using pre-ready mouse anti-smooth muscle actin (Dako, 1A4), 1:500 mouse anti-caldesmon (Abcam, 12B5), and 1:50 rabbit anti-calponin (Chemicon) antibodies and 1:400 tetramethylrhodamine isothiocyanate (Tritc)- or fluorescein isothiocyanate (Fitc)-conjugated goat anti-mouse IgG or goat anti-rabbit IgG (Jackson ImmunoResearch). Myogenic conversion assays were performed as described, and protein lysates collected[35]. Rat aortic A10 cells were collected and assayed using Elk-1, Klf-4, and CamKII-δ (Cell Signaling) antibodies.

Mouse Vascular Injury and Atherosclerosis Models

Mice that had their left carotid artery ligated were sacrificed 21-days post ligation, fixed and sectioned to obtain cross-sections of the left carotid artery as described[37]; the contralateral right carotid artery was used for control. 12-week-old apolipoprotein (Apo) E- null mice were fed a Western diet for 4 weeks, and aortic lesions were dissected and collected for RNA analysis.

Statistical Analysis

The two-tailed student's t-test, type II, was used for data analysis. P<0.05 was considered significant.

Results

MicroRNAs (miRNAs) represent a class of small (20-25 nucleotides), non-coding RNAs that are key regulators of many cellular events, including the balance between proliferation and differentiation during tumorigenesis and organ development[4-6]. miRNAs are initially transcribed as a longer primary transcript (pri-miRNA) and processed first by the ribonuclease enzyme complex, Drosha/DGCR8, and then by Dicer, leading to incorporation of a single strand into the RNA-induced silencing complex (RISC). Each of the 650 human miRNAs is predicted to interact with over one hundred target mRNAs in a sequence-specific fashion involving Watson-Crick base-pairing among nucleotides 2-8 of the miRNA[7,8]. miRNAs generally inhibit target mRNAs by repressing translation or reducing mRNA stability. miRNAs may also activate mRNA translation under certain cellular conditions[9].

Regulation of cardiac cell fate decisions by miRNAs and control of proliferation and differentiation in cardiac progenitors has been reported, but remains inefficient[10-15]. It was reported that miR-143 is the most enriched miRNA during differentiation of mouse embryonic stem (mES) cells into multipotent cardiac progenitors, which are capable of differentiating into cardiac muscle, smooth muscle, or endothelial cells[14]. miR-143 is highly conserved and lies within 1.7 kilobases of another conserved miRNA, miR-145, on mouse chromosome 18 (FIG. 9a, b), and both are downregulated in various cancer cell lines, colon cancers, and lung cancers. Given their genomic organization and proximity, miR-143 and miR-145 may be contained in a bicistronic primary transcript; however, a common transcript from RNA could not be amplified, possibly because pri-miRNA transcripts are rapidly processed into their mature forms. DGCR8-null ES cells lack nuclear miRNA processing activity and have a defect in differentiation[16], but can form mesoderm. Using primers for each miRNA and RNA from DGCR8-null embryoid bodies (EBs), an amplicon was generated that encompassed both miRNAs (FIG. 9b), suggesting that miR-143 and miR-145 were transcribed as a bi-cistronic unit and therefore share common regulatory elements that control their expression.

Figure 10:
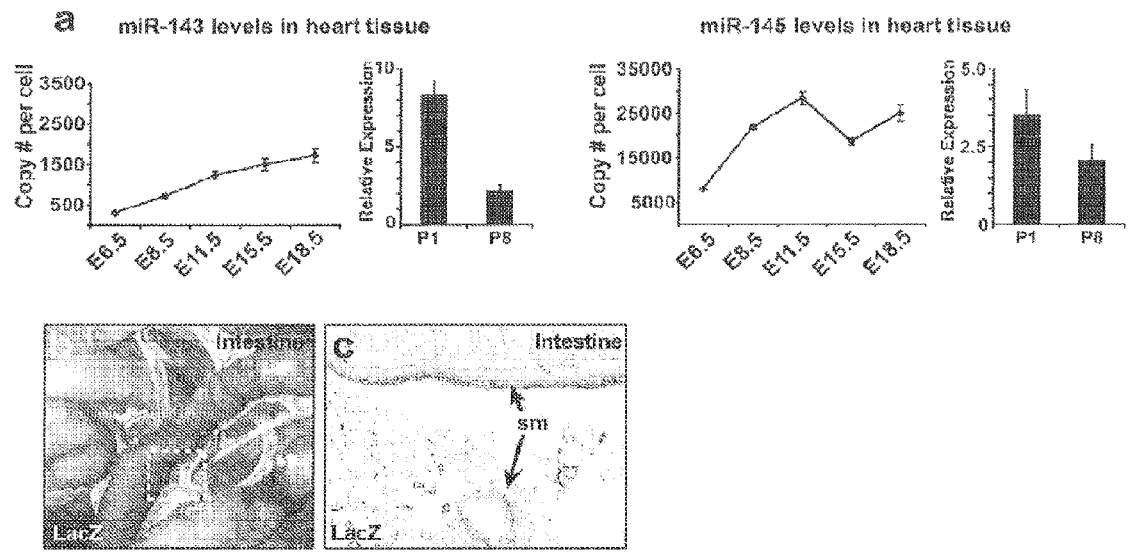
FIGS. 10A-C depict: miRNA copy number per cell estimates at embryonic (E) days indicated (FIG. 10A); β-Gal activity illustrating LacZ expression in the intestines of an E15.5 mouse embryo (FIG. 10B); and a section of the boxed area in (b) showing expression in smooth muscle of intestinal wall and in the vasculature.

To determine if these two miRNAs were also enriched in multipotent cardiac progenitors in vivo, transgenic mice containing Cre recombinase in the Islet1 locus[17] were bred with Rosa26-EYFP mice[18] and isolated YFP+ cardiac progenitor cells at E9.5 by fluorescence-activated cell sorting (FACS) (FIG. 1a and FIG. 1b). The Islet1-Cre mice have been described extensively and mark early multipotent cardiac progenitor cells that can differentiate into cardiac muscle, smooth muscle and endothelial cells[19]. Quantitative RT-PCR (qPCR) revealed that miR-143 and miR-145 were enriched in YFP+ cells (FIG. 1c). qPCR with RNA from mouse hearts or whole embryos at varying stages of development also revealed enrichment of both miRNAs throughout cardiogenesis, before being downregulated in the adult heart (FIG. 1d and FIG. 10a).

To identify the tissue-specific expression and regulation of the miR-143/miR-145 gene during mouse development, a search was conducted for upstream regulatory regions. Comparison of genomic sequences across species revealed a 4.2-kilobase (kb) genomic region upstream of miR-143/miR-145 that was highly conserved between human and mouse (FIG. 9c) and directed LacZ expression specifically in multipotent cardiac mesodermal progenitors of transgenic mice as early as embryonic day (E) 7.75 (FIG. 1e and FIG. 1f). By E9.5, LacZ expression was more robust and uniform in the heart and outflow tract and in cardiac progenitors of the pharyngeal mesoderm; expression was also present in the aorta just as smooth muscle differentiation began, but was absent in the cardinal vein (FIG. 1g, h). LacZ expression was robust in the endocardium and myocardium (FIG. 1h). During later cardiogenesis, expression became restricted to the ventricles and atria, but was notably absent in the aorta and pulmonary arteries (FIG. 1i). Postnatally, the pattern was reversed, with high transcript levels in smooth muscle of the aorta, pulmonary artery, and coronary vessels but undetectable levels in the ventricular myocardium (FIG. 1j-l). This enhancer was also active in the smooth muscle of the intestines (FIG. 10b, c). The enhancer recapitulated endogenous expression in the smooth muscle of the adult aorta and coronary artery as shown by section in situ hybridization (FIG. 1m,n).

FIGS. 1A-O. miR-143 and miR-145 are cardiac and smooth muscle-specific miRNA miR-143 and miR-145 are cardiac and smooth muscle-specific miRNAs. (a) Lateral view of Islet1-cre; R26R-LacZ lineage tracing by X-gal staining showing expression domain at E9.5. (b) Fluorescence-activated cell sorting of YFP+ cells from E9.5 Islet1-cre; R26R-YFP embryos. 10,000 YFP+ cells (blue/box) were obtained. (c) qPCR for levels of miR-143 and miR-145 in YFP+ cells relative to miR-16. (d) qPCR of miR-143 and miR-145 expression in the heart compared to whole embryo throughout embryonic stages. (e) Whole mounts and sections showing cardiac-specific β-gal activity driven by the genomic fragment shown in FIG. 9a at indicated time points. (h) Transverse section of (g) showing β-gal expression in pharyngeal mesoderm (pm), pharyngeal endoderm (pe), dorsal aorta (da), myocardium (mc), endocardium (ec). (i) Expression in the myocardium of the E15.5 heart and absence of expression in the aorta (Ao) and pulmonary artery (pa). (j) Image of day 21 post-natal heart (P21), revealed a switch in β-gal activity evident in the Ao and pa and epicardium, but not in the ventricular myocardium. (k, l) Transverse section of (j) showing LacZ activity in the Ao and coronary (co) artery smooth muscle (inset), but not in ventricular myocardium. (m,n) Section in-situ hybridization of miR-45 showing smooth muscle expression in the Ao and coronary artery but not in ventricular myocardium, similar to LacZ activity. (1) and (n) represent higher magnification of boxed areas. (o) Expression of miR-143 and miR-145 in adult heart or aorta relative to liver indicating enrichment in vacular smooth muscle. (pcm, pre-cardiac mesoderm; ht, heart; h, head; ot, outflow tract; rv, right ventricle; lv, left ventricle; cv, cardinal vein; ra, right atrium; la, left atrium). *, $p<0.05$. Error bars indicate standard deviation (SD).

Figure 9:
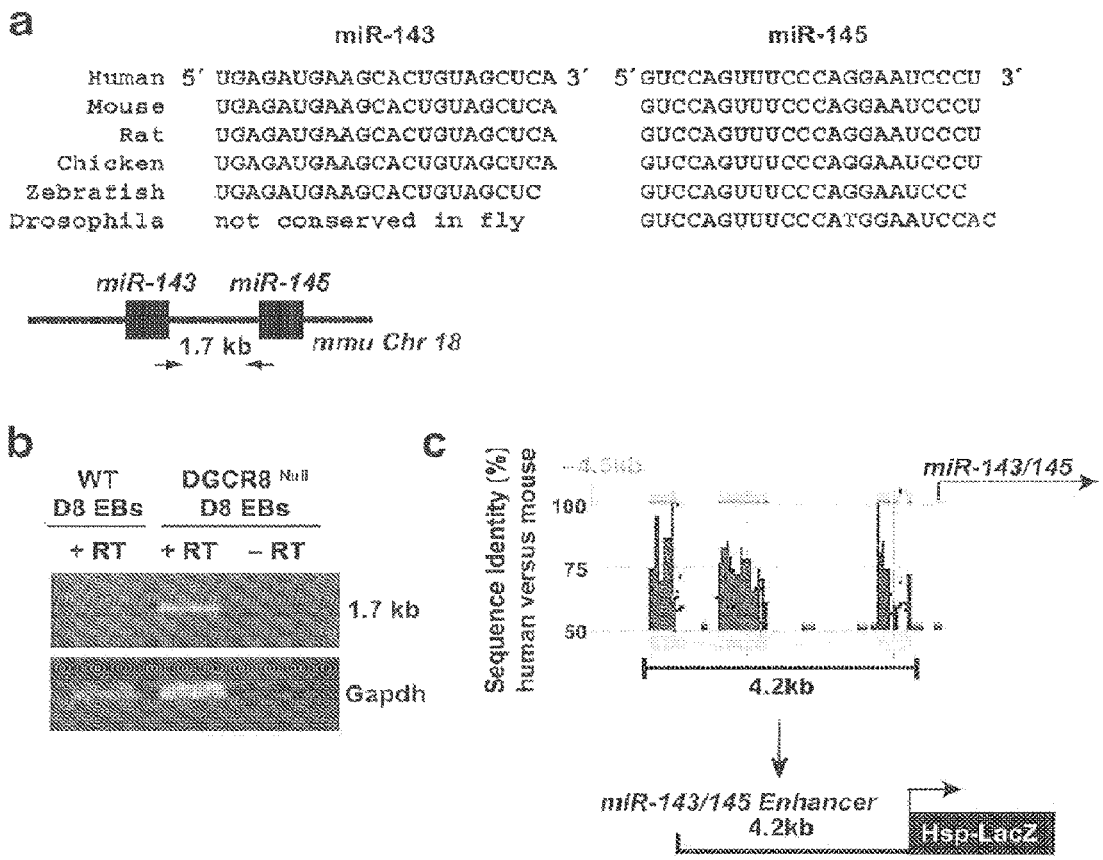
FIGS. 9A-C depict: Sequence conservation of mature miR-143 or miR-145 across species (FIG. 9A); Schematic of the genomic organization of miR-143 and miR-145 on mouse Chromosome 18 (FIG. 9B); and Percent identity between mouse and human across a 4.2 kb genomic region upstream of miR-143/145 cloned into an Hsp68-LacZ cassette (FIG. 9C).

FIGS. 9A-C. (a) Sequence conservation of mature miR-143 or miR-145 across species; red residues indicate variance. Schematic of the genomic organization of miR-143 and miR-145 on mouse Chromosome 18; arrows indicate primers designed to amplify 1.7 kb transcript by reverse transcription of wt or DGCR$^{null}$ cells (b). Gapdh was used as control for RNA loading and PCR performed with or without reverse transcriptase (RT). (c) Percent identity between mouse and human across a 4.2 kb genomic region upstream of miR-143/145 cloned into an Hsp68-LacZ cassette.

FIGS. 10A-C. (a) miRNA copy number per cell estimates at embryonic (E) days indicated. Expression of each miRNA in post-natal day 1 (P1) or P8 ventricles relative to liver is shown. (b) β-Gal activity illustrating LacZ expression in the intestines of an E15.5 mouse embryo. (c) section of boxed area in (a) showing expression in smooth muscle of intestinal wall and in the vasculature.

Figure 2:
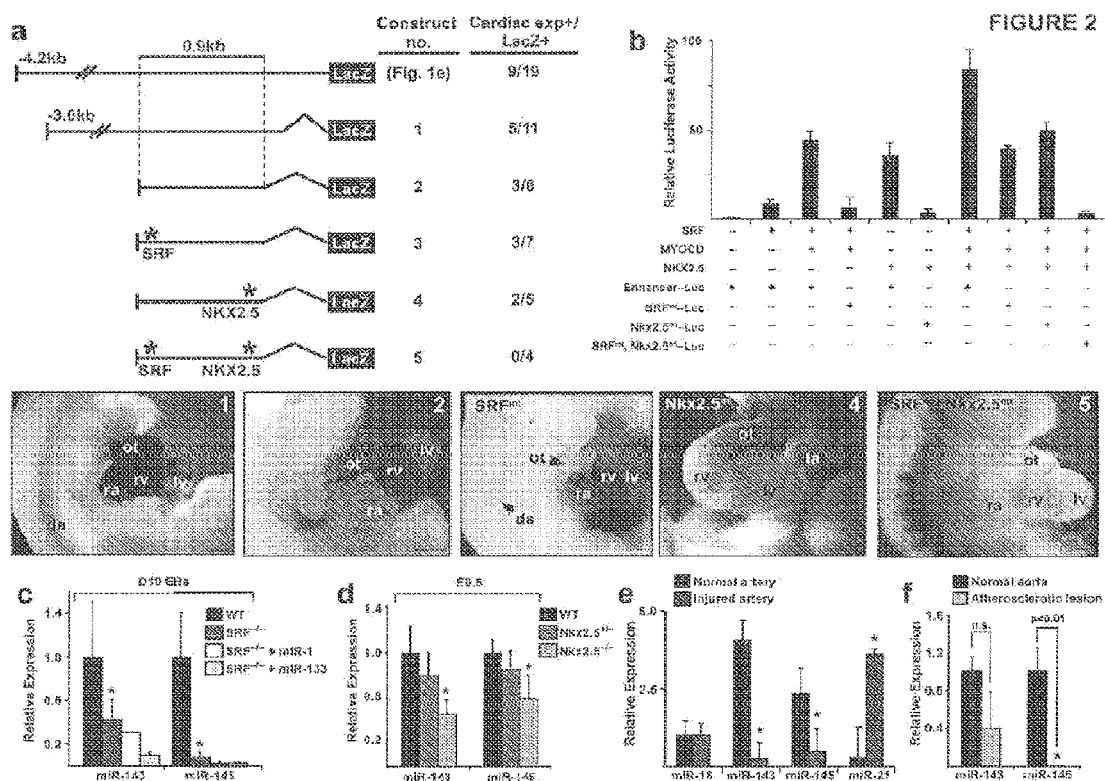
FIGS. 2A-F depict regulation of cardiac and smooth muscle expression of miR-143 and miR-145 by SRF and Nkx2.5.

Deletions of the 4.2-kb miR-143/145 enhancer revealed that a 0.9-kb region was sufficient for miR-143/145 cardiac and smooth muscle expression (FIG. 2a). Within this regulatory region, cis elements were observed that are highly conserved between human, mouse, and zebrafish that represented potential binding sites for the essential cardiac transcription factors, serum response factor (SRF) and Nkx2.5 (FIG. 11a). SRF plays a dual role in cardiac and SMC development, influencing both proliferation and differentiation depending on the types of co-activators or repressors present at specific developmental or cellular stages[20]. The potent SRF co-activator, Myocd[21], is a component of a molecular switch for the VSMC fate[22] and is sufficient to effect both structural and physiological attributes of this cell type[23]. SRF weakly activated the miR-143/145 enhancer upstream of a luciferase reporter, but co-transfection of Myocd synergistically and robustly activated luciferase activity in Cos-1 cells (FIG. 2b). Mutation of the highly conserved CArG box in the SRF binding site decreased Myocd-dependent luciferase activity (FIG. 2b). Nkx2.5 could also independently activate this enhancer, and the combination of SRF, Myocd, and Nkx2.5, which also interacts with SRF[24], had additive effects on luciferase activity. Mutation of each binding site progressively decreased luciferase activity (FIG. 2b).

In vivo, mutation of the SRF binding site disrupted lacZ expression in the outflow tract and aorta, while disruption of the Nkx2.5 binding site diminished expression in the ventricles and atria (FIG. 2a), suggesting modular regulation by the enhancer. Mutation of both the SRF and Nkx2.5 binding sites abolished all activity of the enhancer within the heart (FIG. 2a). VSMC and atrial expression post-natally was also dependent upon the SRF-binding cis element (FIG. 11b). Electromobility shift assay confirmed SRF could specifically bind to the putative binding site in the miR-143/145 enhancer (FIG. 11c). Furthermore, miR-143 and miR-145 were each expressed at lower levels in SRF-null EBs compared to wild-type EBs (FIG. 2c). The levels were also reduced in mesoderm-rescued SRF-null EBs[14], confirming that the decreases did not reflect the absence of mesoderm. Similarly, miR-143 and miR-145 expression was also decreased in hearts of Nkx2.5 mutant mouse embryos in a dose-dependent fashion (FIG. 2d).

Figure 12A:
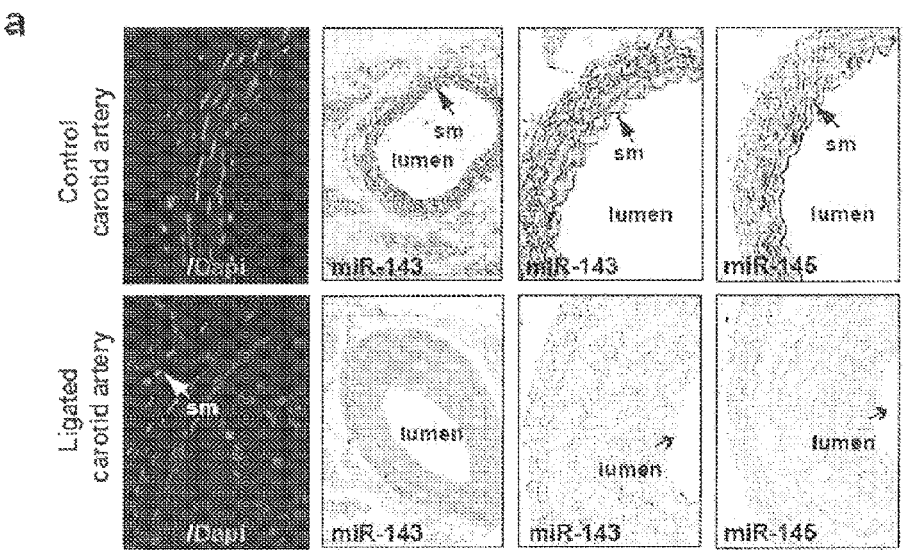
FIGS. 12A and 12B depict: Cross-sections from mice 21 days post-ligation of the left carotid artery compared to the contralateral right carotid artery without ligation (control) (FIG. 12A); qPCR results of miR-29a, miR-143 or miR-145 expression in the border zone (BZ) or infarct zone (IZ) of mouse hearts after coronary ligation, relative to the non-ischemic distal zone (DZ) away from the infarct area (FIG. 12B).
Figure 12B:
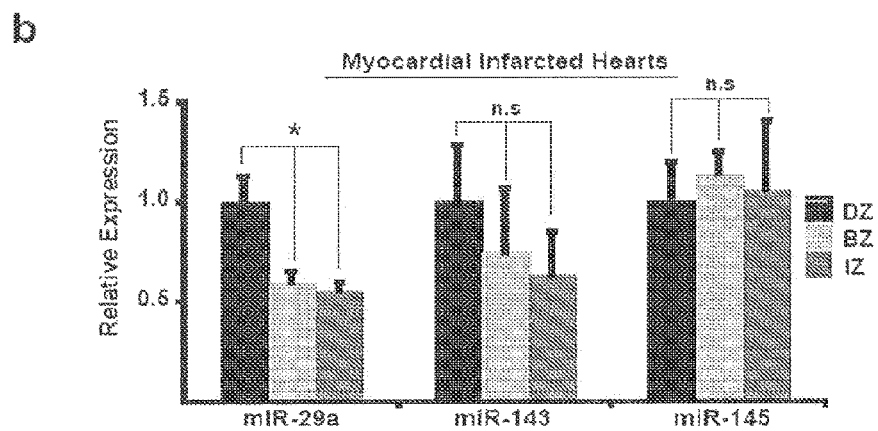

The dynamic stage-dependent expression of miR-143 and miR-145 raised the possibility that their expression may also vary with the oscillation of VSMCs between differentiated and proliferative phenotypes. VSMCs can modulate their phenotype during pathologic conditions such as atherosclerosis and vascular restenosis after angioplasty, resulting in neointimal hyperplasia due to VSMC proliferation[2]. In a mouse model of this proliferative switch, ligation of the carotid arteries typically results in narrowing of the vascular lumen as a result of phenotypic modulation and proliferation of VSMCs[23]. qPCR revealed marked decreases in miR-145 and miR-143 expression in injured carotid arteries compared to contralateral control vessels (FIG. 2e). miR-21 expression was increased as expected, and miR-16 was unchanged, demonstrating the presence of intact small RNAs[25]. In situ hybridization of injured and control carotid arteries also revealed marked downregulation of miR-143 and miR-145 expression in the thickened vascular wall, coincident with decreased expression of the differentiation marker, smooth muscle α-actin (α-SMA) (FIG. 12a). As a control, miR-143 and miR-145 levels were unchanged in cardiac muscle after injury (FIG. 12b). Interestingly, transcripts of miR-145, but not miR-143, were also downregulated to nearly undetectable levels in atherosclerotic lesions, exemplified by neointimal hyperplasia (FIG. 2f).

FIGS. 2A-F. SRF and Nkx2.5 directly regulate cardiac and smooth muscle expression of miR-143 and miR-145. (a) Summary of the deletion and mutation analyses of the upstream enhancer region of miR-143/145 illustrating in vivo sufficiency of a 0.9 kb genomic fragment. Asterisks (*) indicate mutations in the SRF or Nkx2.5 binding sites. Construct numbers match corresponding images of β-gal activity focused on heart region. (b) Fold-activation of luciferase activity directed by introduction of SRF, Myocd or Nkx2.5 expression vectors with the miR-143/145 enhancer in Cos-1 cells. Luciferase activity from enhancers containing mutations in each binding site is indicated. All changes were statistically significant. (c) miR-143 and miR-145 expression levels assessed by qPCR in SRF$^{null}$ day 10 embryoid bodies (EBs) compared to WT EBs or SRP$^{null}$ EBs with miR-1 or miR-133 expression. (d) qPCR of miR-143 and miR-145 showing reduced expression in Nkx2.5$^{+/-}$ and Nkx2.5$^{-/-}$ E9.5 hearts relative to WT. (e) qPCR showing downregulation of miR-143 and miR-145 expression in the injured vessel (e) or atherosclerotic lesion (f) compared to normal arterial expression; miR-16 was used as a control; miR-21 was increased in the injured vessel. Results shown in (b-f)are the average of three experiments. (ot, outflow tract; ra, right atrium; lv, left ventricle; rv, right ventricle; la, left atrium; dorsal aorta). *, p<0.05. Error bars indicate SD.

FIGS. 11A-C. (a) Putative SRF and Nkx2.5 binding sites (green sequence) within the 900 bp cis-regulatory element of miR-143 and miR-145. (b) LacZ expression of the 900 bp cis-acting regulatory element was present in the smooth muscle of the aorta, but a mutation of the SRF binding site eliminated enhancer activity. (c) Electrophoretic mobility-shift assay using radiolabeled probe for the SRF binding site. Competition with cold wild type (WT) or mutant (MT) probe indicates specificity of band.

FIGS. 12A and B. (a) Cross-sections from mice 21 days post-ligation of the left carotid artery compared to the contralateral right carotid artery without ligation (control). Immunohistochemistry revealed that smooth muscle (sm) alpha-actin staining (SMA, red) was reduced in the ligated vessel compared to control. miR-143 and miR-145 expression (DIG-AP staining, dark purple) was markedly reduced in the ligated artery. (b) qPCR results of miR-29a, miR-143 or miR-145 expression in the border zone (BZ) or infarct zone (IZ) of mouse hearts after coronary ligation, relative to the non-ischemic distal zone (DZ) away from the infarct area.

Figure 3:
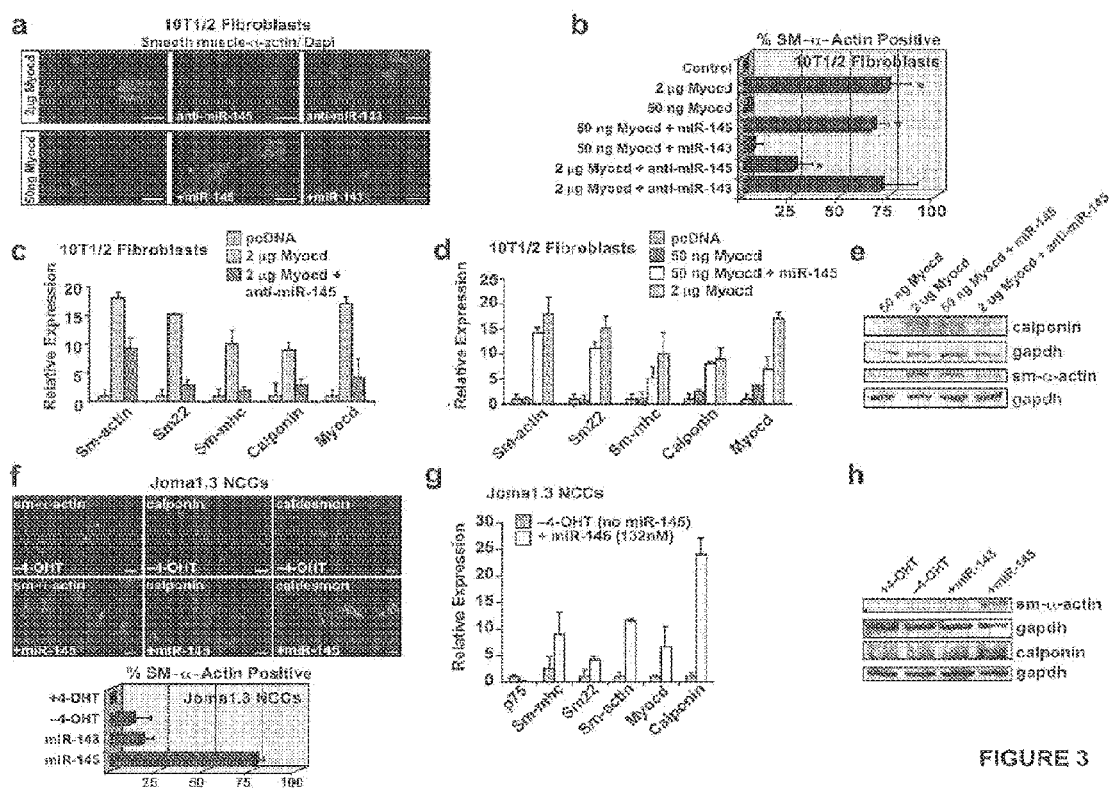
FIGS. 3A-H depict the role of miR-145 in directing vascular smooth muscle cell (VSMC) fate.
Figure 13:
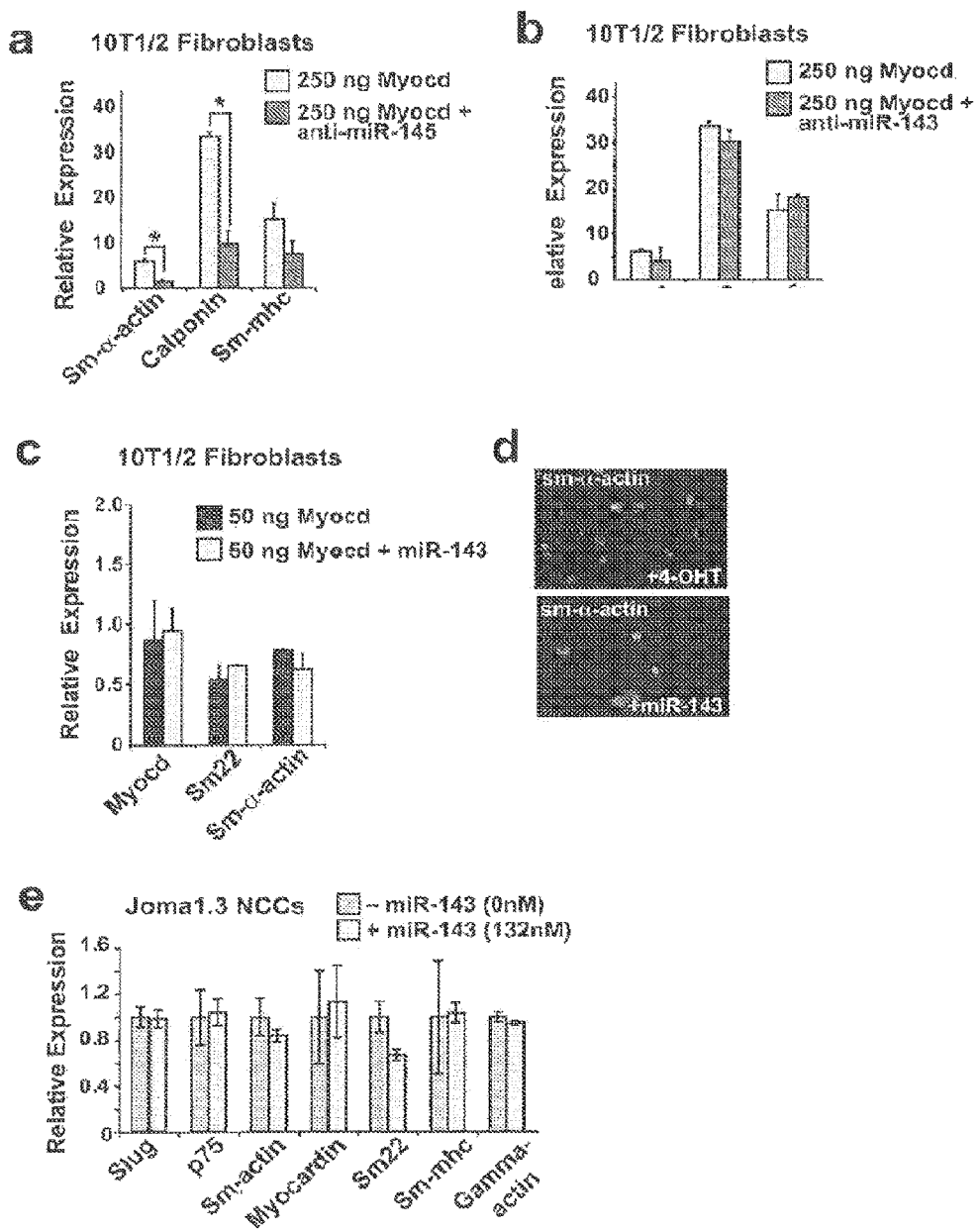
FIGS. 13A-E depict qPCR of smooth muscle markers in fibroblasts or in neural crest cells (FIGS. 13A, 13B, 13C, and 13E); and immunocytochemistry of smooth muscle α-actin in Joma1.3 neural crest cells (FIG. 13D).

The bimodal expression of miR-143 and miR-145 early during VSMC induction, and subsequently during the maturation into a non-proliferating, differentiated phenotype, prompted an investigation of their potential function in these settings. Since miR-145 and -143 expression was directly activated by SRF-Myocd, it was first investigated whether either miRNA's expression was necessary for Myocd-induced reprogramming of fibroblasts into VSMCs. Introduction of 1-2 μg of Myocd into fibroblasts reliably resulted in >50% conversion to VSMCs[20]. Inhibition of miR-145 using cholesterol-modified antisense oligonucleotides (antagomiRs)[26] blocked Myocd's ability to convert fibroblasts into VSMCs as illustrated by α-SMA immunostaining and expression of multiple smooth muscle markers assessed by qPCR and western blot (FIG. 3a-c, e). The knockdown of miR-143 had little effect on Myocd-induced smooth muscle conversion (FIG. 3a, FIG. 3b, FIG. 13a,b). Neither miRNA was sufficient to reprogram fibroblast cells. However, miR-145 potentiated Myocd's reprogramming effects. Although 50 ng of Myocd was insufficient to induce VSMC gene expression, simultaneous addition of miR-145, but not miR-143, resulted in robust VSMC differentiation, equivalent to that observed with 1-2 μg of Myocd (FIG. 3b, FIG. 3d, FIG. 3e and FIG. 13c). Thus, miR-145 activity was required for Myocd-dependent conversion of fibroblasts into VSMCs, and miR-145 robustly potentiated Myocd's effects.

To test an alternative cell type in which miR-145 may be sufficient for VSMC differentiation, a multipotent neural crest stem cell line was used that can differentiate into numerous cell types (e.g., melanocytes, chondrocytes, neurons), including VSMCs, upon exposure to 5 days of TGF-β[27]. Remarkably, introduction of miR-145, but not miR-143, into neural crest stem cells was sufficient to guide ~75% of cells into the VSMC lineage within only twenty-four hours, as determined by immunocytochemistry with multiple markers (FIG. 3f). qPCR and western blot revealed upregulation of numerous markers of VSMC differentiation, including α-SMA, SM-22α, and smooth muscle myosin heavy chain (sm-MHC) with miR-145 but not -143 (FIG. 3g and FIG. 3h; FIG. 13d,e). Thus, miR-145 was sufficient for directing the VSMC fate from multipotent neural crest stem cells.

FIGS. 3A-G. miR-145 directs vascular smooth muscle cell fate. (a) Immunocytochemistry showing smooth muscle (SM) α-actin (red) staining of 10T1/2 fibroblasts reprogrammed into SM by 2 μg Myocd with or without an inhibitor of miR-145 (anti-miR-145) or miR-143 (anti-miR-143); 50 ng of Myocd with or without miR-145 or miR-143 is also shown; nuclear stain, Dapi (blue). (b) Quantification of SM-α-actin positive cells upon Myocd and miR-145/miR-143 expression or inhibition. (c) qPCR of SM gene expression in fibroblasts transfected with Myocd with or without anti-miR-145. (d) qPCR of SM gene expression in fibroblasts transfected with 50 ng Myocd with or without miR-145 compared to 2 ug of Myocd. (e) Western blot of calponin and SM α-actin. (f) Immunocytochemistry of neural crest stem cells (Jomal.3 NCCs) with or without miR-145 using SM α-actin, calponin, or caldesmon-specific antibodies (green); tamoxifen (4OHT) was removed to allow differentiation in all settings. Quantification of percent SM α-actin+cells is indicated relative to total Dapi+nuclei (blue). (g) qPCR of SM gene expression in NCCs with miR-145 expression; p75 is a marker of the undifferentiated neural crest cells. Results shown in (b), (c), (d), (f) and (g) represent at least five experiments with error bars indicating SD. *, p<0.05.

FIGS. 13A-E. (a) qPCR of smooth muscle markers in fibroblasts treated with 250 ng Myocd with or without anti-miR-145 or (b) miR-143. (c) qPCR of smooth muscle markers in fibroblasts treated with 50 ng of Myocd with or without miR-143. (d) Immunocytochemistry of smooth muscle α-actin in Joma1.3 neural crest cells treated with tamoxifen (+4OHT) or miR-143. (e) qPCR of smooth muscle markers in neural crest cells (NCCs) with or without miR-143. Slug and p75 represent markers of undifferentiated NCCs.

FIGS. 14A and B (a) Relative luciferase activity of indicated 3' UTRs downstream of luciferase with or without miR-143. Predicted binding sites within the UTRs are indicated with residues complementary to miR-143 indicated in red capital letters. (b) Relative luciferase activity of indicated 3' UTRs downstream of luciferase with or without miR-145. Predicted binding sites within the UTRs are indicated with residues complementary to miR-145 indicated in red capital letters. No significant changes in luciferase activity were observed with any of these 3' UTRs.

Figure 4:
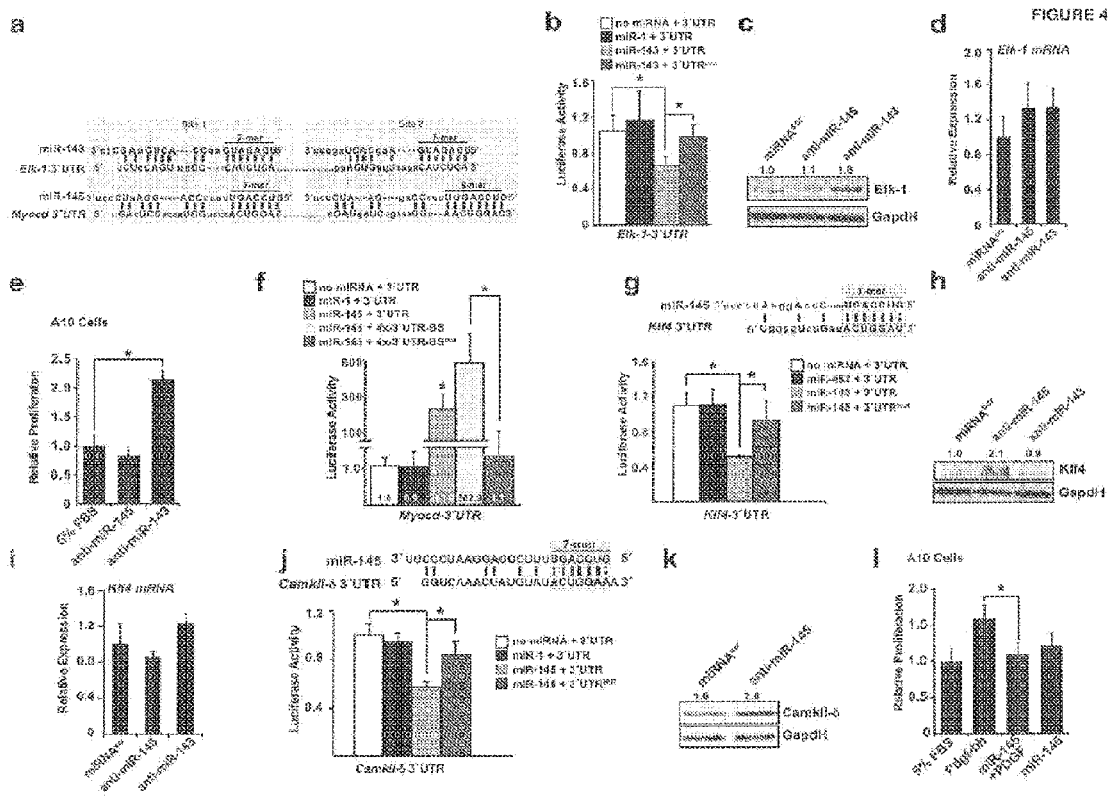
FIGS. 4A-L depict factors targeted by miR-143 and miR-145 to promote VSMC differentiation and repress proliferation.

The mechanism by which this family of miRNAs regulates VSMCs is dependent upon their mRNA targets. A bioinformatics approach incorporating sequence matching and mRNA secondary structure to predict mRNA targets (see Methods) revealed multiple highly conserved binding sites for miR-143 in the 3'UTR of Elk-1 and for miR-145 in the 3'UTR of Myocd (FIG. 4a). Growth signals repress smooth muscle gene expression by displacing Myocd from SRF with Elk-1, a ternary complex factor that acts as a myogenic repressor and an activator of VSMC proliferation[20]. In this system, SRF serves as a platform for myogenic coactivators or corepressors that compete for a common docking site thereby mediating VSMC phenotypic switching. To determine whether Elk-1 and Myocd are direct targets of miR-143 or miR-145, the 3' UTR of Elk-1 or Myocd was cloned into the 3'UTR of a CMV-driven luciferase reporter. In the presence of the Elk-1 3'UTR, miR-143 repressed luciferase activity; this repression was diminished upon mutation of one of the two miR-143 binding sites (FIG. 4b). The addition of an antagomiR to inhibit miR-143 in the A10 rat aortic VSMC line resulted in upregulation of Elk-1 protein, but not mRNA, consistent with translational repression of Elk-1 by miR-143 (FIG. 4c and FIG. 4d). Furthermore, inhibition of miR-143 caused a doubling of the proliferative rate of VSMCs, demonstrating miR-143's function in negatively regulating VSMC proliferation (FIG. 4e).

The presence of putative miR-145 binding sites in the Myocd 3' UTR seemed counter to the observed effects of miR-145 in potentiating Myocd's reprogramming effects. However, when we cloned the Myocd 3'UTR into a CMV-driven luciferase vector, it was found that introduction of miR-145, but not miR-143, with the luciferase vector in Cos-1 cells resulted in a significant increase in the already high CMV-driven luciferase activity (FIG. 4f). The luciferase activation was largely lost upon mutation of the miR-145 binding site in the Myocd 3'UTR (FIG. 4O. Although antibodies to detect endogenous Myocd levels by western blot are not available, these findings are consistent with the recent observation that miRNAs can act as translational activators or repressors based upon the state of the cell cycle, which we also found to be the case[9]. This result suggests miR-145 may promote VSMC differentiation in part by stabilizing Myocd and functioning in a feed-forward reinforcement of its own expression by the SRF-Myocd complex, while miR-143 represses Myocd's competitor, Elk-1, thereby repressing proliferation.

Figure 14:
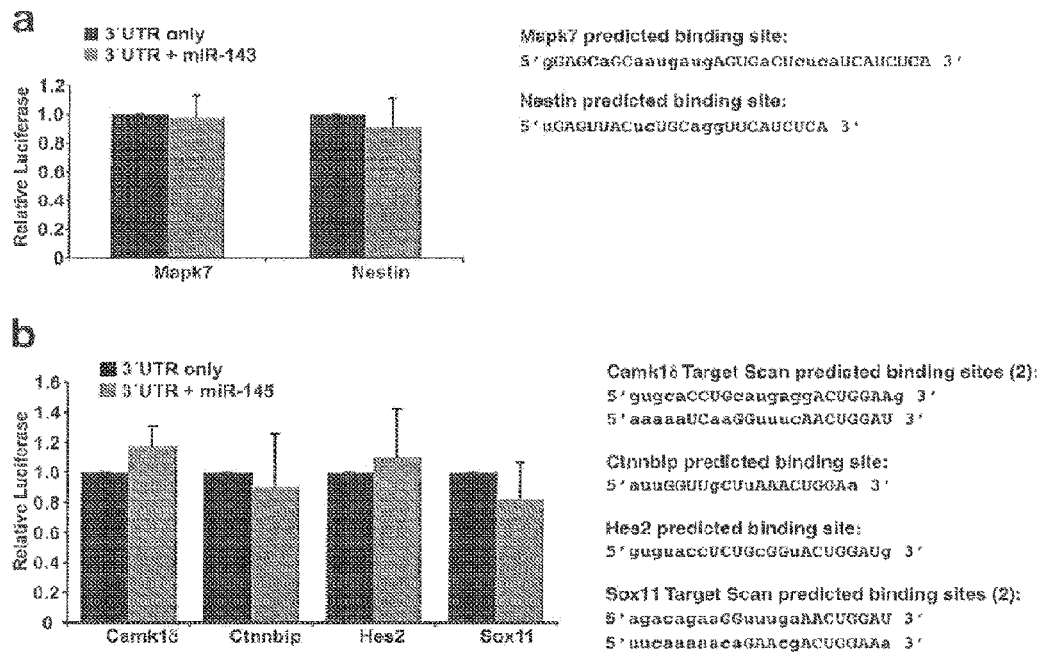
FIGS. 14A and 14B depict relative luciferase activity of indicated 3' UTRs downstream of luciferase with or without miR-143 (FIG. 14A) or with or without miR-145 (FIG. 14B).

In addition to Myocd, the bioinformatics approach also identified potential miR-145 binding sites in several other positive regulators of smooth muscle proliferation, including Kruppel-like factor 4 (Klf4) and Calmodulin kinase II-delta (CamkIIδ). Klf4 is a transcription factor rapidly induced in post-injury proliferating VSMCs, where it interacts with enhancers in smooth muscle growth genes, inhibits smooth muscle differentiation genes, and represses Myocd expression[28]. The miR-145 binding site in the 3'UTR of Klf4 specifically mediated miR-145-dependent repression in luciferase assays (FIG. 4g). Furthermore, knockdown of miR-145 in rat A10 VSMCs resulted in an increase in Klf4 protein levels, but no change in Klf4 mRNA levels (FIG. 4h and FIG. 4i). Similarly, a putative binding site in CamkII-δ, involved in multiple events including neointimal proliferation[29,30], was validated as a miR-145 target by luciferase and western analysis in VSMCs (FIG. 4j and FIG. 4k). Numerous predicted targets for both miRNAs that were not validated in luciferase assays are shown in FIG. 14. Consistent with miR-145 repression of genes involved in VSMC proliferation, introduction of miR-145 was sufficient to suppress the proliferative response normally induced by platelet-derived growth factor (Pdgf-β) in cultured VSMCs (FIG. 14). These findings suggest that miR-145 may promote VSMC differentiation by directly repressing numerous transcription factors that promote the proliferative state while stabilizing factors that promote the differentiated state of VSMCs.

FIGS. 4A-K. miR-143 and miR-145 target a network of factors to promote VSMC differentiation and repress proliferation. (a) Two miR-143 or miR-145 binding sites in mouse Elk-1 or Myocd 3' UTRs, respectively; sequence matching and seed regions are indicated. (b) Luciferase activity in Cos-1 cells upon introduction of wild type or mutated (mut) Elk-1. (c) Elk-1 protein and (d) mRNA in cell lysates from A10 VSMCs transfected with a scrambled (scr) miRNA or antisense oligo to miR-143 or miR-145 (anti-miR-145, anti-miR-143) assessed by western blot or qPCR. (e) Proliferation of VSMCs upon inhibition of miR-143 or miR-145 relative to control (5% FBS). (f) Luciferase activity in Cos-1 cells with Myocd 3' UTR sequences downstream of a CMV-driven luciferase reporter. Activity with no miRNA (negative control), miR-1 (control miRNA), or miR-145 is shown. The Myocd binding site (BS) was mutated in the context of a 4× concatemer to isolate the activation effect of the site. (g) Putative miR-145 BS in the mouse 3' UTR of Klf4 was validated by luciferase activity with wt or mutated Klf4-3' UTR upon introduction of no miRNA (negative control), miR-452 (control miRNA), or miR-145. (h) Analysis of Klf4 protein and mRNA (i) in cell lysates from A10 cells transfected with a scr miRNA, anti-miR-145, or anti-miR-143 by western blot (h) and qPCR (i). (j) Putative miR-145 binding site in the CamkII-δ3' UTR, and luciferase activity of wt or mutated CamkII-δ3' UTR with no miRNA (negative control), miR-1 (control miRNA), or miR-145. (k) Western analysis for CamkII-δ protein in A10 cells transfected with scr miRNA or anti-miR-145. (l) Proliferation of VSMCs relative to control. miR-145 inhibited proliferation induced by Pdgf-bb. Results shown represent at least five experiments with error bars indicating SD. Densitometry calculation performed by Image J. *, p<0.05.

Figure 5:
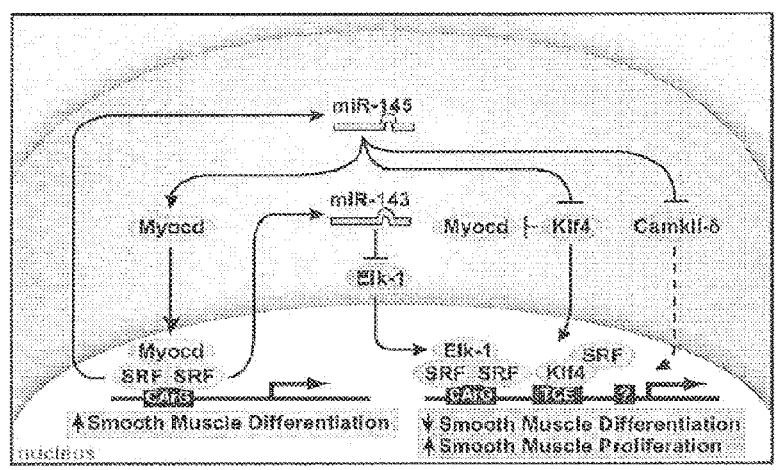
FIG. 5 depicts a model of miR-143 and miR-145 regulation of smooth muscle cell proliferation and differentiation.

FIG. 5. Model of miR-143 and miR-145 regulation of smooth muscle cell proliferation and differentiation. miR-143 and miR-145 function to repress multiple factors that normally promote the proliferative smooth muscle phenotype (purple). miR-145 has a positive effect on Myocd activity to concurrently promote the more differentiated smooth muscle phenotype (pink), thereby also functioning to reinforce its own expression. Effects of miR-145 and miR-143 converge on SRF-dependent transcription by regulation of co-activators and co-repressors to dictate the proliferative or differentiated phenotype of VSMCs. Positive regulation of Myocd by miR-145 results in reinforcement of miR-145 and miR-143 expression and the differentiated phenotype. Dashed lines indicate indirect effects.

REFERENCES

1. Ross, R. The pathogenesis of atherosclerosis: A perspective for the 1990s. *Nature* 362, 801-809 (1993).
2. Owens, G. K., Kumar, M. S. & Wamhoff, B. R. Molecular regulation of vascular smooth muscle cell differentiation in development and disease. *Physiol. Rev.* 84, 767-801 (2004).
3. Yoshida, T. & Owens, G. K. Molecular determinants of vascular smooth muscle cell diversity. *Circ. Res.* 96, 280-291 (2005).
4. Kloosterman, W. P. & Plasterk, R. H. The diverse functions of microRNAs in animal development and disease. *Dev. Cell* 11, 441-450 (2006).
5. Calin, G. A. & Croce, C. M. MicroRNA signatures in human cancers. *Nat. Rev. Cancer* 6, 857-866 (2006).
6. Zhao, Y. & Srivastava, D. A developmental view of microRNA function. *Trends Biochem. Sci.* 32, 189-197 (2007).
7. Bartel, D. P. MicroRNAs: Target recognition and regulatory functions. *Cell* 136, 215-233 (2009).
8. Rajewsky, N. microRNA target predictions in animals. *Nat. Genet.* 38 Suppl, S8-13 (2006).
9. Vasudevan, S., Tong, Y. & Steitz, J. A. Switching from repression to activation: microRNAs can up-regulate translation. *Science* 318, 1931-1934 (2007).
10. Zhao, Y., Samal, E. & Srivastava, D. Serum response factor regulates a muscle-specific microRNA that targets Hand2 during cardiogenesis. *Nature* 436, 214-220 (2005).
11. Kwon, C., Han, Z., Olson, E. N. & Srivastava, D. MicroRNA1 influences cardiac differentiation in *Drosophila* and regulates Notch signaling. *Proc. Natl. Acad. Sci. USA* 102, 18986-18991 (2005).

12. Chen, J. F. et al. The role of microRNA-1 and microRNA-133 in skeletal muscle proliferation and differentiation. *Nat. Genet.* 38, 228-233 (2006).
13. Zhao, Y. et al. Dysregulation of cardiogenesis, cardiac conduction, and cell cycle in mice lacking miRNA-1-2. *Cell* 129, 303-317 (2007).
14. Ivey, K. N. et al. MicroRNA regulation of cell lineages in mouse and human embryonic stem cells. *Cell Stem Cell* 2, 219-229 (2008).
15. Liu, N. et al. An intragenic MEF2-dependent enhancer directs muscle-specific expression of microRNAs 1 and 133. *Proc. Natl. Acad. Sci. USA* 104, 20844-20849 (2007).
16. Wang, Y., Medvid, R., Melton, C., Jaenisch, R. & Blelloch, R. DGCR8 is essential for microRNA biogenesis and silencing of embryonic stem cell self-renewal. *Nat. Genet.* 39, 380-385 (2007).
17. Cai, C. L. et al. Isl1 identifies a cardiac progenitor population that proliferates prior to differentiation and contributes a majority of cells to the heart. *Dev. Cell* 5, 877-889 (2003).
18. Srinivas, S. et al. Cre reporter strains produced by targeted insertion of EYFP and ECFP into the ROSA26 locus. *BMC Dev. Biol.* 1, 4 (2001).
19. Moretti, A. et al. Multipotent embryonic isl1+progenitor cells lead to cardiac, smooth muscle, and endothelial cell diversification. *Cell* 127, 1151-1165 (2006).
20. Wang, Z. et al. Myocardin and ternary complex factors compete for SRF to control smooth muscle gene expression. *Nature* 428, 185-189 (2004).
21. Wang, D. et al. Activation of cardiac gene expression by myocardin, a transcriptional cofactor for serum response factor. *Cell* 105, 851-862 (2001).
22. Chen, J., Kitchen, C. M., Streb, J. W. & Miano, J. M. Myocardin: A component of a molecular switch for smooth muscle differentiation. *J. Mol. Cell. Cardiol.* 34, 1345-1356 (2002).
23. Long, X., Bell, R D., Gerthoffer, W. T., Zlokovic, B. V. & Miano, J. M. Myocardin is sufficient for a smooth muscle-like contractile phenotype. *Arterioscler. Thromb. Vasc. Biol.* 28, 1505-1510 (2008).
24. Chen, C. Y. & Schwartz, R. J. Recruitment of the tinman homolog Nkx-2.5 by serum response factor activates cardiac alpha-actin gene transcription. *Mol. Cell. Biol.* 16, 6372-6384 (1996).
25. Ji, R. et al. MicroRNA expression signature and antisense-mediated depletion reveal an essential role of MicroRNA in vascular neointimal lesion formation. *Circ. Res.* 100, 1579-1588 (2007).
26. Krutzfeldt, J. et al. Silencing of microRNAs in vivo with 'antagomirs'. *Nature* 438, 685-689 (2005).
27. Maurer, J. et al. Establishment and controlled differentiation of neural crest stem cell lines using conditional transgenesis. *Differentiation* 75, 580-591 (2007).
28. Liu, Y. et al. Kruppel-like factor 4 abrogates myocardin-induced activation of smooth muscle gene expression. *J. Biol. Chem.* 280, 9719-9727 (2005).
29. House, S. J. & Singer, H. A. CaMKII-delta isoform regulation of neointima formation after vascular injury. *Arterioscler. Thromb. Vasc. Biol.* 28, 441-447 (2008).
30. Mishra-Gorur, K., Singer, H. A. & Castellot, J. J., Jr. Heparin inhibits phosphorylation and autonomous activity of Ca(2+)/calmodulin-dependent protein kinase II in vascular smooth muscle cells. *Am. J. Pathol.* 161, 1893-1901 (2002).
31. Obernosterer, G., Martinez, J. & Alenius, M. Locked nucleic acid-based in situ detection of microRNAs in mouse tissue sections. *Nat. Protoc.* 2, 1508-1514 (2007).
32. Yamagishi, H. et al. Tbx1 is regulated by tissue-specific forkhead proteins through a common Sonic hedgehog-responsive enhancer. *Genes Dev.* 17, 269-281 (2003).
33. Kruger, J. & Rehmsmeier, M. RNAhybrid: microRNA target prediction easy, fast and flexible. *Nucleic Acids Res.* 34, W451-454 (2006).
34. Zuker, M. Mfold web server for nucleic acid folding and hybridization prediction. *Nucleic Acids Res.* 31, 3406-3415 (2003).
35. Wang, Z., Wang, D. Z., Pipes, G. C. & Olson, E. N. Myocardin is a master regulator of smooth muscle gene expression. *Proc. Natl. Acad. Sci. USA* 100, 7129-7134 (2003).
36. Yamamoto, M. et al. The roles of protein kinase C beta I and beta II in vascular smooth muscle cell proliferation. *Exp. Cell Res.* 240, 349-358 (1998).
37. Regan, C. P., Adam, P. J., Madsen, C. S. & Owens, G.K. Molecular mechanisms of decreased smooth muscle differentiation marker expression after vascular injury. *J. Clin. Invest.* 106, 1139-1147 (2000).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of inhibiting vascular smooth muscle cell (VSMC) proliferation in a blood vessel, the method comprising introducing, at or near a site of injury, disease, or disorder in the blood vessel:
   i) an implantable device comprising a miR-145 nucleic acid, or a nucleic acid comprising a nucleotide sequence encoding a miR-145 nucleic acid; or
   ii) a sustained release dosage form comprising a miR-145 nucleic acid, or a nucleic acid comprising a nucleotide sequence encoding a miR-145 nucleic acid.

2. The method of claim 1, wherein the injury is due to procedural vascular trauma, wherein the injury is due to accidental trauma, wherein the disease is atherosclerosis, or wherein the disorder is restenosis.

3. The method of claim 1, wherein the injury is due to procedural vascular trauma.

4. The method of claim 1, wherein the disease is atherosclerosis.

5. The method of claim 1, wherein the disorder is restenosis.

6. The method of claim 1, wherein said introducing results in an at least about 10% reduction in VSMC proliferation in the blood vessel.

7. The method of claim 1, wherein said introducing results in a decrease in diminution of blood vessel luminal cross-sectional area.

8. The method of claim 1, wherein the sustained release dosage form is a nanoparticle or a microparticle.

9. The method of claim 1, wherein said implantable device is a coronary stent, a peripheral stent, a catheter, an arterio-venous graft, an artificial by-pass graft, or a drug delivery balloon adapted for use in the vasculature.

10. The method of claim 9, wherein the nucleic acid is releasably embedded in, coated on, or embedded in and coated on, the implantable device.

11. The method of claim 1, wherein the miR-145 nucleic acid comprises a mature miR-145 nucleotide sequence.

12. The method of claim 1, wherein the miR-145 nucleic acid comprises the nucleotide sequence set forth in SEQ ID NO:4.

13. The method of claim 1, wherein the nucleic acid encoding a miR-145 nucleic acid is an expression construct, and wherein the miR-145-encoding nucleotide sequence is operably linked to a transcription regulatory element.

14. The method of claim 1, wherein the nucleic acid comprises at least one nuclease-resistant internucleosidic linkage.

15. The method of claim 14, wherein the internucleosidic linkage is selected from phosphorothioate, phosphorodithioate, phosphoramidate, phosphorodiamidate, methylphosphonate, P-chiral linkage, chiral phosphorothioate, phosphoroselenoate, phosphorodiselenoate, phosphoroanilothioate, phosphoranilidates, phosphotriester, aminoalkylphosphotriester, alkylphosphotriester, carbonate, carbamate, morpholino carbamate, 3'-thioformacetal, and silyl.

16. The method of claim 1, wherein the nucleic acid comprises at least one modified nucleotide.

17. The method of claim 16, wherein the modified nucleotide is a 2'-deoxy-2'-fluoro modified nucleotide, a 2'-deoxy-modified nucleotide, a locked nucleotide, an abasic nucleotide, a 2'-ammo-modified nucleotide, a 2'-alkyl-modified nucleotide, a morpholino nucleotide, a phosphoramidate, or a non-natural base comprising nucleotide.

18. The method of claim 1, wherein the miR-145 nucleic acid comprises a nucleotide sequence having at least 95% nucleotide sequence identity to the sequence set forth in SEQ ID NO:4.

* * * * *

SEQUENCE LISTING

<160> NUMBER OF SEQ ID NOS: 62

<210> SEQ ID NO 1
<211> LENGTH: 106
<212> TYPE: RNA
<213> ORGANISM: Homo sapiens

<400> SEQUENCE: 1
gcgcagcgcc cugucuccca gccugaggug cagugcugca ucucugguca guugggaguc      60
ugagaugaag cacuguagcu caggaagaga gaaguuguuc ugcagc                    106

<210> SEQ ID NO 2

```
<211> LENGTH: 21
<212> TYPE: RNA
<213> ORGANISM: Homo sapiens

<400> SEQUENCE: 2
ugagaugaag cacuguagcu c                                              21

<210> SEQ ID NO 3
<211> LENGTH: 88
<212> TYPE: RNA
<213> ORGANISM: Homo sapiens

<400> SEQUENCE: 3
caccuugucc ucacggucca guuuucccag gaaucccuua gaugcuaaga uggggauucc    60
uggaaauacu guucuugagg ucaugguu                                       88

<210> SEQ ID NO 4
<211> LENGTH: 23
<212> TYPE: RNA
<213> ORGANISM: Homo sapiens

<400> SEQUENCE: 4
guccaguuuu cccaggaauc ccu                                            23

<210> SEQ ID NO 5
<211> LENGTH: 25
<212> TYPE: RNA
<213> ORGANISM: Homo sapiens

<400> SEQUENCE: 5
ugacuccaca auggucccac uggac                                          25

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
gtccagtggg accattgtgg agtca                                          25

<210> SEQ ID NO 7
<211> LENGTH: 24
<212> TYPE: RNA
<213> ORGANISM: Homo sapiens

<400> SEQUENCE: 7
agaugaucag aaaggcaacu ggac                                           24

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
gtccagttgc ctttctgatc atct                                           24

<210> SEQ ID NO 9
<211> LENGTH: 63
<212> TYPE: RNA
<213> ORGANISM: Mus musculus
```

```
<400> SEQUENCE: 9 ccugagguqc agugcugcau cucuggucag uugggagucu gagaugaagc acuguagcuc      60
agg                                                                   63

<210> SEQ ID NO 10
<211> LENGTH: 105
<212> TYPE: RNA
<213> ORGANISM: Rattus norvegicus

<400> SEQUENCE: 10
gcggagcgcc ugucuccag ccugaggugc agugcugcau cucuggucag uugggagucu       60
gagaugaagc acuguagcuc aggaagggag aagauguucu gcagc                    105

<210> SEQ ID NO 11
<211> LENGTH: 106
<212> TYPE: RNA
<213> ORGANISM: Macaca mulatta

<400> SEQUENCE: 11
gcgcagcgcc gugucuccca gccugaggug cagugcugca ucucgguca guugggaguc       60 ugagaugaag cacuguagcu caggaagaga gaaguuguuc ugcagc                    106

<210> SEQ ID NO 12
<211> LENGTH: 106
<212> TYPE: RNA
<213> ORGANISM: Lagothrix lagotricha

<400> SEQUENCE: 12
gcgcagcgcc cugucuccca gccugaggug cagugcugca ucucgguca guugggaguc       60 ugagaugaag cacuguagcu caggaagaga gaaguuguuc ugcagc                    106

<210> SEQ ID NO 13
<211> LENGTH: 106
<212> TYPE: RNA
<213> ORGANISM: Gorilla gorilla

<400> SEQUENCE: 13
gcgcagcgcc cugucuccca gccugaggug cagugcugca ucucgguca guugggaguc       60 ugagaugaag cacuguagcu caggaagaga gaaguuguuc ugcagc                    106

<210> SEQ ID NO 14
<211> LENGTH: 70
<212> TYPE: RNA
<213> ORGANISM: Mus musculus

<400> SEQUENCE: 14
cucacggucc aguuucccca ggaaucccuu ggaugcuaag auggggauuc cuggaaauac       60
uguucuugag                                                            70

<210> SEQ ID NO 15
<211> LENGTH: 88
<212> TYPE: RNA
<213> ORGANISM: Gorilla gorilla

<400> SEQUENCE: 15
caccuugucc ucacggucca guuucccag gaaucccuua gaugcuaaga uggggauucc        60
uggaaauacu guucuugagg ucaugguu                                        88

<210> SEQ ID NO 16
```

```
<211> LENGTH: 88
<212> TYPE: RNA
<213> ORGANISM: Rattus norvegicus

<400> SEQUENCE: 16
caccuugucc ucacggucca guuucccag gaaucccuug gaugcuaaga uggggauucc    60
uggaaauacu guucuugagg ucauggcu                                     88

<210> SEQ ID NO 17
<211> LENGTH: 88
<212> TYPE: RNA
<213> ORGANISM: Macaca mulatta

<400> SEQUENCE: 17
caccuugucc ucacggucca guuucccag gaaucccuua aaugcuaaga uggggauucc    60
uggaaauacu guucuugagg ucaugguu                                     88

<210> SEQ ID NO 18
<211> LENGTH: 88
<212> TYPE: RNA
<213> ORGANISM: Bos taurus

<400> SEQUENCE: 18
caccuugucc ucacggucca guuucccag gaaucccuua gaugcuaaga uggggauucc    60
uggaaauacu guucuugagg ucaugguu                                     88

<210> SEQ ID NO 19
<211> LENGTH: 19
<212> TYPE: RNA
<213> ORGANISM: Homo sapiens

<400> SEQUENCE: 19
ugagaugaag cacuagcuc                                               19

<210> SEQ ID NO 20
<211> LENGTH: 19
<212> TYPE: RNA
<213> ORGANISM: Homo sapiens

<400> SEQUENCE: 20
ucuccaguua gccaucuca                                               19

<210> SEQ ID NO 21
<211> LENGTH: 20
<212> TYPE: RNA
<213> ORGANISM: Homo sapiens

<400> SEQUENCE: 21 ggaguggua agacaucuca                                               20

<210> SEQ ID NO 22
<211> LENGTH: 23
<212> TYPE: RNA
<213> ORGANISM: Homo sapiens

<400> SEQUENCE: 22
ggucaaacua uguauacugg aaa                                          23

<210> SEQ ID NO 23
<211> LENGTH: 22
<212> TYPE: RNA
<213> ORGANISM: Homo sapiens
```

<210> SEQ ID NO 23
<211> LENGTH: 22
<212> TYPE: RNA
<213> ORGANISM: Mus musculus

<400> SEQUENCE: 23
ugagaugaag cacuguagcu ca                                              22

<210> SEQ ID NO 24
<211> LENGTH: 22
<212> TYPE: RNA
<213> ORGANISM: Mus musculus

<400> SEQUENCE: 24
ugagaugaag cacuguagcu ca                                              22

<210> SEQ ID NO 25
<211> LENGTH: 22
<212> TYPE: RNA
<213> ORGANISM: Rattus norvegicus

<400> SEQUENCE: 25
ugagaugaag cacuguagcu ca                                              22

<210> SEQ ID NO 26
<211> LENGTH: 22
<212> TYPE: RNA
<213> ORGANISM: Gallus gallus

<400> SEQUENCE: 26
ugagaugaag cacuguagcu ca                                              22

<210> SEQ ID NO 27
<211> LENGTH: 21
<212> TYPE: RNA
<213> ORGANISM: Danio rerio

<400> SEQUENCE: 27
ugagaugaag cacuguagcu c                                               21

<210> SEQ ID NO 28
<211> LENGTH: 22
<212> TYPE: RNA
<213> ORGANISM: Homo sapiens

<400> SEQUENCE: 28
guccaguuuc ccaggaaucc cu                                              22

<210> SEQ ID NO 29
<211> LENGTH: 22
<212> TYPE: RNA
<213> ORGANISM: Mus musculus

<400> SEQUENCE: 29
guccaguuuc ccaggaaucc cu                                              22

<210> SEQ ID NO 30
<211> LENGTH: 22
<212> TYPE: RNA
<213> ORGANISM: Rattus norvegicus

<400> SEQUENCE: 30
guccaguuuc ccaggaaucc cu                                              22

<210> SEQ ID NO 31
<211> LENGTH: 22
<212> TYPE: RNA
<213> ORGANISM: Gallus gallus -continued

```
<400> SEQUENCE: 31
guccaguuuc ccaggaaucc cu                                        22

<210> SEQ ID NO 32
<211> LENGTH: 21
<212> TYPE: RNA
<213> ORGANISM: Danio rerio

<400> SEQUENCE: 32
guccaguuuc ccaggaaucc c                                         21

<210> SEQ ID NO 33
<211> LENGTH: 23
<212> TYPE: RNA
<213> ORGANISM: Drosophila melanogaster

<400> SEQUENCE: 33
guccaguuuc ccauggaauc cac                                       23

<210> SEQ ID NO 34
<211> LENGTH: 34
<212> TYPE: DNA
<213> ORGANISM: Homo sapiens

<400> SEQUENCE: 34
gggagcagcc ttgccatata agggcaggag cccc                           34

<210> SEQ ID NO 35
<211> LENGTH: 34
<212> TYPE: DNA
<213> ORGANISM: Homo sapiens

<400> SEQUENCE: 35
gggagcagcc ttgctaccgc agggcaggag cccc                           34

<210> SEQ ID NO 36
<211> LENGTH: 27
<212> TYPE: DNA
<213> ORGANISM: Homo sapiens

<400> SEQUENCE: 36
gggaaagact gccaagtgct cgtggcc                                   27

<210> SEQ ID NO 37
<211> LENGTH: 27
<212> TYPE: DNA
<213> ORGANISM: Homo sapiens

<400> SEQUENCE: 37
gggaaagact gccgtgagct cgtggcc                                   27

<210> SEQ ID NO 38
<211> LENGTH: 34
<212> TYPE: RNA
<213> ORGANISM: Homo sapiens

<400> SEQUENCE: 38
ggagcagcaa ugaugaguga cucucaucau cuca                           34

<210> SEQ ID NO 39
<211> LENGTH: 25
<212> TYPE: RNA
<213> ORGANISM: Homo sapiens
```

-continued

```
<400> SEQUENCE: 39
ugaguuacuc ugcagguuca ucuca                                         25

<210> SEQ ID NO 40
<211> LENGTH: 24
<212> TYPE: RNA
<213> ORGANISM: Homo sapiens

<400> SEQUENCE: 40
gugcaccugc augaggacug gaag                                          24

<210> SEQ ID NO 41
<211> LENGTH: 23
<212> TYPE: RNA
<213> ORGANISM: Homo sapiens

<400> SEQUENCE: 41
aaaaaucaag guuucaacug gau                                           23

<210> SEQ ID NO 42
<211> LENGTH: 20
<212> TYPE: RNA
<213> ORGANISM: Homo sapiens

<400> SEQUENCE: 42
auugguugcu uaaacuggaa                                               20

<210> SEQ ID NO 43
<211> LENGTH: 23
<212> TYPE: RNA
<213> ORGANISM: Homo sapiens

<400> SEQUENCE: 43
guguaccucu gcgguacugg aug                                           23

<210> SEQ ID NO 44
<211> LENGTH: 23
<212> TYPE: RNA
<213> ORGANISM: Homo sapiens

<400> SEQUENCE: 44
agacagaagg uuugaaacug gau                                           23

<210> SEQ ID NO 45
<211> LENGTH: 23
<212> TYPE: RNA
<213> ORGANISM: Homo sapiens

<400> SEQUENCE: 45
uucaaaaaca gaacgacugg aaa                                           23

<210> SEQ ID NO 46
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 46
gaccagagat gcagcactgc acctcaggct gggaga                             36

<210> SEQ ID NO 47
<211> LENGTH: 27
<212> TYPE: DNA
```

```
<213> ORGANISM: Artificial Sequence
<220> FEATURE:
<223> OTHER INFORMATION: Synthetic oligonucleotide

<400> SEQUENCE: 47
tgcagcactg cacctcaggc tgggaga                                27

<210> SEQ ID NO 48
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 48
gaccagagat gcagcactgc acctcagg                               28

<210> SEQ ID NO 49
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 49
tctctcttcc tgagctacag tgcttcatct cagactc                     37

<210> SEQ ID NO 50
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 50
tctctcttcc tgagctacag tgcttcat                               28

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 51
agctacagtg cttcatctca gactc                                  25

<210> SEQ ID NO 52
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 52
agggattcct gggaaaactg gaccgtgagg                             30

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53
agggattcct gggaaaactg g                                      21
```

```
<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
gggaaaactg gaccgtgagg                                                   20

<210> SEQ ID NO 55
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 55
cctcaagaac agtatttcca ggaatcccc                                         29

<210> SEQ ID NO 56
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 56
cctcaagaac agtatttcca gg                                                22

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 57
cagtatttcc aggaatcccc                                                   20

<210> SEQ ID NO 58
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 58
gggagcagcc ttgccatata agggcagg                                          28

<210> SEQ ID NO 59
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 59
gggagcagcc ttgctaccga agggcagg                                          28

<210> SEQ ID NO 60
<211> LENGTH: 19
<212> TYPE: DNA
<213> ORGANISM: Artificial Sequence
<220> FEATURE:
<223> OTHER INFORMATION: Synthetic primer
```

-continued

```
<400> SEQUENCE: 60
gcatctctgg tcagttggg                                              19

<210> SEQ ID NO 61
<211> LENGTH: 17
<212> TYPE: DNA
<213> ORGANISM: Artificial Sequence
<220> FEATURE:
<223> OTHER INFORMATION: Synthetic primer

<400> SEQUENCE: 61
gacctcaaga acagtat                                                17

<210> SEQ ID NO 62
<211> LENGTH: 18
<212> TYPE: RNA
<213> ORGANISM: Homo sapien

<400> SEQUENCE: 62
uggggucuga uacuggau                                               18
```